(12) United States Patent
Baraban

(10) Patent No.: US 11,648,237 B2
(45) Date of Patent: *May 16, 2023

(54) 5HT AGONISTS FOR TREATING DISORDERS

(71) Applicant: The Regents of the University of California, Oakland, CA (US)

(72) Inventor: Scott C. Baraban, Novato, CA (US)

(73) Assignee: The Regents of the University of California, Oakland, CA (US)

(*) Notice: Subject to any disclaimer, the term of this patent is extended or adjusted under 35 U.S.C. 154(b) by 609 days.

This patent is subject to a terminal disclaimer.

(21) Appl. No.: 16/679,112

(22) Filed: Nov. 8, 2019

(65) Prior Publication Data
US 2020/0147048 A1 May 14, 2020

Related U.S. Application Data

(62) Division of application No. 15/552,784, filed as application No. PCT/US2016/019368 on Feb. 24, 2016, now Pat. No. 10,874,643.

(60) Provisional application No. 62/120,726, filed on Feb. 25, 2015.

(51) Int. Cl.
A61K 31/4184 (2006.01)
A61K 45/06 (2006.01)
A61K 31/496 (2006.01)
A61K 31/7048 (2006.01)
A61K 31/137 (2006.01)
A61P 25/08 (2006.01)
A61K 31/55 (2006.01)

(52) U.S. Cl.
CPC ........ A61K 31/4184 (2013.01); A61K 31/137 (2013.01); A61K 31/496 (2013.01); A61K 31/55 (2013.01); A61K 31/7048 (2013.01); A61K 45/06 (2013.01); A61P 25/08 (2018.01)

(58) Field of Classification Search
None
See application file for complete search history.

(56) References Cited

U.S. PATENT DOCUMENTS

| | | | |
|---|---|---|---|
| 4,011,322 A | 3/1977 | Rahtz et al. | |
| 6,559,293 B1 | 5/2003 | Almarsson et al. | |
| 6,780,869 B1 | 8/2004 | Green et al. | |
| 9,925,172 B2 * | 3/2018 | Baraban | A61K 31/4166 |
| 10,874,643 B2 | 12/2020 | Baraban | |
| 2003/0166581 A1 | 9/2003 | Almarsson et al. | |
| 2005/0215589 A1 | 9/2005 | Crossley et al. | |

(Continued)

FOREIGN PATENT DOCUMENTS

| | | |
|---|---|---|
| EP | 1 787 679 A1 | 5/2007 |
| JP | 2011-518154 A | 6/2011 |

(Continued)

OTHER PUBLICATIONS

Anonymous (Jun. 1, 2012). "Highlights of prescribing information Belviq," pp. 1-28, retrieved on Oct. 30, 2020.

(Continued)

Primary Examiner — Melissa S Mercier
(74) Attorney, Agent, or Firm — Irina E. Britva; Mintz, Levin, Cohn, Ferris, Glovsky and Popeo, P.C.

(57) ABSTRACT

Provided, inter alia, are methods for treating an epilepsy disorder using a 5HT receptor agonist, or a pharmaceutically acceptable salt thereof.

10 Claims, 22 Drawing Sheets
Specification includes a Sequence Listing.

WT sibling

SEQ ID NO:1    F   M   I   L   L
SEQ ID NO:2    TTCATGATTTTACTC scn1Lab mutant

SEQ ID NO:3    F   R   I   L   L
SEQ ID NO:4    TTCAGGATTTTACTC

(56) References Cited

U.S. PATENT DOCUMENTS

| | | |
|---|---|---|
| 2008/0064671 A1 | 3/2008 | Barlow et al. |
| 2011/0009351 A1 | 1/2011 | Thomas et al. |
| 2011/0052536 A1 | 3/2011 | Einav et al. |
| 2012/0232062 A1 | 9/2012 | Yang et al. |
| 2012/0276050 A1 | 11/2012 | Choong et al. |
| 2014/0329893 A1 | 11/2014 | Veech |
| 2018/0028499 A1 | 2/2018 | Baraban |
| 2021/0154171 A1 | 5/2021 | Baraban |

FOREIGN PATENT DOCUMENTS

| | | |
|---|---|---|
| JP | 2011-520900 A | 7/2011 |
| JP | 2012-526847 A | 11/2012 |
| WO | WO-2002/089731 A2 | 11/2002 |
| WO | WO-2002/089731 A3 | 11/2002 |
| WO | WO-2005/032329 A2 | 4/2005 |
| WO | WO-2005/032329 A3 | 4/2005 |
| WO | WO-2007/093880 A2 | 8/2007 |
| WO | WO-2007/093880 A3 | 8/2007 |
| WO | WO-2008/133884 A2 | 11/2008 |
| WO | WO-2009/038248 A1 | 3/2009 |
| WO | WO-2009/039246 A2 | 3/2009 |
| WO | WO-2009/039246 A3 | 3/2009 |
| WO | WO-2009/039248 A2 | 3/2009 |
| WO | WO-2009/039248 A3 | 3/2009 |
| WO | WO-2009/039248 A8 | 3/2009 |
| WO | WO-2009/105507 A2 | 8/2009 |
| WO | WO-2009/105507 A3 | 8/2009 |
| WO | WO-2009/128907 A1 | 10/2009 |
| WO | WO-2009/140416 A2 | 11/2009 |
| WO | WO-2009/140416 A3 | 11/2009 |
| WO | WO-2010/039195 A2 | 4/2010 |
| WO | WO-2010/039195 A3 | 4/2010 |
| WO | WO-2010/107739 A2 | 9/2010 |
| WO | WO-2010/107739 A3 | 9/2010 |
| WO | WO-2010/107742 A2 | 9/2010 |
| WO | WO-2010/107742 A3 | 9/2010 |
| WO | WO-2010/132691 A1 | 11/2010 |
| WO | WO-2014/123909 A1 | 8/2014 |
| WO | WO-2015/026849 A1 | 2/2015 |
| WO | WO-2015/096119 A1 | 7/2015 |
| WO | WO-2016/203239 A1 | 12/2016 |

OTHER PUBLICATIONS

Berlie, H.D. et al. (Aug. 2013, e-published Jun. 26, 2013). "Evaluation of lorcaserin for the treatment of obesity," *Expert Opin Drug Metab Toxicol* 9(8):1053-1059.

Higgins, J.A. et al.(Oct. 2013, e-published Sep. 13, 2013). "From obesity to substance abuse: therapeutic opportunities for 5-HT2C receptor agonists," *Trends Pharmacol Sci* 34(10):560-570.

Levy, R.G. et al. (Mar. 14, 2012). "Ketogenic diet and other dietary treatments for epilepsy," *Cochrane Database Syst Rev* (3):CD001903.

Pisani, F. et al. (1999). "Antidepressant drugs and seizure susceptibility: from in vitro data to clinical practice," *Epilepsia* 40 Suppl 10:S48-56.

Takahashi, H. et al. (2010). "Effectiveness of Topiramate in Eleven Patients with Dravet Syndrome," *Brain & Development* 42(4):273-276. (English Translation of Abstract only).

Griffin, A.L. et al. (2019). "Zebrafish studies identify serotonin receptors mediating antiepileptic activity in Dravet syndrome," *Brain Communications* 1(1):fcz008.

Dravet Syndrome, zebrafish and clemizole, Beyond the Ion Channel, (Sep. 2013), 3 pages.

Zheng, F. et al. (Jun. 2014, e-published Apr. 9, 2014). "The Role of Canonical Transient Receptor Potential Channels in Seizure and Excitotoxicity," *Cells* 3(2):288-303.

Afrikanova, T. et al. (2013, e-published Jan. 14, 2013). "Validation of the zebrafish pentylenetetrazol seizure model: locomotor versus electrographic responses to antiepileptic drugs," PloS One 8(10):e54166.

Avedissian, M. et al. (2007). "Hippocampal gene expression analysis using the ORESTES methodology shows that homer 1a mRNA is upregulated in the acute period of the pilocarpine epilepsy model," *Hippocampus* 17(2):130-136.

Baraban S.C. et al. (2005). "Pentylenetetrazole induced changes in zebrafish behavior, neural activity and c-fos expression," *Neuroscience* 131(3):759-768.

Baraban S.C. et al. (Jun. 2007, e-published May 23, 2007). "A large-scale mutagenesis screen to identify seizure-resistant zebrafish," *Epilepsia* 48(6):1151-1157.

Baraban S.C. et al. (2013). "Drug screening in Scn1a zebrafish mutant identifies clemizole as a potential Dravet syndrome treatment," *Nat Commun* 4:2410.

Baxendale, S. et al. (Nov. 2012, e-published Jun. 21, 2012). "Identification of compounds with anti-convulsant properties in a zebrafish model of epileptic seizures," *Dis Model Meeh* 5(6):773-784.

Bays, H.E. (Nov. 2009). "Lorcaserin and adiposopathy: 5-HT2c agonism as a treatment for 'sick fat' and metabolic disease," *Expert Rev Cardiovasc Ther* 7(11):1429-1445.

Bender, A.C. et al. (Mar. 2012, e-published Feb. 16, 2012). "SCN1A mutations in Dravet syndrome: impact of interneuron dysfunction on neural networks and cognitive outcome," *Epilepsy Behav* 23(3):177-186.

Berghmans, S. et al. (Jun. 2007, e-published May 7, 2007). "Zebrafish offer the potential for a primary screen to identify a wide variety of potential anticonvulsants," *Epilepsy Res* 75(1):18-28.

Bialer, M. et al. (Jan. 2010). "Key factors in the discovery and development of new antiepileptic drugs," *Nat Rev Drug Discov* 9(1):68-82.

Blasiole, B. et al. (Dec. 2002). "Cloning, mapping, and developmental expression of a sixth zebrafish Na,K-ATPase alpha1 subunit gene (atp1a1a.5)," *Mech Dev* 119 Suppl 1:S211-214.

Borowicz, K.K. et al. (2012). "Trazodone reduces the anticonvulsant action of certain classical antiepileptics in the mouse maximal electroshock model," *Pharmacol Rep* 64(5):1136-1145.

Cao, D. et al. (Jul. 2012, e-publsihed May 11, 2012). "Efficacy of stiripentol in hyperthermia-induced seizures in a mouse model of Dravet syndrome." *Epilepsia* 53(7):1140-1145.

Cario, C.L. et al. (Aug. 1, 2011, e-published Jun. 6, 2011). "Automated measurement of zebrafish larval movement," *J Physiol* 589:3703-3708.

Catterall, W.A. et al. (Jun. 1, 2010, e-published Mar. 1, 2010). "NaV1.1 channels and epilepsy," *J Physiol* 588(Pt. 11):1849-1859.

CDC (Nov. 1997). Cardiac Valvulopathy Associated with Exposure to Fenfluramine or Dexfenfluramine: U.S. Department of Health and Human Services Interim Public Health Recommendations, *MMWR Weekly* 46(45):1061 -1066.

Ceulemans, B.P. et al. (Apr. 2004). "Clinical correlations of mutations in the SCN1A gene: from febrile seizures to severe myoclonic epilepsy in infancy," *Pediatric Neurol* 30(4):236-243.

Cheah, C.S. et al. (Sep. 4, 2012, e-published Aug. 20, 2012). "Specific deletion of NaV1.1 sodium channels in inhibitory interneurons causes seizures and premature death in a mouse model of Dravet syndrome," *PNAS USA* 109(36):14646-14651.

Chege, S. W. et al. (2012). "Expression and function of KCNQ channels in larval zebrafish," Dev. Neurobiol. 72, 186-198.

Chen, C. et al. (Apr. 21, 2004). "Mice lacking sodium channel beta1 subunits display defects in neuronal excitability, sodium channel expression, and nodal architecture," *J Neurosci* 24(16):4030-4042.

Database Accession No. Medline NLM7969960 (Nov. 1994). Epilsepsy and Sleep Apnea Syndrome, 1 page.

Database WPI Week 201549, AN 2015-38134E, 9 pages.

Delvecchio, C., et al., The zebrafish: a powerful platform for in vivo, HTS drug discovery. Assay Drug Dev. Technol. 9, 354-361 (2011).

De Toffol, B., et al., ESPERA study: Applicability of the new ILAE criteria for antiepileptic drug resistance of focal epilepsies in current clinical practice. Epilepsy Beh 25:166-169 (2012).

Devinsky, O. et al. (Nov. 1994). "Epilepsy and sleep apnea syndrome," *Neurology* 44(11):2060-2064.

Dravet, C. et al. (2005). "Severe myoclonic epilepsy in infancy: Dravet syndrome," Adv Neurol 95:71-102.

Einav, S. et al. J. S., Discovery of a hepatitis C target and its pharmacological inhibitors by microfluidic affinity analysis. Nat. Biotechnol. 26, 1019-1027 (2008).

(56) References Cited

OTHER PUBLICATIONS

Ellis, L. D. et al. Distinct modes of induced hyperactivity in zebrafish larvae. Brain Res. 1449, 46-59 (2012).
Finkelstein, M. et al. (Jan. 1960). "Some Aspects of the Pharmacology of Clemizole Hydrochloride," *Journal of the American Pharmaceutical Association* 49(1):18-22.
Fisher, R.S. et al. (Apr. 2014, e-published Apr. 14, 2014). "ILAE official report: a practical clinical definition of epilepsy," Epilepsia 55(4):475-482.
Gokul, C.G. et al. (Jan. 1, 2011). "A Study on Effect of Trazadone, Amoxapine and Venlafaxine on MES (Maximal Electroshock_ Induced Seizures in Albino Rates," *Pharmacologyonline* 3:214-221.
Gustafson, A. et al. (Sep. 2013). "Lorcaserin (Belviq) a Selective Serotonin $5\text{-HT}_{2c}$ Agonist in the Treatment of Obesity," Drug Forcast 38(9):525-534.
Hadra, R. et al. (Dec. 1956). "Quantitative assessment of motor function in cerebral palsy; evaluation of zoxazolamine (flexin), a new muscular relaxant drug," *Neurology* 6(12):843-852.
Han, S., et al., Autistic-like behaviour in Scnla$^{30/-}$ mice and rescue by enhanced GABA-mediated neurotransmission. Nature 489, 385-390 (2012).
Harkin, L.A. et al. The spectrum of SCN1 A-related infantile epileptic encephalopathies. Brain 130, 843-852 (2007).
Hortopan, G. A., et al., Spontaneous seizures and altered gene expression in GABA signaling pathways in a mind bomb mutant zebrafish. I Neurosci. 30, 13718-13728 (2010).
Hunt, R. F., et al. A novel zebrafish model of hyperthermia-induced seizures reveals a role for TRPV4 channels and NMDA-type glutamate receptors. Exp. Neurol. 237, 199-206 (2012).
Isaac, M. (2005). "Serotonergic 5-HT2C receptors as a potential therapeutic target for the design antiepileptic drugs," *Curr Top Med Chem* 5(1):59-67.
Jordan, C. et al., Cerebellar gene expression profiles of mouse models for Rett syndrome reveal novel MeCP2 targets. BMC Med Genet. 8, 36 (2007).
Jordan, J. et al. (Jun. 2014). "Cardiovascular effects of phentermine and topiramate: a new drug combination for the treatment of obesity," *J Hypertens* 32(6):1178-1188.
Kim, D. Y. et al. (Mar. 11, 2011, e-published Dec. 29, 2010). "Reduced sodium channel Na(v)1.1 levels in BACE1-null mice," *J. Biol. Chem.* 286(10):8106-8116.
Korff, C. et al. (Feb. 2007). "Dravet syndrome (severe myoclonic epilepsy in infancy): a retrospective study of 16 patients," *J Child Neurol* 22(2):185-194.
Lessman, C. A., The developing zebrafish (*Danio rerio*): a vertebrate model for high-throughput screening of chemical libraries. Birth Defects Res. Part C. Embryo Today 93, 268-280 2011).
Lopez, M., et al., Expression of the somatolactin β gene during zebrafish embryonic development. Gene Expr. Patterns 6, 156-161 (2006).
Loscher, W. et al. Modern antiepileptic drug development has failed to deliver: Ways out of the current dilemma. Epilepsia 52, 657-658 (2011).
Maj, J. et al. (1979). "Trazodone, a central serotonin antagonist and agonist," J Neural Transm 44(3):237-248.
Marcoli, M. et al. (Jun. 1998). "Trazodone is a potent agonist at 5-HT2C receptors mediating inhibition of the N-methyl-D-aspartate/ nitric oxide/cyclic GMP pathway in rat cerebellum," J Pharmacol Exp Ther 285(3):983-986.
Martin, M. S., et al., The voltage-gated sodium channel Scn8a is a genetic modifier of severe myoclonic epilepsy of infancy. Hum. Mol. Gen. 16, 2892-2899 (2007).
Miyata, I. et al. Seizure-modifying potential of histamine $H_1$ antagonists: a clinical observation. Pediatr. Int. 53, 706-708 (2011).
Mulley J. C., et al., SCN1A mutations and epilepsy. Hum. Mutat. 25, 535-542 (2005).
Noam, Y., et al., Towards an integrated view of HCN channel role in epilepsy. Curr. Opin. Neurobiol. 21, 873-879 (2011).

Novak, A. E., et al., Embryonic and larval expression of zebrafish voltage-gated sodium channel alpha-subunit genes. Dev. Dyn. 235, 1962-1973 (2006).
Oakley, J. C., et al., Temperature-and age-dependent seizures in a mouse model of severe myoclonic epilepsy in infancy. Proc. Natl. Acad. Sci. USA 106, 3994-3999 (2009).
Odagaki, Y. et al. (May 2005). "Trazodone and its active metabolite m-chlorophenylpiperazine as partial agonists at 5-HT1A receptors assessed by [35S]GTPgammaS binding," J Psychopharmacol 19(3):235-241.
Ogiwara, I., et al., Nav1.1 localizes to axons of parvalbumin-positive inhibitory interneurons: a circuit basis for epileptic seizures in mice carrying an Scnla gene mutation. I Neurosci. 27, 5903-5914 (2007).
Orban, G. et al. (Jul. 2014). "Role(s) of the 5-HT2C receptor in the development of maximal dentate activation in the hippocampus of anesthetized rats," *CNS Neurosci Ther* 20(7):651-661.
Orellana-Paucar, A. M., et al., Anticonvulsant activity of bisabolene sesquiterpenoids of *Curcuma longa* in zebrafish and mouse seizure models. Epilepsy Beh. 24, 14-22 (2012).
Pineda, E.A. et al. (Apr. 2012). "Interleukin-1β causes fluoxetine resistance in an animal model of epilepsy-associated depression," *Neurotherapeutics* 9(2):477-485.
Richter, J.M. et al. (Nov. 2014, e-published Aug. 19, 2014). "Clemizole hydrochloride is a novel and potent inhibitor of transient receptor potential channel TRPC5," *Mol Pharmacol* 86(5):514-521.
Rinkwitz, S., et al., Zebrafish: an integrative system for neurogenomics and neurosciences. Prog. Neurobiol. 93, 231-243 (2011).
Sakitama, K., The effects of centrally acting muscle relaxants on the intrathecal noradrenaline-induced facilitation of the flexor reflex mediated by group II afferent fibers in rats. Jpn. J Pharmacol. 63, 369-736 (1993).
Schoonheim, P. J. et al. Optogenetic localization and genetic perturbation of saccade-generating neurons in zebrafish. 1 Neurosci. 30, 7111-7120 (2010).
Schukla, A.P. et al. (2015, e-published Oct. 15, 2015). "Lorcaserin Hcl for the treatment of obesity," *Expert Opin Pharmacother* 16(16):2531-2538.
Sourbron, J. et al. (May 18, 2016, e-published Feb. 17, 2016). "Serotonergic Modulation as Effective Treatment for Dravet Syndrome in a Zebrafish Mutant Model," *ACS Chem Neurosci* 7(5):588-598.
Stafstrom, C.E. et al. (2015). Seizures and Epilepsy: An Overview for Neuroscientists; Cold Spring Harb Perpsect Med 2015;5:a022426.
Thomsen, W.J. et al. (May 2008, e-published Feb. 5, 2008). "Lorcaserin, a novel selective human 5-hydroxytryptamine2C agonist: in vitro and in vivo pharmacological characterization," *J Pharmacol Exp Ther* 325(2):577-587.
Tongiorgi, E., et al., Brain-derived neurotrophic factor mRNA and protein are targeted to discrete dendritic laminas by events that trigger epileptogenesis. J. Neurosci. 24, 6842-6852 (2004).
Warter, J.M.et al. (1990). "Immediate effects of 14 non MAOI antidepressants in rats with spontaneous petit mal-like seizures," *Prog Neuropsychopharmacol Biol Psychiatry* 14(2):261-270.
Winter, M. J., et al., Validation of a larval zebrafish locomotor assay for assessing the seizure liability of early-stage development drugs. J Pharm. Tax. Methods 5, 176-187 (2008).
Wolff, M. et al. (2006). "Severe myoclonic epilepsy of infants (Dravet syndrome): natural history and neuropsychological findings," *Epilepsia* 47 Suppl 2:45-48.
Yamada, K. et al. The effect of antihistamines on seizures induced by increasing-current electroshocks: ketotifen, but not olopatadine, promotes the seizures in infant rats. Biol. Pharm. Bull. 35, 693-697 (2012).
Yu, F. H. et al. (Sep. 2006, e-published Aug. 20, 2006). "Reduced sodium current in GABAergic interneurons in a mouse model of severe myoclonic epilepsy in infancy," *Nat. Neurosci.* 9(9):1142-1149.
European Search Report dated Aug. 31, 2018, for EP Application No. 16756282.6, filed Feb. 24, 2016, 11 pages.
Extended European Search Report dated Nov. 21, 2018, for EP Application No. 16756282.6, filed Feb. 24, 2016, 24 pages.

(56) References Cited

OTHER PUBLICATIONS

International Search Report dated May 3, 2016, for PCT Application No. PCT/US2016/019368, filed Feb. 24, 2016, 3 pages.
Written Opinion dated May 3, 2016, for PCT Application No. PCT/US2016/019368, filed Feb. 24, 2016, 10 pages.
Anonymous (Jan. 1, 2019). Lennox-Gastaut Syndrome, Rare diseases located at https://rarediseases.org/rare-diseases/lennox-gastaut-syndrome/, last visited Jun. 12, 2020, 15 pages.
Griffin, A. et al. (Mar. 1, 2017). Clemizole and Modulators of Serotonin Signalling Suppress Seizures in Dravet Syndrome, Brain 140(3):669-683.
Kauppila, L.A. et al. (2018). "Trazodone: A New Antiepileptic Drug for Dravet Syndrome?" International Journal of Epilepsy 5(2):99-103.
Smith, S.R. et al. (Mar. 2009, e-published Dec. 4, 2008). "Lorcaserin (APD356), a Selective 5-HT(2C) Agonist, Reduces BodyWeight in Obese Men and Women," Obesity 7(3):494-503.
Tolete, P. et al. (Oct. 30, 2018, e-published Sep. 26, 2018). "Lorcaserin Therapy for Severe Epilepsy of Childhood Onset: A Case Series," Neurology 91(18):837-839.
Bardai, A. et al. (2012, e-published Aug. 14, 2012). Epilepsy is a risk factor for sudden cardiac arrest in the general population, *PLoS One* 7(8):e42749, pp. 1-5.

\* cited by examiner

FIG. 11

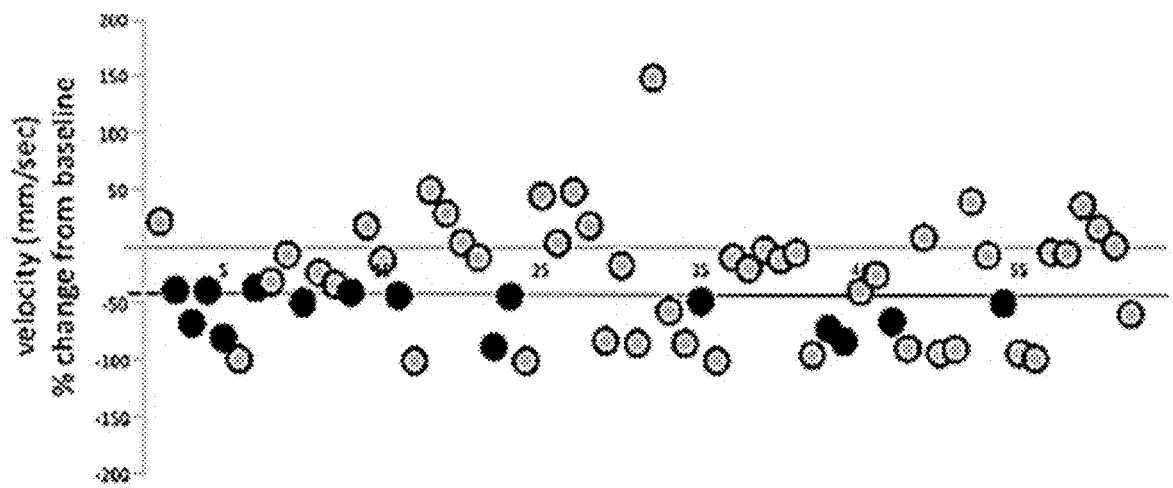

| Mosapride Citrate | ziprasidone HCl | PRX-08066 Maleic acid |
| sumatriptan succinate | TCB-2 | trazodone HCl |
| naratriptan | Iloperidone | BMY 7378 |
| rizatriptan benzoate | Risperidone | Lamotrigine |
| zolmitriptan | Tropisetron HCl | atomoxetine HCl |
| Aripiprazole | Ondansetron | Amitriptyline HCl |
| urapidil HCl | Azasetron HCl | Loxapine Succinate |
| almotriptan HCl | Blonanserin | Vortioxetine (Lu AA21004) HBr |
| WAY-100635 Maleate | Ketanserin | Tianeptine sodium |
| BRL-54443 | Clozapine | Fluoxetine HCl |
| Prucalopride | Olanzapine | Fluvoxamine maleate |
| eletriptan HBr | Clomipramine HCl | venlafaxine |
| lorcaserin HCl | LY310762 | Dapoxetine HCl |
| Serotonin HCl | BRL-15572 | Mirtazapine |
| Prucalopride Succinate | RS-127445 | Duloxetine HCl |
| buspirone HCl | SB269970 HCl | Paroxetine HCl |
| Agomelatine | SB271046 | Escitalopram Oxalate |
| Latrepirdine | VUF 10166 | Desvenlafaxine Succinate |
| Asenapine | SB742457 | Desvenlafaxine |
| Granisetron HCl | Palonosetron HCl | Vilazodone HCl |
| Ondansetron HCl | Sertraline HCl | |

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 1

Phe Met Ile Leu Leu
1               5

<210> SEQ ID NO 2
<211> LENGTH: 15
<212> TYPE: DNA
```

```
<213> ORGANISM: Artificial sequence
<220> FEATURE:
<223> OTHER INFORMATION: Synthetic polynucleotide

<400> SEQUENCE: 2
ttcatgattt tactc                                                15

<210> SEQ ID NO 3
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 3

Phe Arg Ile Leu Leu
1               5

<210> SEQ ID NO 4
<211> LENGTH: 15
<212> TYPE: DNA
<213> ORGANISM: Artificial sequence
<220> FEATURE:
<223> OTHER INFORMATION: Synthetic polynucleotide

<400> SEQUENCE: 4
ttcaggattt tactc                                                15
```

5HT AGONISTS FOR TREATING DISORDERS

CROSS-REFERENCE TO RELATED APPLICATIONS

This application is a division of U.S. application Ser. No. 15/552,784 filed Aug. 22, 2017, now U.S. Pat. No. 10,874,643, which is a National Stage Entry of Application No. PCT/US2016/019368 filed Feb. 24, 2016, which claims priority to U.S. Application No. 62/120,726 filed Feb. 25, 2015, the disclosures of which are incorporated by reference herein in their entireties.

REFERENCE TO A "SEQUENCE LISTING," A TABLE, OR A COMPUTER PROGRAM LISTING APPENDIX SUBMITTED AS AN ASCII FILE

The Sequence Listing written in file 048536-557D01US SequenceListing_ST25.txt, created Feb. 5, 2021, 1,134 bytes, machine format IBM-PC, MS Windows operating system, is hereby incorporated by reference.

STATEMENT AS TO RIGHTS TO INVENTIONS MADE UNDER FEDERALLY SPONSORED RESEARCH AND DEVELOPMENT

This invention was made with Government support under grant number R01 NS079214 awarded by the National Institutes of Health. The Government has certain rights in the invention.

FIELD OF THE INVENTION

The disclosure provides methods for treating an epilepsy disorder using a 5HT receptor agonist, or a pharmaceutically acceptable salt thereof.

BACKGROUND OF THE INVENTION

Dravet syndrome (DS) is a catastrophic pediatric epilepsy with severe intellectual disability, impaired social development and persistent drug-resistant seizures. One of its primary causes is mutations in Nav1.1 (SCN1A), a voltage-gated sodium channel. Seizures experienced by those with DS and other epilepsy disorders are inadequately managed using available antiepileptic drugs (AEDs) and children with DS are poor candidates for neurosurgical resection. Thus there is a need in the art for epilepsy treatment options, especially those for DS and related catastrophic pediatric epilepsies. Provided herein are solutions to these problems and other problems in the art.

BRIEF SUMMARY OF THE INVENTION

Provided herein, inter alia, are methods of treating epilepsy disorders using a 5HT agonist, or a pharmaceutically acceptable salt thereof. In one aspect the method includes administering to a subject in need thereof, a therapeutically effective amount of a 5HT agonist, a 5HT agonist analog, or a pharmaceutically acceptable salt thereof. In another aspect the method includes administering to a subject in need thereof, a pharmaceutical composition that includes a therapeutically effective amount of a 5HT agonist, a 5HT agonist analog, or a pharmaceutically acceptable salt thereof. Further provided herein are pharmaceutical compositions for treating epilepsy disorders.

According to an aspect of the disclosure, a method of treating an epilepsy disorder may involve administering to a patient having an epilepsy disorder a therapeutically effective amount of a 5HT receptor agonist, or a pharmaceutically acceptable salt thereof.

In an exemplary embodiment, the 5HT agonist may be a $5HT_2A$ receptor agonist or a $5HT_{2B}$ receptor agonist. In some exemplary embodiment, it is contemplated that the 5HT agonist may be any one or more of ACP-104, ACP-106, AR-116081, AR-116082, ATHX-105, belladonna in combination with ergotamine tartrate, BW 723C86, Cisapride, Ciza-MPS, Cizap, Cizap-Mps, CSC-500 Series, DOI or salt thereof (e.g. HCl), Ergotamine Tartrate and Caffeine, Esorid MPS, flibanserin, Ikaran L.P., Manotac Plus, Migril, Mirtazapina Rimafar, mirtazapine, Naratriptan, nelotanserin, norfenfluramine, Normagut Tab, nefazodone hydrochloride, OSU-6162, Pridofin, Sensiflu, PRX-00933, RP-5063, Small Molecule to Agonize $5-HT_{2A}$ for Inflammatory Diseases, Small Molecules to Agonize $5-HT_{2C}$ for Schizophrenia and Obesity, Small Molecules to Agonize $5-HT_{2C}$ Receptor for Obesity, Small Molecules to Target $5-HT_{2C}$ and $5-HT_6$ Receptor for Schizophrenia, Small Molecules to Modulate $5HT_2$ for CNS and Metabolic Disorders, TGBA-01AD, trazodone hydrochloride, temanogrel hydrochloride, vabicaserin hydrochloride, Virdex, VR-1065, ziprasidone hydrochloride, and/or Ziprasidon-Sigillata.

In some exemplary embodiments, it is contemplated that the 5HT receptor agonist is not clemizole or fenfluramine. In some exemplary embodiments, it is further contemplated that the 5HT receptor agonist is not acetazolamide, benzodiazepine (diazepam; clobazam), cannabadiol, carbamazepine, clemizole, ethosuximide, felbamate, fenfluramine, fluoxetine, gabapentin, ganaxolone, lacosamide, lamotrigine, levetiracetam, nitrazepam, oxcarbazepine, perampanel, phenytoin, phenobarbital, piracetam, potassium bromide, pregabalin, primidone, retigabine, rufinamide, stiripentol, tiagabine, topiramate, valproic acid, verapamil, vigabatrin, and/or zonisamide.

In an exemplary embodiment, the 5HT receptor agonist binds directly to a 5HT receptor. In an exemplary embodiment, the 5HT receptor agonist specifically activates a 5HT receptor.

In an exemplary embodiment, the 5HT receptor agonist provides increased activity mediated by $5HT_{2A}$ receptor or $5HT_{2B}$ receptor with equivalent or reduced activity mediated through $5HT_{2c}$ receptor.

In an exemplary embodiment, the 5HT receptor agonist is a dual $5HT_{2A}$ receptor and $5HT_{2B}$receptor agonist.

In an exemplary embodiment, the 5HT receptor agonist is not a serotonin reuptake inhibitor.

In an exemplary embodiment, the 5HT receptor agonist does not significantly bind to or modulate the activity of at least one of $5HT_{1A}$, $5HT_{1B}$, $5HT_{1D}$, $5HT_{2C}$, $5HT_3$, $5HT_4$ (e.g. $5HT_{4e}$), $5HT_6$, $5HT_7$, NPY Y1 receptor, L-type Ca channel, N-type Ca channel, SK-Ca channel, GABA-gated Cl channel, GABA transporter, GABA-A1 receptor, GABA-B1b receptor, Na channel, 5HT transporter, CB1 receptor, CB2 receptor, BZD or Estrogen ER alpha.

In an exemplary embodiment, the 5HT receptor agonist is any one or more of flibanserin, 2,5-dimethoxy-4-Iodoamphetamine monohydrochloride (DOI HCl), norfenfluramine or BW 723C86.

In an exemplary embodiment, the epilepsy disorder is Dravet Syndrome, Lennox-Gastaut Syndrome, infantile spasm, or Ohtahara Syndrome. In an exemplary embodiment, the epilepsy disorder is Dravet Syndrome. In an exemplary embodiment, the epilepsy disorder is a pediatric epilepsy disorder.

In an exemplary embodiment, the subject has a cardiovascular disease.

In an exemplary embodiment, the subject is resistant to treatment with a serotonin reuptake inhibitor.

In an exemplary embodiment, the subject is susceptible to side effects when administered a serotonin reuptake inhibitor. In an exemplary embodiment, the serotonin reuptake inhibitor is fenfluramine.

In an exemplary embodiment, the subject has a ketogenic diet.

In an exemplary embodiment, the 5HT receptor agonist inhibits compulsive behaviors or electrographic seizures in an epilepsy subject, an Alzheimer's disease subject, an autism subject, or a Parkinson's disease subject.

In an exemplary embodiment, the 5HT receptor agonist reduces the incidence of unprovoked seizures in said subject when compared to the absence of said 5HT receptor agonist.

In an exemplary embodiment, the administration of said 5HT receptor agonist reduces or prevents myoclonus seizures or status epilepticus in said subject when compared to the absence of 5HT receptor agonist.

In an exemplary embodiment, the 5HT receptor agonist is administered to said subject at an amount of about 0.1 mg to about 1000 mg per kg body weight.

In an exemplary embodiment, the 5HT receptor agonist is administered to said subject in a daily dose of about 0.1 mg to about 1000 mg per kg body weight to said subject.

In an exemplary embodiment, the 5HT receptor agonist is co-administered with an anti-epileptic drug (AED) In an exemplary embodiment, the 5HT receptor agonist is an adjunctive therapy with an anti-epileptic drug (AED). In an exemplary embodiment, the AED is acetazolamide, benzodiazepine, cannabadiols, carbamazepine, clobazam, clonazepam, eslicarbazepine acetate, ethosuximide, ethotoin, felbamate, fenfluramine, fosphenytoin, gabapentin, ganaxolone, huperzine A, lacosamide, lamotrigine, levetiracetam, nitrazepam, oxcarbazepine, perampanel, piracetam, phenobarbital, phenytoin, potassium bromide, pregabalin, primidone, retigabine, rufinamide, valproic acid, sodium valproate, stiripentol, tiagabine, topiramate, vigabatrin, or zonisamide. In an exemplary embodiment, the AED is valproic acid, sodium valproate, clonazepam, ethosuximide, felbamate, gabapentin, carbamazepine, oxcarbazepine, lamotrigine, levetiracetam, benzodiazepine, phenobarbital, pregabalin, primidone, tiagabine, topiramate, potassium bromide, phenytoin, stiripentol, vigabatrin, or zonisamide. In an exemplary embodiment, the AED is valproic acid, sodium valproate, gabapentin, topiramate, carbamazepine, oxcarbazepine, or vigabatrin.

In an exemplary embodiment, the AED is not a topiramate.

In an exemplary embodiment, the AED is not fenfluramine.

In an exemplary embodiment, the AED is administered simultaneously with or sequentially with said 5HT receptor agonist.

In another aspect, the disclosure provides a method of treating an epilepsy disorder, said method comprising administering to a subject in need thereof a therapeutically effective amount of a 5HT receptor agonist, or a pharmaceutically acceptable salt thereof, wherein said subject has a cardiovascular disease, is resistant to treatment with a serotonin reuptake inhibitor, or is susceptible to side effects when administered a serotonin reuptake inhibitor.

In an exemplary embodiment, the 5HT receptor agonist is a $5HT_{2A}$ receptor agonist or a $5HT_{2B}$ receptor agonist. In an exemplary embodiment, the 5HT receptor agonist is clemizole, a clemizole analog, or a pharmaceutically acceptable salt thereof. In an exemplary embodiment, the pharmaceutically acceptable salt is clemizole HCl.

In embodiments, the 5HT receptor agonist is sumatriptan, naratriptap, rizatriptan, zolmitriptan, urapidil, BRL-54443 (3-(1-methylpiperidin-4-yl)-1H-indol-5-01), lorcaserin, buspirone, ziprasidone, TCB-2 ((4-Bromo-3,6-dimethoxybenzocyclobuten-1-yl)methylamine hydrobromide), BRL-15572 (3-(4-(4-chlorophenyl)piperazin-1-yl)-1,1-diphenyl-2-propanol), trazodone, BMY 7378 (8-(2-[4-(2-methoxyphenyl)-1-piperazinyl]ethyl)-8-azaspiro[4.5]decane-7,9-dione), atomoxetine, and venlafaxine. In embodiments, the 5HT receptor agonist is sumatriptan. In embodiments, the 5HT receptor agonist is naratriptap. In embodiments, the 5HT receptor agonist is rizatriptan. In embodiments, the 5HT receptor agonist is zolmitriptan. In embodiments, the 5HT receptor agonist is urapidil. In embodiments, the 5HT receptor agonist is
BRL-54443 (3-(1-methylpiperidin-4-yl)-1H-indol-5-ol). In embodiments, the 5HT receptor agonist is lorcaserin. In embodiments, the 5HT receptor agonist is buspirone. In embodiments, the 5HT receptor agonist is ziprasidone. In embodiments, the 5HT receptor agonist is TCB-2 ((4-Bromo-3,6-dimethoxybenzocyclobuten-1-yl)methylamine hydrobromide). In embodiments, the 5HT receptor agonist is BRL-15572 (3-(4-(4-chlorophenyl)piperazin-1-yl)-1,1-diphenyl-2-propanol). In embodiments, the 5HT receptor agonist is trazodone. In embodiments, the 5HT receptor agonist is BMY 7378 (8-(2-[4-(2-methoxyphenyl)-1-piperazinyl]ethyl)-8-azaspiro[4.5]decane-7,9-dione). In embodiments, the 5HT receptor agonist is atomoxetine. In embodiments, the 5HT receptor agonist is venlafaxine.

In embodiments, the 5HT receptor agonist is trazodone or a pharmaceutically acceptable salt thereof.

In an exemplary embodiment, the clemizole, said clemizole analog, or said pharmaceutically acceptable salt thereof forms part of a pharmaceutical composition. In an exemplary embodiment, the pharmaceutical composition further comprises a pharmaceutically acceptable excipient. In an exemplary embodiment, the pharmaceutical composition comprises a therapeutically effective amount of clemizole, said clemizole analog, or said pharmaceutically acceptable salt thereof.

In an exemplary embodiment, the pharmaceutical composition is co-administered with an anti-epileptic drug (AED) In an exemplary embodiment, the pharmaceutical composition comprises clemizole, said clemizole analog, or said pharmaceutically acceptable salt thereof and an AED In an exemplary embodiment, the 5HT receptor agonist is not fenfluramine. In an exemplary embodiment, the 5HT receptor agonist binds directly to a 5HT receptor.

In an exemplary embodiment, the 5HT receptor agonist specifically activates a 5HT receptor. In an exemplary embodiment, the 5HT receptor agonist provides increased activity mediated by $5HT_{2A}$ receptor or $5HT_{2B}$ receptor with equivalent or reduced activity mediated through $5HT_{2c}$ receptor. In an exemplary embodiment, the 5HT receptor agonist is a dual $5HT_{2A}$ receptor and $5HT_{2B}$ receptor agonist.

In an exemplary embodiment, the 5HT receptor agonist is not a serotonin reuptake inhibitor.

In an exemplary embodiment, the 5HT receptor agonist does not significantly bind to at least one of $5HT_{1A}$, $5HT_{1B}$, $5HT_{1D}$, $5HT_{2C}$, $5HT_3$, $5HT_4$ (e.g. $5HT_{4e}$), $5HT_6$, $5HT_7$, NPY Y1 receptor, L-type Ca channel, N-type Ca channel, SK-Ca channel, GABA-gated Cl channel, GABA transporter, GABA-A1 receptor, GABA-B1b receptor, Na channel, 5HT transporter, CB1 receptor, CB2 receptor, BZD or Estrogen ER alpha.

In another aspect, the disclosure provides a method of modulating activity of a 5HT receptor comprising contacting a 5HT receptor with clemizole, a clemizole analog, or a pharmaceutically acceptable salt thereof.

In an exemplary embodiment, the modulating is activating.

In an exemplary embodiment, the 5HT receptor is a $5HT_{2A}$ receptor or a $5HT_{2B}$ receptor.

In another aspect, the disclosure provides a method of treating a disease or disorder caused by a deficiency of serotonin in the brain or under activity of one or more 5HT receptors comprising administering to a subject in need thereof a therapeutically effective amount of clemizole, a clemizole analog, or a pharmaceutically acceptable salt thereof.

In an exemplary embodiment, the disease or disorder is not epilepsy.

In an exemplary embodiment, the disease or disorder is not Dravet Syndrome.

In an exemplary embodiment, the disease or disorder is selected from the group consisting of migraine, Fragile X syndrome, Prader-Willi syndrome, schizophrenia, depression, Alzheimer's disease, autism, neuropathic pain, Parkinson's disease, irritable bowel disorder, and dementia.

In one aspect there is provided a pharmaceutical composition that includes clemizole, a clemizole analog, or a pharmaceutically acceptable salt thereof for use in treating a disease or disorder caused by a deficiency of serotonin in the brain or under activity of one or more 5HT receptors.

In embodiments of an aspect above, the 5HT receptor agonist does not significantly bind to or modulate (e.g. inhibit) the activity of at least one of 5HT1A, 5HT1B, 5HT1D, 5HT3, 5HT4e, GABAA1, $GABAB_{(1b)}$, BZD. CB', CB2, GABA-gated Cl channel, SK-Ca channel or GABA transporter. In embodiments, the 5HT receptor agonist does not significantly bind to or modulate (e.g. inhibit) the activity of 5HT1A, 5HT1B, 5HT1D, 5HT3, 5HT4e, GABAA1, $GABAB_{(1b)}$, BZD. $CB_1$, $CB_2$, GABA-gated Cl channel, SK-Ca channel and GABA transporter.

In embodiments of an aspect above, the 5HT receptor agonist modulates a target less than about 50% relative to a reference modulator (e.g. a natural or known modulator as commonly used in the art). In embodiments, the 5HT receptor agonist modulates a target less than about 40% relative to a reference modulator (e.g. a natural or known modulator as commonly used in the art). In embodiments, the 5HT receptor agonist modulates a target less than about 30% relative to a reference modulator (e.g. a natural or known modulator as commonly used in the art). In embodiments, the 5HT receptor agonist modulates a target less than about 20% relative to a reference modulator (e.g. a natural or known modulator as commonly used in the art). In embodiments, the 5HT receptor agonist modulates a target less than about 10% relative to a reference modulator (e.g. a natural or known modulator as commonly used in the art).

In embodiments of an aspect above, the 5HT receptor agonist does not significantly modulate the activity when the 5HT receptor agonist fails to modulate (e.g. inhibit) a target less than about 50% relative to a reference inhibitor (e.g. a natural or known inhibitor as commonly used in the art). In embodiments, the 5HT receptor agonist does not significantly modulate the activity when the 5HT receptor agonist fails to modulate (e.g. inhibit) a target less than about 40% relative to a reference inhibitor (e.g. a natural or known inhibitor as commonly used in the art). In embodiments, the 5HT receptor agonist does not significantly modulate the activity when the 5HT receptor agonist fails to modulate (e.g. inhibit) a target less than about 30% relative to a reference inhibitor (e.g. a natural or known inhibitor as commonly used in the art). In embodiments, the 5HT receptor agonist does not significantly modulate the activity when the 5HT receptor agonist fails to modulate (e.g. inhibit) a target less than about 20% relative to a reference inhibitor (e.g. a natural or known inhibitor as commonly used in the art). In embodiments, the 5HT receptor agonist does not significantly modulate the activity when the 5HT receptor agonist fails to modulate (e.g. inhibit) a target less than about 10% relative to a reference inhibitor (e.g. a natural or known inhibitor as commonly used in the art). In embodiments, the 5HT receptor agonist does not significantly modulate the activity when the 5HT receptor agonist fails to modulate (e.g. inhibit) a target less than about 5% relative to a reference inhibitor (e.g. a natural or known inhibitor as commonly used in the art).

BRIEF DESCRIPTION OF THE DRAWINGS

(FIG. 1A) Sequencing confirmed a T-to-G mutation in scn1Lab mutant cDNA. (FIG. 1B) Verification of reduced expression in scn1Lab mutants compared to sibling controls at 3, 5 and 7 dpf using qPCR. Data presented as mean±S.E.M; *significance taken as p<0.05 student's t-test. Data were normalized to internal reference gene β-actin. Values represent averages from five independent biological samples (1 sample=10 pooled larvae) for each of the 3 developmental stages. Data presented as mean±S.E.M; *significance taken as p<0.05 student's t-test. (FIG. 1C) Relative expression of scn8aa and scn8ab in $Na_v1.1$ mutants (n=5) and sibling controls (n=5) at 5 dpf. Data presented as in B. (FIG. 1D) Whole-mount in situ hybridization for scn1Lab in larval zebrafish at 3, 5 and 7 dpf. Wild-type larvae are shown in lateral views; expression is shown in dark purple. Scn1Laa expression at 3 dpf is shown for comparison. Heart indicated by arrowheads in 5 and 7 dpf panels. (FIG. 1E) Dorsal view of scb1Laa expression at 3 dpf; note prominent expression in regions corresponding to the larval zebrafish CNS. Abbreviations: Tel, telencephalon; TeO, optic tectum; Cb, cerebellum. Scale bars=0.35 mm in D, 0.2 mm in E.

(FIG. 2A) Heat maps depicting the expression of genes differentially expressed between scn1Lab mutant and sibling control larvae at 5 dpf. Rows represent individual genes. Columns represent different larvae. Genes that are highly expressed in scn1Lab mutants relative to controls are as shown. (FIG. 2B) MA plot of normalized microarray data for all 44,000 genes. The log-ratio M and the mean fluorescence intensity A were calculated as the averages for all replicates. (FIG. 2C) A list of the top 30 genes showing the greatest differences in expression between scn1Lab mutants and sibling controls.

(FIG. 3A) Comparison of the gene expression fold changes obtained by microarray analysis (array) and real-time qPCR analysis. The y-axis represents the average fold change in gene expression of each gene from zebrafish at 5 dpf. The x-axis represents different genes. (FIG. 3B) qPCR analysis of three genes involved in epileptogenesis. The relative gene expression is presented as log$_2$ ratios to the least abundant transcript (log$_2\Delta\Delta$ct). Data were normalized to internal reference gene β-actin. Values represent averages from five independent biological samples (1 sample 10 pooled larvae). Bars indicate S.E.M; *p<0.05 t-test. (FIG. 3C) Gene ontology classification of differentially expressed genes detected in scn1Lab mutants at 5 dpf (p<0.05 ANOVA one-way and fold changes>1.5). Biological processes representing at least 5 gene annotations in at least one category are displayed.

(FIG. 4A) Immobilized and agar- embedded zebrafish larvae are shown. Images were obtained using a 4× objective and 2× magnifier on an Olympus upright microscope during forebrain electrophysiological recordings in sibling control (FIG. 4A, left) and scn1Lab mutant (FIG. 4A, middle) larvae at 5 dpf. Note the dark pigmentation for mutants. Recording electrodes can be seen in panels A1-2 and the approximate site of the recording electrode tip in the forebrain (red circle) is shown using a representative HuC: GFP labeled larvae in FIG. 4A, right. Scale bar: 100 μm. (FIG. 4B) Sample locomotion tracking plot for sibling control (B, left) and scn1Lab mutant (FIG. 4B, right) larvae at 5 dpf. (FIG. 4C) Representative 10 min recording epochs obtained in the forebrain of paralyzed, immobilized and agar-embedded scn1Lab mutant larvae between 3 and 7 dpf. Note the presence of small and large amplitude spontaneous burst discharge; additional temporal expansions of seizure activity. A representative recording, under identical recording conditions, from a sibling control larvae at 5 dpf is also shown. Scale bar: 2 mV; 30 sec.

(FIG. 5A) Heat map showing the response to nine different AEDs. Each column represents the percent change in burst frequency (baseline–drug/baseline× 100) for one individual zebrafish mutant. Drugs that inhibit seizure events are shown in dark blue. All drugs were tested at a concentration of 1 mM. Note in some trials carbamazepine and vigabatrin increased burst frequency over the initial baseline levels. (FIG. 5B) Plot of the mean change in burst frequency and standard error for the data shown in the heat map. Paired t-test or Wilcoxon signed rank sum test for data that failed the normality test showed significance as follows: diazepam (p=0.002; n=7), potassium bromide (p=0.016; n=7), stiripentol (p=0.024; n=7), and valproate (p=0.004; n=7). (FIG. 5C) Plot of the burst duration for all trials shown in FIG. 5A. Data is presented as the mean±S.E.M. for electrographic seizure events at baseline (black bars) and after drug exposure (white bars). Inset shows a representative 2 min recording during the stiripentol trial; scale bars: large trace 1 mV, 1 sec; small trace, 1 mV, 100 msec. (FIG. 5D) Plot of the fractional time spent seizing for all trials shown in FIG. 5A. Data is presented as the mean±S.E.M. for electrographic seizure events at baseline (black bars) and after drug exposure (white bars). Student's t-test or Mann-Whitney-Rank sum test for data that failed the normality test showed significance as follows: diazepam (p=0.001; n=7); potassium bromide (p=0.043; n=7); stiripentol (p=0.007; n=7) and valproate (p=0.007; n=7 (FIG. 5E) Locomotion tracking plots for 10 individual mutant larvae raised in embryo media (top row) or the ketogenic diet for 48 hr. Plots show swim velocity and locomotion tracks with darker colors indicative of higher velocities; 10 min trials are shown. (FIG. 5F) Representative 10 min extracellular recording epochs from the same fish shown in FIG. 5E; representative examples are indicated by an * in the locomotion plots. Scale bar: 1 mV, 30 sec. Inset shows burst at higher temporal resolution (indicated by #); scale bar: 1 mV, 100 msec.

(FIG. 6A) Box plot of mean velocity (in mm/sec) for two consecutive recordings of mutant larvae in embryo media. The experiments were performed by first placing the mutant larvae in embryo media and obtaining a baseline locomotion response, embryo media was then replaced with new embryo media (to mimic the procedure used for test compounds) and a second locomotion response was obtained. The percent change in velocity from baseline (recording #1) vs. experimental (recording #2) is shown. In the boxplot, the bottom and top of the box represent the 25th percentile and the 75th percentile, respectively. The line across the box represents the median value, and the vertical lines encompass the entire range of values. This plot represents normal changes in tracking activity in the absence of a drug challenge. (FIG. 6B) Plot of the effect of eleven known antiepileptic drugs on locomotor seizure behavior in scn1Lab mutants at 5 dpf. Phenotype-based assay was performed in a 96-well format (for example, see panel 5C1). Bars represent the percent change in mean velocity comparing a baseline recording of mutant seizure activity with the same mutant after a drug application. For all drug studies 6-12 fish were used per experiment. Drugs were tested at a concentration of 1 mM; diazepam (Dzp; p<0.001), carbamazepine (Carb, p=0.024), ganaxolone (Gan; p=0.003), stiripentol (Stp; p=0.001), valproate (Vpa, p=0.026) and a 48 hr exposure to the ketogenic diet (KD; p=0.003) reduced seizure activity, measured as a change in velocity, by more than 34% (dotted line in FIG. 6B; represents a fold-change greater than the standard deviation in control recordings). Acetazolamide (Acet, p<0.001) and ethosuximide (Etx; p=0.250) increased seizure behavior; levetiracetam (Lev; p=0.243), and lamotrigine (Ltg; p=0.058) had no effect. (FIG. 6C) Plot of locomotor seizure behavior for scn1Laab mutants at 5 dpf for the 320 compounds tested. Colored circles represent positive hits; compounds that decreased activity by 100% were generally toxic; 6-12 fish per trial. Arrowhead denotes the first clemizole trial. Note some compounds increased seizure activity, as expected. (FIG. 6D) Plot of drug re-trials on separate clutches of scn1Lab mutants at 5 dpf; 100 μM per drug; 10 fish per trial. Abbreviations: Clem, clemizole; Clem+PTZ, clemizole+15 mM PTZ; Clorg, clorgiline; Tolp, tolperisone; Zox, zoxazolamine. Effect of acute clemizole on PTZ-induced seizure behavior is shown for wild-type larvae. Bars represent mean±S.E.M. For panels B and D: Student's paired t-test or Mann-Whitney Rank Sum test with significance set at p=0.01 (*) or p<0.001 (**). (FIG. 6E) Sample electrophysiology recordings from scn1Lab mutants exposed to clemizole first in the locomotion assay (panel D) and then monitored using a forebrain extracellular recording electrode (top trace; ictal-like burst shown in inset). Similar traces are shown for an un-treated Na$_v$1.1 mutant (middle trace) and a mutant treated with zoxazolamine (bottom trace). Analysis of bursting for un-treated mutants (n=3): burst frequency=1.5±0.3 bursts/min; burst duration=926±414 msec; fractional time spent seizing=0.73±0.17% vs. clemizole-treated mutants (n=7): burst frequency=0.2±0.01 bursts/min; burst duration=154±127 msec; fractional time spent seizing=0.03±0.02%; p=0.001 for all comparisons, Kruskal-Wallis ANOVA with a Dunn's pairwise multiple comparison test). Scale bars: large trace 0.5 mV, 10 s; inset 0.5 mV, 100 msec.

(FIG. 7A) Representative 10 min recording epochs obtained in the forebrain of paralyzed, immobilized and agar-embedded scn1Laa mutant larvae at 6 dpf. Note the presence of small and large amplitude spontaneous burst discharge. (FIG. 7B) Locomotion tracking plots for 10 individual mutant and wild-type sibling larvae. Plots show swim velocity and locomotion tracks with darker colors indicative of higher velocities; 10 min trials are shown. Seizures were scored on a staging system described in Baraban et al. (Neuroscience 2005). S0, little or no swim activity; S1, increased locomotion; S2 whirlpool like swim activity and S3; full body convulsions with rapid swimming events and loss of posture. (FIG. 7C) Box plot of mean velocity (in mm/sec) for 96 zebrafish with fish sorted into putative scn1Laa and sibling control pools based on seizure stages described above. The experiments were performed by first placing the mutant larvae in embryo media and obtaining a baseline locomotion response, embryo media was then replaced with new embryo media and a second locomotion response was obtained. The percent change in velocity from baseline (recording #1) vs. experimental (recording #2) is shown. In the boxplot, the bottom and top of the box represent the 25th percentile and the 75th percentile, respectively. The line across the box represents the median value, and the vertical lines encompass the entire range of values. Plots are shown for all 96 fish (left), putative scn1Laa zebrafish (middle) and sibling controls (left). Subsequent PCR analysis was done to confirm mutant and control pools. (FIG. 7D) Plot of the effect of stiripentol (Stp), diazepam (Dzp), clemizole (Clem) and lamotrigine (Ltg) on locomotor seizure behavior in scn1Laa mutants at 5 dpf. Mean velocity is shown before and after application of a drug. N=7 fish per drug. Bars represent mean±S.E.M. Student's paired t-test or Mann-Whitney Rank Sum test with significance set at p=0.01 (*) or p<0.001 (**).

FIG. 11: 5HT library screen. Plot of locomotor seizure behavior for scn1Lab mutants at 5 dpf for the 62 compounds tested. Threshold for inhibition of seizure activity (positive hits) was set as a reduction in mean swim velocity≥38%; threshold for a proconvulsant or hyperexcitable effect was set at as an increase in mean swim velocity≥44% (green dashed lines). Compounds were tested at a concentration of 250 µM and 6 fish per drug. Compound list is shown below with positive hits indicated in grey (on chart) or black circles (in plot).

FIG. 12A. Plot of the change in mean velocity for scn1Lab mutants at 5 dpf exposed to different concentrations of trazodone for 30 min (black bars) or 90 (gray bars) drug exposure periods. Threshold for inhibition of seizure activity (positive hits) was set as a reduction in mean swim velocity≥40%. Trazodone was toxic at 750 µM (hashed lines). Compounds were tested at 6 fish per drug. FIG. 12B. Sample EEG traces for scn1Lab mutant larvae exposed to trazodone (suppression of epileptic seizure events) or a control drug, MK-801 (no suppression of epileptic events).

DETAILED DESCRIPTION OF THE INVENTION

Figure 1A:
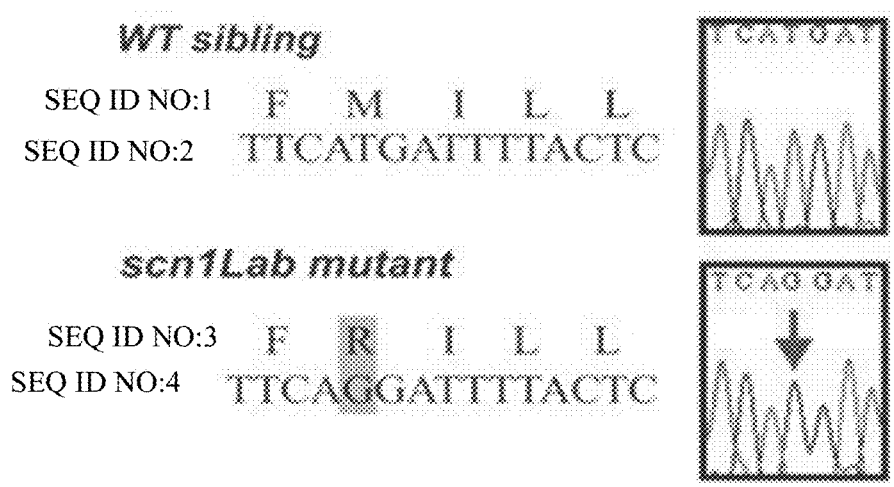
FIGS. 1A-1E. Molecular characterization of scn1Lab zebrafish mutants.

By "5HT Receptor" or "5-Hydroxytryptamine Receptor" is meant a group of G protein-coupled receptors (GPCRs) and ligand-gated ion channels (LGICs) that are found in the central (CNS) and peripheral nervous systems (PNS) and belong generally to the group of serotonin receptors. 5HT receptors may be divided into seven receptor families, including: $5HT_1$ (e.g., $G_i/G_0$-protein coupled receptors), $5HT_2$ (e.g., $G_q/G_{11}$-protein coupled receptors), $5HT_3$ (e.g., ligand-gated $Na^+$ and $K^+$ cation channel), $5HT_4$ (e.g., $G_s$-protein coupled receptors), $5HT_5$ (e.g., $G_i/G_0$-protein coupled receptors), $5HT_6$ (e.g., $G_s$-protein coupled receptors), and $5HT_7$ (e.g., $G_s$-protein coupled receptors). Additionally, the seven families of 5HT receptors may be further subdivided into a number of sub-families. For example, the $5HT_1$ family also includes the following sub-families: $5HT_{1A}$ (e.g., which are known to function in blood vessels and the CNS and may be involved in addiction, aggression, anxiety, appetite, autoreceptor, blood pressure, cardiovascular function, emesis, heart rate, impulsivity, memory, mood, nausea, nociception, penile erection, pupil dilation, respiration, sexual behavior, sleep, sociability, thermoregulation, and vasoconstriction), $5HT_{1B}$ (e.g., which are known to function in blood vessels and the CNS and may be involved in addiction, aggression, anxiety, auto receptor, learning, locomotion, memory, mood, penile erection, sexual behavior, and vasoconstriction), $5HT_{1D}$ (e.g., which are known to function in blood vessels and the CNS and may be involved in anxiety, autoreceptor, locomotion, and vasoconstriction), $5HT_{1E}$ (e.g., which are known to function in the CNS and may be involved in migraines). As another example, the $5HT_2$ family may be divided into the following sub-families: $5HT_{2A}$ (e.g., which are known to function in blood vessels, CNS, gastrointestinal tract, platelets, PNS, and smooth muscle, and may be involved in addiction, anxiety, appetite, cognition, imagination, learning, memory, mood, perception, sexual behavior, sleep, thermoregulation, and vasoconstriction), $5HT_{2B}$ (e.g., which are known to function in blood vessels, CNS, gastrointestinal tract, platelets, PNS, and smooth muscle, and may be involved in anxiety, appetite, cardiovascular function, gastrointestinal motility, sleep, and vasoconstriction), and $5HT_{2C}$ (e.g., which are known to function in blood vessels, CNS, gastrointestinal tract, platelets, PNS, and smooth muscle, and may be involved in addiction, anxiety, appetite, gastrointestinal motility, locomotion, mood, penile erection, sexual behavior, sleep, thermoregulation, and vasoconstriction). Additionally, the $5HT_5$ family may be further divided into the following sub-families: $5HT_{5A}$ (e.g., which may function in the CNS, and play a role in locomotion and sleep, as well as function as an autoreceptor) and 5HT$_{5B}$ (e.g., which may function in rodents and appears to be a pseudogene in humans).

By "5HT Receptor agonist" is meant any agent that activates a 5HT receptor relative to the absence of the 5HT Receptor agonist or in a manner similar to serotonin. Exemplary 5HT receptor agonists include, but are not limited to, any one or more of the following: ACP-104, ACP-106, AR-116081, AR-116082, ATHX-105, belladonna in combination with ergotamine tartrate, BW 723C86, Cisapride, Ciza-MPS, Cizap, Cizap-Mps, CSC-500 Series, DOI or salt thereof, Ergotamine Tartrate and Caffeine, Esorid MPS, flibanserin, Ikaran L.P., Manotac Plus, Migril, Mirtazapina Rimafar, mirtazapine, Naratriptan, nelotanserin, norfenfluramine, Normagut Tab, nefazodone hydrochloride, OSU-6162, Pridofin, Sensiflu, PRX-00933, RP-5063, Small Molecule to Agonize 5-HT$_{2A}$ for Inflammatory Diseases, Small Molecules to Agonize 5-HT$_{2C}$ for Schizophrenia and Obesity, Small Molecules to Agonize 5-HT$_{2C}$ Receptor for Obesity, Small Molecules to Target 5-HT$_{2C}$ and 5-HT$_6$ Receptor for Schizophrenia, Small Molecules to Modulate 5HT$_2$ for CNS and Metabolic Disorders, TGBA-01AD, trazodone hydrochloride, temanogrel hydrochloride, vabicaserin hydrochloride, Virdex, VR-1065, ziprasidone hydrochloride, and Ziprasidon-Sigillata.

In embodiments, the 5HT receptor agonist is sumatriptan, naratriptap, rizatriptan, zolmitriptan, urapidil, BRL-54443 (3-(1-methylpiperidin-4-yl)-1H-indol-5-01), lorcaserin, buspirone, ziprasidone, TCB-2 ((4-Bromo-3,6-dimethoxybenzocyclobuten-1-yl)methylamine hydrobromide), BRL-15572 (3-(4-(4-chlorophenyl)piperazin-1-yl)-1,1-diphenyl-2-propanol), trazodone, BMY 7378 (8-(2-[4-(2-methoxyphenyl)-1-piperazinyl]ethyl)-8-azaspiro[4.5]decane-7,9-dione), atomoxetine, or venlafaxine.

In embodiments, the 5HT receptor agonist is trazodone.

It is further contemplated within the scope of the disclosure that in some embodiments, a 5HT Receptor agonist does not include one or more or all of the following: acetazolamide, benzodiazepine (diazepam; clobazam), cannabadiol, carbamazepine, clemizole, ethosuximide, felbamate, fenfluramine, fluoxetine, gabapentin, ganaxolone, lacosamide, lamotrigine, levetiracetam, nitrazepam, oxcarbazepine, perampenel, phenytoin, phenobarbital, piracetam, potassium bromide, pregabalin, primidone, retigabine, rufinamide, stiripentol, tiagabine, topiramate, valproic acid, verapamil, vigabatrin, and zonisamide.

By "agent" is meant any small molecule chemical compound, antibody, nucleic acid molecule, or polypeptide, or fragments thereof.

By "cardiac condition" is meant related diseases, including, but not limited to: coronary heart disease (CHD), cardiomyopathy, cardiovascular disease (CVD), ischemic heart disease, heart failure, hypertensive heart disease, inflammatory heart disease, valvular heart disease, atherosclerosis, and cardiac hypertrophy. A cardiac condition may be a systemic disease that can affect the heart, brain, most major organs, and the extremities. By "coronary heart disease (CHD)" is meant a disease that causes the failure of coronary circulation to supply adequate circulation to the cardiac muscles and surrounding tissues. By "cardiovascular disease (CVD)" is meant any of a number of specific diseases that affect the heart itself or the blood vessel system, especially the myocardial tissue, as well as veins and arteries leading to and from the heart. For example, CVD may include, but is not limited to, acute coronary syndromes, arrhythmia, atherosclerosis, heart failure, myocardial infarction, neointimal hyperplasia, pulmonary hypertension, stroke, valvular disease, or cardiac hypertrophy. Heart disease may be diagnosed by any of a variety of methods known in the art. For example, such methods may include assessing a subject for dyspnea, orthopnea, paroxysmal nocturnal dyspnea, claudication, angina, chest pain, which may present as any of a number of symptoms known in the art, such as exercise intolerance, edema, palpitations, faintness, loss of consciousness, or cough; heart disease may be diagnosed by blood chemistry analysis. As described above and as used herein, "heart disease" relates to a disorder affecting the heart itself or the circulatory system.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

"Clemizole" refers to a compound having formula:

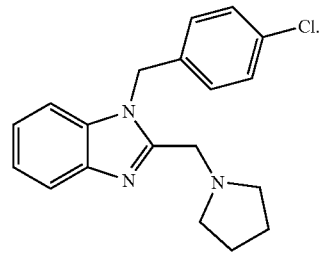 [SMILES: Clc1ccc(Cn2c(CN3CCCC3)nc3ccccc32)cc1]

Clemizole includes pharmaceutically acceptable salts and formulations of clemizole as described herein (e.g. a "clemizole salt"). Exemplary, clemizole salts include but are not limited to clemizole-HC1, clemizolpenicillin, clemizole-sulfate, or clemizole-undecylate.

A "clemizole analog" as set forth herein refers to compounds of similar structure. Such compounds include, for example, those compounds set forth in PCT/US2008/076804, and U.S. Pat. No. 4,011,322, which are herein incorporated by reference in their entirety. Further exemplary clemizole analogs are set forth, for example in: US 2012/0232062; PCT Pub. Nos. 2009/038248; US 2010/107739; US 2010/107742, WO 2002/089731. WO 2005/032329, WO 2009/039248, WO 2010/039195, WO 2010/107739, and WO 2010/107742, each of which is incorporated herein by reference in their entirety. Clemizole analogs described herein (including the compounds described in the references above) may be substituted (i.e. modified) at the 1 or 2 position as set forth below in formula (I) (boxes Y and Z). Clemizole analogs may be substituted (i.e. modified) at 4, 5, 6, or 7 positions as indicated by box X in formula (I).

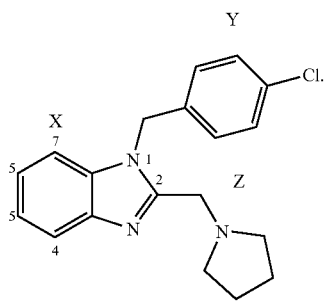

(I)

"Flibanserin" refers to a compound having the following formula (II):

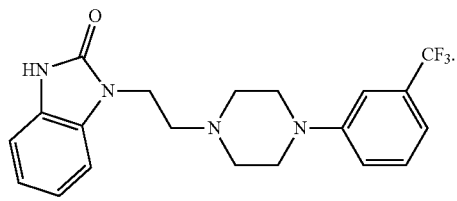

(II)

Flibanserin includes pharmaceutically acceptable salts and formulations of flibanserin (e.g. a "flibanserin salt").

"Norfenfluramine" refers to a compound having the following formula (III):

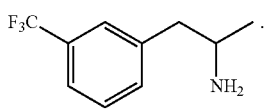

(III)

Norfenfluramine includes pharmaceutically acceptable salts and formulations of norfenfluramine (e.g. a "norfenfluramine salt").

"DOI" refers to 2,5-dimethoxy-4-Iodoamphetamine. DOI includes pharmaceutically acceptable salts and formulations of DOI. Exemplary, DOI salts include but are not limited to 2,5-dimethoxy-4-Iodoamphetamine monohydrochloride (DOI HCl) having the following formula (IV):

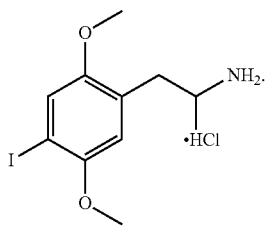

(IV)

"BW 723C86" refers to a tryptamine derivative drug that acts as a $5HT_{2B}$ receptor agonist and has the following formula (V):

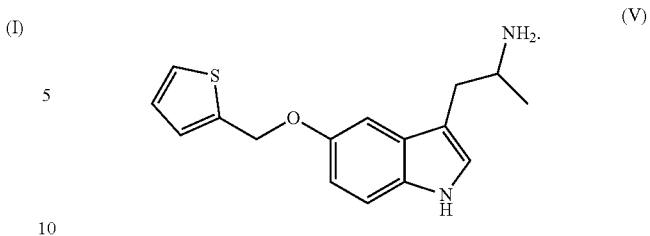

(V)

BW 723C86 includes pharmaceutically acceptable salts and formulations of BW 723C86 (e.g. a "BW 723C86 salt").

The term "pharmaceutically acceptable salts" is meant to include salts of the active compounds that are prepared with relatively nontoxic acids or bases, depending on the particular substituents found on the compounds described herein. When the 5-HT agonist contains relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When the 5-HT agonist contains relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). The 5-HT agonist may contain both basic and acidic functionalities that allow conversion into either base or acid addition salts.

Thus, the 5-HT agonist may exist as a salt, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the 5-HT agonist are preferably regenerated by contacting the salt with a base or acid and isolating the parent compound in the conventional manner. The parent form of the compound may differ from the various salt forms in certain physical properties, such as solubility in polar solvents.

In addition to salt forms, the 5-HT agonist may be provided in a prodrug form. Prodrugs are those compounds that readily undergo chemical changes under physiological conditions to provide the compounds of the present invention. Prodrugs of the 5-HT agonist may be converted in vivo after administration. Additionally, prodrugs of the 5-HT agonist can be converted to active compounds by chemical or biochemical methods in an ex vivo environment, such as, for example, when contacted with a suitable enzyme or chemical reagent.

The 5-HT agonist can exist in unsolvated forms as well as solvated forms, including hydrated forms. In general, the solvated forms are equivalent to unsolvated forms and are encompassed within the scope of the present invention. The 5-HT agonist may exist in multiple crystalline or amorphous forms. In general, all physical forms are equivalent for the uses contemplated by the present invention and are intended to be within the scope of the present invention.

An "effective amount" is an amount sufficient for the 5-HT agonist (including pharmaceutically acceptable salts thereof) to accomplish a stated purpose relative to the absence of a 5-HT agonist (including pharmaceutically acceptable salts thereof) (e.g. achieve the effect for which it is administered, treat a disease, reduce protein/enzyme activity, increase protein/enzyme activity, reduce a signaling pathway, or reduce one or more symptoms of a disease or condition). An example of an "effective amount" is an amount of the 5-HT agonist (including pharmaceutically acceptable salts thereof) which is sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s) (e.g. seizures). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms (e.g. seizures). The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The therapeutically effective amount of the 5-HT agonist (including pharmaceutically acceptable salts thereof) can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a 5-HT agonist in the absence of a 5-HT agonist (including pharmaceutically acceptable salts thereof).

A "test compound" as used herein refers to an experimental compound used in a screening process to identify activity, non-activity, or other modulation of a particularized biological target or pathway, for example a 5-HT receptor. A test compound may be a 5-HT agonist described herein, including pharmaceutically acceptable salts thereof.

The term "modulation", "modulate", or "modulator" are used in accordance with their plain ordinary meaning and refer to the act of changing or varying one or more properties. "Modulator" refers to a composition or compound that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target (e.g. a 5-HT receptor).

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or protein/enzymatic activity or the amount of a protein.

The term "activation" or "activating" and the like in reference to protein-compound interactions that positively affect (e.g. increase) the activity or function of the protein relative to the activity or function of the protein in absence of the activator compound. Activation may refer to enhanced activity of a particular protein target. Activation may refer to restoration of loss-of-function of a mutated protein target. Activation as used herein may refer to activation of one or more 5-HT receptors.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a receptor, e.g. a 5-HT receptor.

The term "associated" or "associated with" in the context of a substance or substance activity or function associated with a disease means that the disease is caused by (in whole or in part), or a symptom of the disease is caused by (in whole or in part) the substance or substance activity or function.

The term "patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals such as zebrafish. A patient may be human.

The term "disease" or "condition" refer to a state of being or health status of a patient or subject capable of being treated with the compounds or methods provided herein.

The terms "epileptic disorder," "epilepsy disorder," "seizure disorder," or "epilepsy" herein refer to a spectrum of chronic neurological disorders most often characterized by the presence of unprovoked seizures. See e.g. Noebels et. al., Jasper's Basic Mechanisms of the Epilepsies, 4th edition, Bethesda (MD): National Center for Biotechnology Information (US); 2012. Epilepsy as used herein, may refer to injury to the brain (e.g. from trauma, stroke, or cancer) or genetic mutation. The symptoms of epilepsy disorders may result from abnormal electrochemical signaling between neurons in the brain. Patients experiencing two or more unprovoked seizures may be considered to have epilepsy.

Types of epilepsy disorders include, for example, benign Rolandic epilepsy, frontal lobe epilepsy, infantile spasms, juvenile myoclonic epilepsy (JME), juvenile absence epilepsy, childhood absence epilepsy (e.g. pyknolepsy), febrile seizures, progressive myoclonus epilepsy of Lafora, Lennox-Gastaut syndrome, Landau-Kleffner syndrome, Dravet syndrome (DS), Generalized Epilepsy with Febrile Seizures (GEFS+), Severe Myoclonic Epilepsy of Infancy (SMEI), Benign Neonatal Familial Convulsions (BFNC), West Syndrome, Ohtahara Syndrome, early myoclonic encephalopathies, migrating partial epilepsy, infantile epileptic encephalopathies, Tuberous Sclerosis Complex (TSC), focal cortical dysplasia, Type I Lissencephaly, Miller-Dieker Syndrome, Angelman's syndrome, Fragile X syndrome, epilepsy in autism spectrum disorders, subcortical band heterotopia, Walker-Warburg syndrome, Alzheimer's disease, posttraumatic epilepsy, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Unverricht-Lundborg disease, or photosensitive epilepsy.

"Pharmaceutically acceptable excipient" and "pharmaceutically acceptable carrier" or "carrier moiety" refer to a substance that aids the administration of the 5-HT agonist (including pharmaceutically acceptable salts thereof) to and absorption by a subject and can be included in the compositions without causing a significant adverse toxicological effect on the patient.

Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutically acceptable excipients are useful in the present invention.

The term "preparation" is intended to include the formulation of the 5-HT agonist (including pharmaceutically acceptable salts thereof) with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal).

Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The 5-HT agonist (including pharmaceutically acceptable salts thereof) and pharmaceutical compositions thereof can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient.

Solid form preparations include powders, tablets, pills, capsules, cachets, suppositories, and dispersible granules. Liquid form preparations include solutions, suspensions, and emulsions, for example, water or water/propylene glycol solutions. The 5-HT agonists (including pharmaceutically acceptable salts thereof) may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The 5-HT agonist (including pharmaceutically acceptable salts thereof) can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). The formulations of the compositions of the 5-HT agonist (including pharmaceutically acceptable salts thereof) can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the 5-HT agonist (including pharmaceutically acceptable salts thereof) into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

By "co-administer" it is meant that a composition described herein is administered at the same time, just prior to, or just after the administration of one or more additional therapies. The 5-HT agonist (including pharmaceutically acceptable salts thereof) can be administered alone or can be co-administered to the patient. Co-administration is meant to include simultaneous or sequential administration of the compounds individually or in combination (more than one compound). Thus, the preparations can also be combined, when desired, with other active substances (e.g. to reduce metabolic degradation). The 5-HT agonist (including pharmaceutically acceptable salts thereof) can be delivered transdermally, by a topical route, or formulated as applicator sticks, solutions, suspensions, emulsions, gels, creams, ointments, pastes, jellies, paints, powders, and aerosols.

The terms "add on therapy," "add-on therapy," "adjunct therapy," and "adjunctive therapy" are used interchangeably herein and refer to combining of the 5-HT agonist or a pharmaceutically acceptable salt thereof with another anticonvulsant to treat epilepsy.

An "anti-seizure drug", "anti-epilepsy drug", "AED" or "anticonvulsant" are used interchangeably herein and according to their common and ordinary meaning and include compositions for reducing or eliminating seizures. Anticonvulsants include, but are not limited to acetazolamide, benzodiazepine, cannabadiols, carbamazepine, clobazam, clonazepam, eslicarbazepine acetate, ethosuximide, ethotoin, felbamate, fenfluramine, fosphenytoin, gabapentin, ganaxolone, huperzine A, lacosamide, lamotrigine, levetiracetam, nitrazepam, oxcarbazepine, perampanel, piracetam, phenobarbital, phenytoin, potassium bromide, pregabalin, primidone, retigabine, rufinamide, valproic acid, sodium valproate, stiripentol, tiagabine, topiramate, vigabatrin, or zonisamide.

As used herein, the term "resistant" refers to a reduction in the effectiveness of an agent or drug. For example, a subject that is "resistant" to treatment with a serotonin reuptake inhibitor (such as, e.g. fenfluramine) displays a reduced response relative to the response observed when the subject was first treated with the serotonin reuptake inhibitor.

As used herein, the term "does not significantly bind" shall be taken to mean that a 5HT Receptor agonist of the disclosure displays 10 fold, or 20 fold or 50 fold or 60 fold or 70 fold or 80 fold or 90 fold or 100 fold, less binding to another transmembrane protein, such as, for example, a 5HT receptor, a NPY YP receptor, a $Ca^+$ channel, a Cl channel, a GABA transporter or GABA-A1 receptor, a Na channel, a 5HT transporter, and/or a CB1 or CB2 receptor. This decreased level of binding may be measured by ELISA or biosensor analysis (e.g., Biacore). In one example, a 5HT Receptor agonist of the disclosure does not detectably bind to $5HT_{1A}$, $5HT_{1B}$, $5HT_{1D}$, $5HT_{2C}$, $5HT_3$, $5HT_4$, $5HT_6$, $5HT_7$, NPY Y1 receptor, L-type Ca channel, Ca channel (N-type), SK-Ca channel, GABA-gated Cl channel, GABA transporter, GABA-A1 receptor, GABA-B1b receptor, Na channel, 5HT transporter, CB1 receptor, CB2 receptor, BZD or Estrogen ER alpha, as measured by ELISA or Biacore or Western Blot or FACS. In this regard, "does not detectably bind" shall be understood to mean that the level of binding is not significantly greater than background. In exemplary embodiments, the 5-HT agonist does not significantly modulate the activity of at least one of $5HT_{1A}$, $5HT_{1B}$, $5HT_{1D}$, $5HT_{2C}$, $5HT_3$, $5HT_4$, $5HT_6$, $5HT_7$, NPY Y1 receptor, L-type Ca channel, N-type Ca channel, SK-Ca channel, GABA-gated Cl channel, GABA transporter, GABA-A1 receptor, GABA-B1b receptor, Na channel, 5HT transporter, CB1 receptor, CB2 receptor, BZD or Estrogen ER alpha. As used herein, the term "does not significantly modulate the activity" shall be taken to mean that a 5HT Receptor agonist of the disclosure elicits a receptor mediated biological response which is substantially similar to its activity absent activating or inhibiting ligand.

Methods of Treatment

Provided herein are methods of treating an epilepsy disorder. In one aspect, the method is a method of treating an epilepsy disorder by administering to a subject in need thereof, a therapeutically effective amount of a 5-HT receptor agonist or a pharmaceutically acceptable salt thereof. In another aspect, the method is a method of treating an epilepsy disorder by administering to a subject in need thereof, a pharmaceutical composition as described herein, where the pharmaceutical composition includes a 5-HT receptor agonist or a pharmaceutically acceptable salt thereof. The subject may have (e.g. may eat food in accordance with) a ketogenic diet. The subject may have a cardiovascular disease. The subject may be resistant to treatment with a serotonin reuptake inhibitor. The subject may be susceptible to side effects when administered a serotonin reuptake inhibitor. The subject may be a child (e.g. a subject having a pediatric epilepsy condition).

The epilepsy disorder may be benign Rolandic epilepsy, frontal lobe epilepsy, infantile spasms, juvenile myoclonic epilepsy (JME), juvenile absence epilepsy, childhood absence epilepsy (e.g. pyknolepsy), febrile seizures, progressive myoclonus epilepsy of Lafora, Lennox-Gastaut syndrome, Landau-Kleffner syndrome, Dravet syndrome, Generalized Epilepsy with Febrile Seizures (GEFS+), Severe Myoclonic Epilepsy of Infancy (SMEI), Benign Neonatal Familial Convulsions (BFNC), West Syndrome, Ohtahara Syndrome, early myoclonic encephalopathies, migrating partial epilepsy, infantile epileptic encephalopathies, Tuberous Sclerosis Complex (TSC), focal cortical dysplasia, Type I Lissencephaly, Miller-Dieker Syndrome, Angelman's syndrome, Fragile X syndrome, epilepsy in autism spectrum disorders, subcortical band heterotopia, Walker-Warburg syndrome, Alzheimer's disease, posttraumatic epilepsy, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Unverricht-Lundborg disease, or photosensitive epilepsy. The epilepsy may include generalized seizures or partial (i.e. focal) seizures.

The epilepsy disorder may be Dravet Syndrome, Lennox-Gastaut Syndrome, infantile spasm, or Ohtahara Syndrome. The epilepsy disorder may be Dravet Syndrome, Lennox-Gastaut Syndrome, infantile spasm, or Ohtahara Syndrome, or a pediatric epilepsy disorder. The pediatric epilepsy disorder may be benign childhood epilepsy, Benign Neonatal Familial Convulsions (BFNC), febrile seizures, Dravet Syndrome, Lennox-Gastaut Syndrome, infantile spasm, Ohtahara Syndrome, juvenile myoclonic epilepsy, juvenile absence epilepsy, childhood absence epilepsy (e.g. pyknolepsy), infantile spasms. The epilepsy disorder may be Dravet Syndrome.

The pediatric epilepsy disorder may be benign childhood epilepsy. The pediatric epilepsy disorder may be Benign Neonatal Familial Convulsions (BFNC). The pediatric epilepsy disorder may be febrile seizures. The pediatric epilepsy disorder may be Dravet Syndrome. The pediatric epilepsy disorder may be Lennox-Gastaut Syndrome. The pediatric epilepsy disorder may be infantile spasm. The pediatric epilepsy disorder may be Ohtahara Syndrome. The pediatric epilepsy disorder may be juvenile myoclonic epilepsy. The pediatric epilepsy disorder may be juvenile absence epilepsy. The pediatric epilepsy disorder may be childhood absence epilepsy (e.g. pyknolepsy). The pediatric epilepsy disorder may be infantile spasms.

The epilepsy disorder may be a result of a neurological disease or injury such as, for example, encephalitis, cerebritis, abscess, stroke, tumor, trauma, genetic, tuberous sclerosis, cerebral dysgenesis, or hypoxic-ischemic encephalopathy. The epilepsy disorder may be associated with a neurodegenerative disease such as, for example, Alzheimer's disease or Parkinson's Disease. The epilepsy disorder may be associated with autism. The epilepsy disorder may be associated with a single gene mutation. The epilepsy disease may be associated with compulsive behaviors or electrographic seizures. The administration of the 5-HT receptor agonist or a pharmaceutical acceptable salt thereof may inhibit compulsive behaviors or electrographic seizures in a epilepsy disorder, in an Alzheimer's disease subject (e.g. a subject suffering from Alzheimer's disease), in an autism subject (e.g. a subject having autism), or in a Parkinson's disease subject (e.g. a subject suffering from Parkinson's disease). Thus, the 5-HT receptor agonist or a pharmaceutical acceptable salt thereof may inhibit compulsive behaviors or electrographic seizures in a epilepsy disorder. The 5-HT agonist or a pharmaceutical acceptable salt thereof may inhibit compulsive behaviors or electrographic seizures in an Alzheimer's disease subject. The 5-HT receptor agonist or a pharmaceutical acceptable salt thereof may inhibit compulsive behaviors or electrographic seizures in an autism subject. The 5-HT receptor agonist or a pharmaceutical acceptable salt thereof may inhibit compulsive behaviors or electrographic seizures in a Parkinson's disease subject.

The administration of the 5-HT receptor agonist or a pharmaceutical acceptable salt thereof may reduce the incidence (e.g. number of occurrences) of unprovoked seizures in the subject compared to the absence of a 5-HT receptor agonist or the pharmaceutically acceptable salt thereof. Thus, a patient's response to the administration of the 5-HT receptor agonist or a pharmaceutical acceptable salt thereof, may be monitored progressively compared to a time before the administration of compounds described herein (e.g. a control or control time).

The administration of the 5-HT receptor agonist or a pharmaceutical acceptable salt thereof may reduce or prevent myoclonus seizures or status epilepticus in the subject compared to the absence of a 5-HT receptor agonist or the pharmaceutically acceptable salt thereof. The administration of the 5-HT receptor agonist or a pharmaceutical acceptable salt thereof may reduce or prevent myoclonus seizures in the subject compared to the absence of a 5-HT receptor agonist or the pharmaceutically acceptable salt thereof. The administration of the 5-HT receptor agonist or a pharmaceutical acceptable salt thereof may reduce or prevent status epilepticus in the subject compared to the absence of a 5-HT receptor agonist or the pharmaceutically acceptable salt thereof. Thus, a patient's response to the administration of the 5-HT receptor agonist or a pharmaceutical acceptable salt thereof, may be monitored progressively compared to a time before the administration of compounds described herein (e.g. a control or control time).

The epilepsy disorder may be an epilepsy disorder which is non-responsive to treatment with an antiepileptic drug (AED) The subject may eat a ketogenic diet. The epilepsy disorder may be an epilepsy disorder in an adult (e.g. more than about 16 years old).

The epilepsy disorder may be an epilepsy disorder in children. Thus, the epilepsy disorder may be a pediatric epilepsy disorder. The child may be less than about 1 week old. The child may be less than about 1 month old. The child may be less than about 6 months old. The child may be less than about 12 months old. The child may be less than about 2 years old. The child may be less than about 3 years old. The child may be less than about 4 years old. The child may be less than about 5 years old. The child may be less than about 6 years old. The child may be less than about 7 years old. The child may be less than about 8 years old. The child may be less than about 9 years old. The child may be less than about 10 years old. The child may be less than about 12 years old.

The child may be more than about 1 week old. The child may be more than about 1 month old. The child may be more than about 6 months old. The child may be more than about 12 months old. The child may be more than about 2 years old. The child may be more than about 3 years old. The child may be more than about 4 years old. The child may be more than about 5 years old. The child may be more than about 5 years old. The child may be more than about 6 years old. The child may be more than about 7 years old. The child may be more than about 8 years old. The child may be more than about 9 years old. The child may be more than about 10 years old. The child may be more than about 11 years old. The child may be more than about 12 years old.

The child may have an epilepsy disorder treated by administering an AED as described herein. Thus, the 5-HT receptor agonist or a pharmaceutically acceptable salt thereof may be administered to such a child (e.g. as an add-on therapy).

In another aspect, is a method of treating Dravet Syndrome. The method of treating Dravet Syndrome includes administering to a subject in need thereof, a therapeutically effective amount of the 5-HT receptor agonist or a pharmaceutically acceptable salt thereof. The method of treating Dravet Syndrome may include administering to a subject in need thereof, a pharmaceutical composition of the 5-HT receptor agonist or a pharmaceutically acceptable salt thereof as described herein. The 5-HT receptor agonist (including pharmaceutically acceptable salts thereof) may be co-administered to a subject in need thereof with an AED as described herein.

In the methods described herein, the 5-HT receptor agonist (including pharmaceutically acceptable salts thereof) may be co-administered with an anti-epileptic drug (AED) The AED may be acetazolamide, benzodiazepine, cannabadiols, carbamazepine, clobazam, clonazepam, eslicarbazepine acetate, ethosuximide, ethotoin, felbamate, fenfluramine, fosphenytoin, gabapentin, ganaxolone, huperzine A, lacosamide, lamotrigine, levetiracetam, nitrazepam, oxcarbazepine, perampanel, piracetam, phenobarbital, phenytoin, potassium bromide, pregabalin, primidone, retigabine, rufinamide, valproic acid, sodium valproate, stiripentol, tiagabine, topiramate, vigabatrin, or zonisamide. The AED may be valproic acid, sodium valproate, clonazepam, ethosuximide, felbamate, gabapentin, carbamazepine, oxcarbazepine, lamotrigine, levetiracetam, benzodiazepine, phenobarbital, pregabalin, primidone, tiagabine, topiramate, potassium bromide, phenytoin, stiripentol, vigabatrin, or zonisamide. The AED may be valproic acid, sodium valproate, gabapentin, topiramate, carbamazepine, oxcarbazepine, or vigabatrin.

The AED may be acetazolamide. The AED may be benzodiazepine. The AED may be cannabadiols. The AED may be carbamazepine. The AED may be clobazam. The AED may be clonazepam. The AED may be eslicarbazepine acetate. The AED may be ethosuximide. The AED may be ethotoin. The AED may be felbamate. The AED may be fenfluramine. The AED may be fosphenytoin. The AED may be gabapentin. The AED may be ganaxolone. The AED may be huperzine A. The AED may be lacosamide. The AED may be lamotrigine. The AED may be levetiracetam. The AED may be nitrazepam. The AED may be oxcarbazepine. The AED may be perampanel. The AED may be piracetam. The AED may be phenobarbital. The AED may be phenytoin. The AED may be potassium bromide. The AED may be pregabalin. The AED may be primidone. The AED may be retigabine. The AED may be rufinamide. The AED may be valproic acid. The AED may be sodium valproate. The AED may be stiripentol. The AED may be tiagabine. The AED may be topiramate. The AED may be vigabatrin. The AED may be zonisamide. Clemizole or a clemizole analog (including pharmaceutically acceptable salts thereo) or a pharmaceutical composition of clemizole or a clemizole analog may be administered as an adjunctive therapy to one or more of the AEDs described herein.

The 5-HT receptor agonist or a pharmaceutically acceptable salt thereof may be administered as an add-on (e.g. in combination with) AED medications for treating seizures, including seizures associated with the epilepsy disorders described herein. The 5-HT receptor agonist or a pharmaceutically acceptable salt thereof may be administered as an adjunctive therapy (e.g. in combination with) AED medications for treating seizures, including seizures associated with the epilepsy disorders described herein.

The epilepsy disorder may be characterized by partial seizures or generalized seizures. The epilepsy disorder may be characterized by partial seizures. The epilepsy disorder may be characterized by generalized seizures. The partial seizure may be a simple focal seizure, a complex focal seizure, or a partial focal seizure with secondary generalization. The generalized seizure may be a generalized tonic-clonic seizure, an absence seizure (i.e. petit mal), a myoclonic seizure, a clonic seizure, a tonic seizure, or a atonic seizure.

When co-administered with the AEDs described herein, the 5-HT receptor agonist (including pharmaceutically acceptable salts thereof) and the AED may be administered simultaneously. When administered simultaneously, the 5-HT receptor agonist (including pharmaceutically acceptable salts thereof) may be formulated together with the AED (i.e. in a single dosage unit). The 5-HT receptor agonist (including pharmaceutically acceptable salts thereof) may be formulated for separate administration from the AED but administered at the same time. When co-administered with AEDs described herein, the 5-HT receptor agonist (including pharmaceutically acceptable salts thereof) may be administered sequentially (e.g. before or after) the administration of the AED. As set forth herein, one skilled in the art could readily determine the sequential order of administration.

The 5-HT receptor agonist (including pharmaceutically acceptable salts thereof) may be administered at a dose of about 1 mg/kg to about 1000 mg/kg. The 5-HT receptor agonist (including pharmaceutically acceptable salts thereof) may be administered at a dose of about 10 mg/kg to about 1000 mg/kg. The 5-HT receptor agonist (including pharmaceutically acceptable salts thereof) may be administered at a dose of about 10 mg/kg to about 600 mg/kg. The 5-HT receptor agonist (including pharmaceutically acceptable salts thereof) may be administered at a dose of about 25 mg/kg to about 500 mg/kg. The 5-HT receptor agonist (including pharmaceutically acceptable salts thereof) may be administered at a dose of about 25 mg/kg to about 400 mg/kg. The 5-HT receptor agonist (including pharmaceutically acceptable salts thereof) may be administered at a dose of about 25 mg/kg to about 350 mg/kg. The 5-HT receptor agonist (including pharmaceutically acceptable salts thereof) may be administered at a dose of about 25 mg/kg to about 300 mg/kg. The 5-HT receptor agonist (including pharmaceutically acceptable salts thereof) may be administered at a dose of about 25 mg/kg to about 250 mg/kg. The 5-HT receptor agonist (including pharmaceutically acceptable salts thereof) may be administered at a dose of about 25 mg/kg to about 200 mg/kg. The 5-HT receptor agonist (including pharmaceutically acceptable salts thereof) may be administered at a dose of about 25 mg/kg to about 150 mg/kg. The 5-HT receptor agonist (including pharmaceutically acceptable salts thereof) may be administered at a dose of about 25 mg/kg to about 100 mg/kg. The 5-HT receptor agonist (including pharmaceutically acceptable salts thereof) may be administered at a dose of about 25 mg/kg to about 75 mg/kg. The 5-HT receptor agonist (including pharmaceutically acceptable salts thereof) may be administered at a dose of about 25 mg/kg to about 50 mg/kg. As used herein "mg/kg" refers to mg per kg body weight of the subject. Dosages described herein include administration of the 5-HT receptor agonist (including pharmaceutically acceptable salts thereof) as a single therapeutic active agent or administration of the 5-HT receptor agonist (including pharmaceutically acceptable salts thereof) as a therapeutic active agent in combination (as described herein) with an AED described herein.

The 5-HT receptor agonist (including pharmaceutically acceptable salts thereof) may be administered at a dose of about 1 mg/kg. The 5-HT receptor agonist (including pharmaceutically acceptable salts thereof) may be administered at a dose of about 5 mg/kg. The 5-HT receptor agonist (including pharmaceutically acceptable salts thereof) may be administered at a dose of about 10 mg/kg. The 5-HT receptor agonist (including pharmaceutically acceptable salts thereof) may be administered at a dose of about 20 mg/kg. The 5-HT receptor agonist (including pharmaceutically acceptable salts thereof) may be administered at a dose of about 25 mg/kg. The 5-HT receptor agonist (including pharmaceutically acceptable salts thereof) may be administered at a dose of about 30 mg/kg. The 5-HT receptor agonist (including pharmaceutically acceptable salts thereof) may be administered at a dose of about 40 mg/kg. The 5-HT receptor agonist (including pharmaceutically acceptable salts thereof) may be administered at a dose of about 50 mg/kg. The 5-HT receptor agonist (including pharmaceutically acceptable salts thereof) may be administered at a dose of about 75 mg/kg. The 5-HT receptor agonist (including pharmaceutically acceptable salts thereof) may be administered at a dose of about 100 mg/kg.

The 5-HT receptor agonist (including pharmaceutically acceptable salts thereof) may be administered at a dose of about 125 mg/kg. The 5-HT receptor agonist (including pharmaceutically acceptable salts thereof) may be administered at a dose of about 150 mg/kg. The 5-HT receptor agonist (including pharmaceutically acceptable salts thereof) may be administered at a dose of about 175 mg/kg. The 5-HT receptor agonist (including pharmaceutically acceptable salts thereof) may be administered at a dose of about 200 mg/kg. The 5-HT receptor agonist (including pharmaceutically acceptable salts thereof) may be administered at a dose of about 225 mg/kg. The 5-HT receptor agonist (including pharmaceutically acceptable salts thereof) may be administered at a dose of about 250 mg/kg. The 5-HT receptor agonist (including pharmaceutically acceptable salts thereof) may be administered at a dose of about 275 mg/kg.

The 5-HT receptor agonist (including pharmaceutically acceptable salts thereof) may be administered at a dose of about 300 mg/kg. The 5-HT receptor agonist (including pharmaceutically acceptable salts thereof) may be administered at a dose of about 325 mg/kg. The 5-HT receptor agonist (including pharmaceutically acceptable salts thereof) may be administered at a dose of about 350 mg/kg. The 5-HT receptor agonist (including pharmaceutically acceptable salts thereof) may be administered at a dose of about 375 mg/kg. The 5-HT receptor agonist (including pharmaceutically acceptable salts thereof) may be administered at a dose of about 400 mg/kg. The 5-HT receptor agonist (including pharmaceutically acceptable salts thereof) may be administered at a dose of about 425 mg/kg. The 5-HT receptor agonist (including pharmaceutically acceptable salts thereof) may be administered at a dose of about 450 mg/kg. The 5-HT receptor agonist (including pharmaceutically acceptable salts thereof) may be administered at a dose of about 475 mg/kg.

The 5-HT receptor agonist (including pharmaceutically acceptable salts thereof) may be administered at a dose of about 500 mg/kg. The 5-HT receptor agonist analog (including pharmaceutically acceptable salts thereof) may be administered at a dose of about 600 mg/kg. The 5-HT receptor agonist (including pharmaceutically acceptable salts thereof) may be administered at a dose of about 700 mg/kg. The 5-HT receptor agonist (including pharmaceutically acceptable salts thereof) may be administered at a dose of about 800 mg/kg. The 5-HT receptor agonist (including pharmaceutically acceptable salts thereof) may be administered at a dose of about 900 mg/kg. The 5-HT receptor agonist (including pharmaceutically acceptable salts thereof) may be administered at a dose of about 1000 mg/kg.

The 5-HT receptor agonist (including pharmaceutically acceptable salts thereof) may be administered in the dosages described herein at least once a day (e.g. once every 1, 2, 3, 4, 5, 6, 7, 8, 9, 10, 11, or 12 hours). The 5-HT receptor agonist (including pharmaceutically acceptable salts thereof) may be administered daily in the dosages described herein. The 5-HT receptor agonist (including pharmaceutically acceptable salts thereof) may be administered at least twice a week in the dosages described herein. The 5-HT receptor agonist (including pharmaceutically acceptable salts thereof) may be administered at least three times a week as described herein. The 5-HT receptor agonist (including pharmaceutically acceptable salts thereof) may be administered monthly as described herein.

Provided herein are methods of treating a disease or disorder caused by a deficiency of serotonin in the brain or under activity of one or more 5HT receptors by administering a therapeutically effective amount of clemizole, a clemizole analog, or a pharmaceutically acceptable salt thereof. The disease or disorder caused by a deficiency of serotonin in the brain or under activity of one or more 5HT receptors may be a migraine. The disease or disorder caused by a deficiency of serotonin in the brain or under activity of one or more 5HT receptors may be Fragile X syndrome. The disease or disorder caused by a deficiency of serotonin in the brain or under activity of one or more 5HT receptors may be Prader-Willi syndrome. The disease or disorder caused by a deficiency of serotonin in the brain or under activity of one or more 5HT receptors may be schizophrenia. The disease or disorder caused by a deficiency of serotonin in the brain or under activity of one or more 5HT receptors may be depression. The disease or disorder caused by a deficiency of serotonin in the brain or under activity of one or more 5HT receptors may be Alzheimer's disease. The disease or disorder caused by a deficiency of serotonin in the brain or under activity of one or more 5HT receptors may be autism. The disease or disorder caused by a deficiency of serotonin in the brain or under activity of one or more 5HT receptors may be neuropathic pain. The disease or disorder caused by a deficiency of serotonin in the brain or under activity of one or more 5HT receptors may be Parkinson's disease. The disease or disorder caused by a deficiency of serotonin in the brain or under activity of one or more 5HT receptors may be irritable bowel disorder. The disease or disorder caused by a deficiency of serotonin in the brain or under activity of one or more 5HT receptors may be dementia.

Further provided herein is a method of modulating activity of a 5HT receptor comprising contacting a 5HT receptor with clemizole, a clemizole analog, or a pharmaceutically acceptable salt thereof.

The analog of clemizole may include compounds of formula (I) described herein and may include compounds of similar structure as set forth, in for example, PCT/US2008/076804, WO10107739, WO2009039248, or U.S. Pat. No. 4,011,322, which are incorporated herein by reference.

In embodiments, the disclosure provides methods of treating epilepsy or Dravet syndrome by administering a therapeutically effective amount of trazadone or a pharmaceutically acceptable salt thereof. In embodiments, the therapeutically effective amount is from about 10 mg/day to about 600 mg/day. In embodiments, the methods are for treating epilepsy. In embodiments, the epilepsy is pediatric epilepsy. In embodiments, the methods are for treating Dravet syndrome.

Pharmaceutical Compositions

Provided herein are pharmaceutical compositions comprising a 5-HT receptor agonist or a pharmaceutically acceptable salt thereof useful for treating the aforementioned diseases and disorders. The pharmaceutical composition may be formulated as a tablet, a powder, a capsule, a pill, a cachet, or a lozenge as described herein. The pharmaceutical composition may be formulated as a tablet, capsule, pill, cachet, or lozenge for oral administration. The pharmaceutical composition may be formulated for dissolution into a solution for administration by such techniques as, for example, intravenous administration. The pharmaceutical composition may be formulated for oral administration, suppository administration, topical administration, intravenous administration, intraperitoneal administration, intramuscular administration, intralesional administration, intrathecal administration, intranasal administration, subcutaneous administration, implantation, transdermal administration, or transmucosal administration as described herein.

When administered as pharmaceutical composition, the pharmaceutical compositions may include optical isomers, diastereomers, enantiomers, isoforms, polymorphs, hydrates, solvates or products, or pharmaceutically acceptable salts of the 5-HT receptor agonist. The 5-HT receptor agonist (including pharmaceutically acceptable salts thereof) included in the pharmaceutical composition may be covalently attached to a carrier moiety, as described above. Alternatively, the 5-HT receptor agonist (including pharmaceutically acceptable salts thereof) included in the pharmaceutical composition is not covalently linked to a carrier moiety.

The 5-HT receptor agonist (including pharmaceutically acceptable salts thereof) may be administered alone or co-administered to a subject in need thereof with an AED as described herein. Co-administration is meant to include simultaneous or sequential administration as described herein of the 5-HT receptor agonist individually or in combination (e.g. more than one compound—e.g. an AED described herein). The preparations can also be combined, when desired, with other active substances (e.g. to prevent seizures).

Formulations

The 5-HT receptor agonist (including pharmaceutically acceptable salts thereof) or a pharmaceutical composition described herein can be prepared and administered in a wide variety of oral, parenteral, and topical dosage forms. Thus, the 5-HT receptor agonist (including pharmaceutically acceptable salts thereof) or a pharmaceutical composition described herein can be administered by injection (e.g. intravenously, intramuscularly, intracutaneously, subcutaneously, intraduodenally, or intraperitoneally). Also, the 5-HT receptor agonist (including pharmaceutically acceptable salts thereof) or a pharmaceutical composition described herein can be administered by inhalation, for example, intranasally. Additionally, the 5-HT receptor agonist (including pharmaceutically acceptable salts thereof) or a pharmaceutical composition can be administered transdermally. It is also envisioned that multiple routes of administration (e.g., intramuscular, oral, transdermal) can be used to administer the 5-HT receptor agonist (including pharmaceutically acceptable salts thereof) or a pharmaceutical composition comprising same. The pharmaceutical compositions described herein may include a pharmaceutically acceptable carrier or excipient and one or more of a 5-HT receptor agonist (including pharmaceutically acceptable salts thereof). The pharmaceutical compositions described herein may include a pharmaceutically acceptable carrier or excipient, one or more of a 5-HT receptor agonist (including pharmaceutically acceptable salts thereof) and an one or more AED as described herein.

Preparation may include pharmaceutically acceptable carriers. The pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of the 5-HT receptor agonist (including pharmaceutically acceptable salts thereof) or a pharmaceutical composition (i.e., dosage). Pharmaceutical preparations described herein can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the 5-HT receptor agonist (including pharmaceutically acceptable salts thereof) or a pharmaceutical composition comprising same are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The 5-HT receptor agonist (including pharmaceutically acceptable salts thereof) or a pharmaceutical composition comprising same can also be incorporated into liposomes or administered via transdermal pumps or patches. Pharmaceutical admixtures suitable for use herein include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included herein are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations described herein can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Formulations may include a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity-building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The pharmaceutical compositions may additionally include components to provide sustained release and/or comfort. Such components include high molecular weight, anionic mucomimetic polymers, gelling polysaccharides, and finely-divided drug carrier substrates.

These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

The 5-HT receptor agonist (including pharmaceutically acceptable salts thereof) or a pharmaceutical composition thereof can be delivered transdermally, for treating the epilepsy disorders described herein, by a topical route, formulated as applicator sticks, solutions, suspensions, emulsions, gels, creams, ointments, pastes, jellies, paints, powders, and aerosols.

The 5-HT receptor agonist (including pharmaceutically acceptable salts thereof) can be provided as a salt in the pharmaceutical compositions described herein and can be formed with many acids, including but not limited to hydrochloric, sulfuric, acetic, lactic, tartaric, malic, succinic, etc. Salts tend to be more soluble in aqueous or other protonic solvents that are the corresponding free base forms.

The 5-HT receptor agonist (including pharmaceutically acceptable salts thereof) or a pharmaceutical composition thereof administered for treating epilepsy disorders described herein may be administered via parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

The pharmaceutical formulations of the 5-HT receptor agonist (including pharmaceutically acceptable salts thereof) for treating an epilepsy disorder can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

Co-administration includes administering one active agent (e.g. clemizole or a clemizole analog (including pharmaceutically acceptable salts thereof)) within 0.5, 1, 2, 4, 6, 8, 10, 12, 16, 20, or 24 hours of a second active agent (e.g. an anticonvulsant). Co-administration may include administering one active agent within 0.5, 1, 2, 4, 6, 8, 10, 12, 16, 20, or 24 hours of a second active agent. Co-administration may include administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another.

Co-administration also includes combination with treatments for epilepsy disorders such as dietary requirements or dietary changes. Accordingly, the 5-HT receptor agonist (including pharmaceutically acceptable salts thereof) or a pharmaceutical composition thereof may be administered to subjects on specialized diets, including but not limited to, a ketogenic diet (e.g. a high-fat, adequate-protein, low-carbohydrate diet).

Effective Dosages

The pharmaceutical composition may include the 5-HT receptor agonist (including pharmaceutically acceptable salts thereof) contained in a therapeutically effective amount, i.e., in an amount effective to achieve its intended purpose. The actual amount effective for a particular application will depend, inter alia, on the condition being treated. For example, when administered in methods to treat an epilepsy disorder (e.g. Dravet Syndrome), such compositions will contain amounts of the 5-HT receptor agonist (including pharmaceutically acceptable salts thereof) or a pharmaceutical composition thereof effective to achieve the desired result (e.g.

inhibiting seizures).

The dosage and frequency (single or multiple doses) of the 5-HT receptor agonist (including pharmaceutically acceptable salts thereof) or a pharmaceutical composition thereof administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods described herein.

The therapeutically effective amounts of the 5-HT receptor agonist (including pharmaceutically acceptable salts thereof) or a pharmaceutical composition thereof for treating epilepsy diseases described herein may be initially determined from cell culture assays. Target concentrations will be those concentrations of the 5-HT receptor agonist (including pharmaceutically acceptable salts thereof) or a pharmaceutical composition thereof capable of inhibiting or otherwise decreasing seizures experienced by a patient.

Therapeutically effective amounts of the 5-HT receptor agonist (including pharmaceutically acceptable salts thereof) or a pharmaceutical composition thereof for use in humans may be determined from animal models. For example, a dose for humans can be formulated to achieve a concentration that has been found to be effective in animals. The dosage in humans can be adjusted by monitoring response of the patient to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered the 5-HT receptor agonist (including pharmaceutically acceptable salts thereof) or a pharmaceutical composition thereof effective for the particular epilepsy disorder being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of the 5-HT receptor agonist (including pharmaceutically acceptable salts thereof) or a pharmaceutical composition thereof by considering factors such as potency, relative bioavailability, patient body weight, presence and severity of adverse side effects, preferred mode of administration, and the toxicity profile of the selected agent.

Toxicity

The ratio between toxicity and therapeutic effect for a particular compound is its therapeutic index and can be expressed as the ratio between LD50 (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p.1, 1975. The exact formulation, route of administration, and dosage can be chosen by the individual physician in view of the patient's condition and the particular method in which the compound is used.

When parenteral application is needed or desired, particularly suitable admixtures for the 5-HT receptor agonist (including pharmaceutically acceptable salts thereof) included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

EXAMPLES

Example 1

Epilepsy can be acquired as a result of an injury to the brain or genetic mutation.

Among the genetic epilepsies more than 650 variants have been identified in the SCN1A gene (Harkin, L. A. et al. The spectrum of SCN1A-related infantile epileptic encephalopathies. *Brain* 130, 843-852 (2007); Mulley J. C., et al., SCN1A mutations and epilepsy. *Hum. Mutat.* 25, 535-542 (2005)). Missense or frame-shift mutations in this gene are associated with generalized epilepsy with febrile seizures plus (GEFS+) (Ceulemans, B. P., et al., Clinical correlations of mutations in the SCN1A gene: from febrile seizures to severe myoclonic epilepsy in infancy. *Pediatric Neurol.* 30, 236-243 (2004)) as well as a more severe disorder known as Dravet syndrome. Children with DS initially exhibit normal development but often experience febrile seizure episodes within the first year of life with eventual progression to severe spontaneous recurrent seizures, intellectual disability, ataxia, and psychomotor dysfunction. Seizures are inadequately managed using available antiepileptic drugs (AEDs) and these children are poor candidates for neurosurgical resection (Bender, A. C., et al., SCN1A mutations in Dravet syndrome: Impact of interneuron dysfunction on neural networks and cognitive outcome. *Epilepsy Beh.* 23, 177-186 (2012)).

In mammalian brain there are four main subtypes of voltage-gated sodium channel alpha subunits: $Na_V1.1$, $Na_V1.2$, $Na_V1.3$ and $Na_V1.6$, encoded for by the genes SCN1A, SCN2A, SCN3A, and SCN8A, respectively. Opening of these channels produces a sodium conductance and rapid cell membrane depolarization e.g., features integral to action potential initiation (Catterall, W. A., et al., $Na_V1.1$ channels and epilepsy. *J. Physiol.* 588, 1849-1859 (2010)). In mice, $Na_V1.1$ is widely expressed in the central nervous system including the axon initial segment of parvalbumin-positive hippocampal interneurons and excitatory principal cells (Kim, D. Y., et al., Reduced sodium channel Na(v)1.1 levels in BACE1-null mice. *J. Biol. Chem.* 286, 8106-8116 (2011); Chen, C., et al., Mice lacking sodium channel beta1 subunits display defects in neuronal excitability, sodium channel expression, and nodal architecture. *J. Neurosci.* 24, 4030-4042 (2004)). Heterozygous deletion of $Na_V1.1$ in mice leads to a reduction in the firing capability of acutely dissociated fast-spiking interneurons (Yu, F. H., et al., Reduced sodium current in GABAergic interneurons in a mouse model of severe myoclonic epilepsy in infancy. *Nat. Neurosci.* 9, 1142-1149 (2006)). Mice with global or interneuron-specific heterozygous deletion of $Na_V1.1$ exhibit temperature-induced and spontaneous seizures, mild ataxia, autism-like behaviors and premature death (Yu, F. H., et al., Reduced sodium current in GABAergic interneurons in a mouse model of severe myoclonic epilepsy in infancy. *Nat. Neurosci.* 9, 1142-1149 (2006); Oakley, J. C., et al., Temperature- and age-dependent seizures in a mouse model of severe myoclonic epilepsy in infancy. *Proc. Natl. Acad. Sci. USA* 106, 3994-3999 (2009); Cheah, C. S., et al., Specific deletion of $Na_V1.1$ sodium channels in inhibitory interneurons causes seizures and premature death in a mouse model of Dravet syndrome. *Proc. Natl. Acad. Sci. USA* 109, 14646-14651 (2012)). Knock-in mouse carrying a premature stop codon in domain III of the Na$_v$1.1 channel also exhibit a decrement in spike amplitude during prolonged interneuron firing and increased sensitivity to temperature-induced seizures (Ogiwara, I., et al., Na$_v$1.1 localizes to axons of parvalbumin-positive inhibitory interneurons: a circuit basis for epileptic seizures in mice carrying an Scn1a gene mutation. *J. Neurosci.* 27, 5903-5914 (2007)).

Generation and characterization of valid animal models is critical to efforts to understand the pathophysiology of DS, and to aid in identification of novel therapies. While considerable attention has focused on modeling SCN1A mutations in mice these animals have proven difficult to breed and epilepsy phenotypes are strongly influenced by background strain genetics. Induced pluripotent stem cells can be generated from DS patients but individual neurons do not recapitulate the network environment necessary for in vivo seizure generation. *Danio rerio* (zebrafish), a simple vertebrate species, provide an alternative model system with significant advantages for genetic manipulation, cost-efficient breeding and in vivo drug discovery (Lessman, C. A., The developing zebrafish (Danio rerio): a vertebrate model for high-throughput screening of chemical libraries. *Birth Defects Res. C. Embryo Today* 93, 268-280 (2011); Delvecchio, C., et al., The zebrafish: a powerful platform for in vivo, HTS drug discovery. *Assay Drug Dev. Technol.* 9, 354-361 (2011); Rinkwitz, S., et al., Zebrafish: an integrative system for neurogenomics and neurosciences. *Prog. Neurobiol.* 93, 231-243 (2011)).

Ideally, an animal model should be based on a known genetic cause of the disease (SCN1A mutation), accurately recapitulate key features of the disease (epilepsy), and respond, or not, to therapies commonly used in patients with the disease (pharmacological validation). If successful, such a model could inform the understanding of the disease process and catalyze explorations toward new therapies.

Figure 1B:
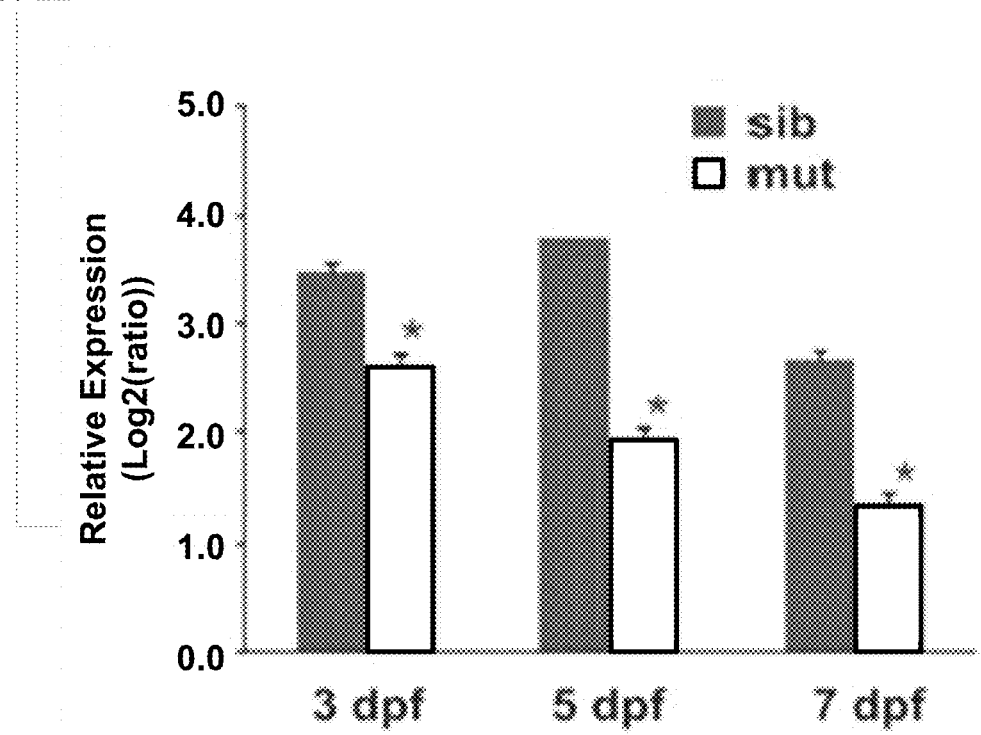
Figure 1C:
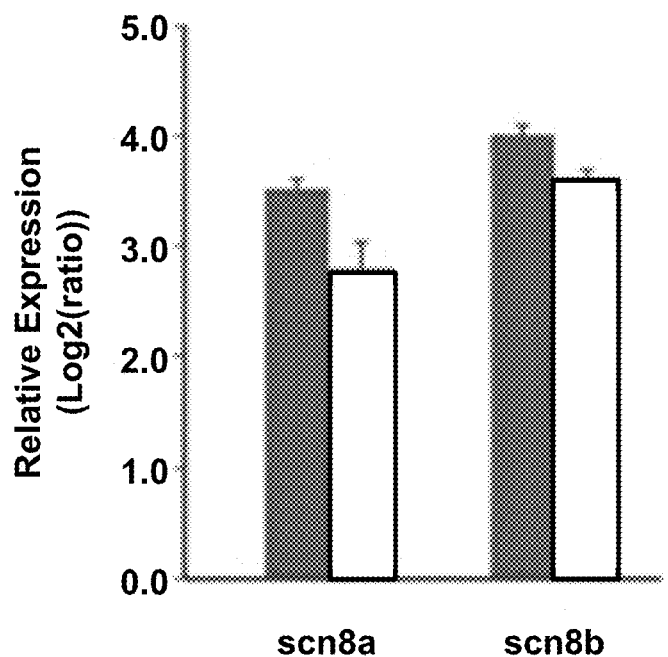
Figure 1D:
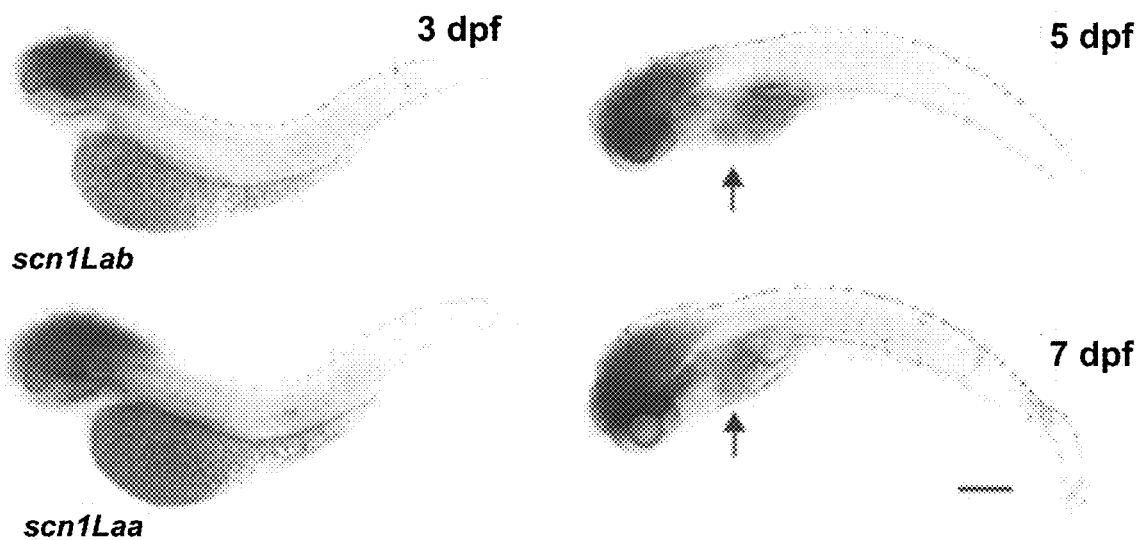
Figure 1E:
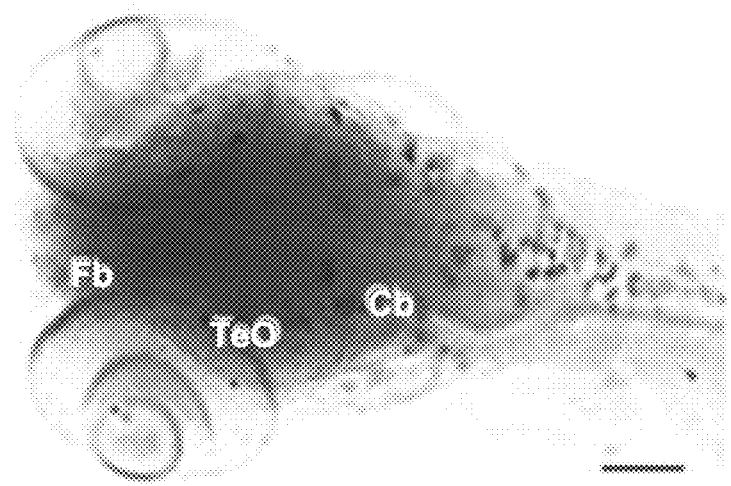

In zebrafish, the voltage-gated sodium channel family consists of four sets of duplicated genes: scn1Laa & scn1Lab, scn4aa & scn4ab, scn5Laa & scn5Lab, and scn8aa & scn8ab (Novak, A. E., et al., Embryonic and larval expression of zebrafish voltage-gated sodium channel alpha-subunit genes. *Dev. Dyn.* 235, 1962-1973 (2006)). The zebrafish scn1Lab gene shares a 77% identity with human SCN1A and is expressed in the central nervous system. A homozygous zebrafish mutant for this gene (originally termed didy$^{s552}$) was discovered in a chemical mutagenesis screen using the optokinetic response as an assay (Schoonheim, P. J., Arrenberg, A. B., Del Bene, F., & Baier H., Optogenetic localization and genetic perturbation of saccade-generating neurons in zebrafish. *J. Neurosci.* 30, 7111-7120 (2010)). These types of screens are based on inducing random point mutations using the alkylating agent N-ethyl-N-nitrosourea (ENU), resulting mutations are typically loss-of-function and recessive. Although this is a homozygous mutation, scn1Lab zebrafish mutants are relevant for the autosomal dominant human Dravet Syndrome given the genome duplication in zebrafish and the presence of an additional Na$_v$1.1 homologue (scn1Laa). scn1Lab mutants were characterized at the molecular and behavioral level, demonstrated that mutants exhibit spontaneous drug-resistant seizures, and then used them in a novel high-throughput screening program to identify compounds that ameliorate the epilepsy phenotype. A phenotype-based screen identified clemizole, an FDA-approved compound, as an effective inhibitor of spontaneous convulsive behaviors and electrographic seizures in these mutants.

scn1Lab expression and characterization of mutant zebrafish. Zebrafish with a mutation in domain III of a voltage-gated sodium channel were identified by Dr. Herwig Baier during a chemical mutagenesis screen (Schoonheim, P. J., Arrenberg, A. B., Del Bene, F., & Baier H., Optogenetic localization and genetic perturbation of saccade-generating neurons in zebrafish. *J. Neurosci.* 30, 7111-7120 (2010)). Original scn1Lab mutants were backcrossed onto the Tupfel long (TL) background for 7-10 generations and confirmed a methionine (M) to arginine (R) mutation in the colony (FIG. 1A). Reverse transcriptase (RT) and quantitative (q) PCR revealed a decrease in mRNA expression for scn1Lab in mutant larvae at 3, 5 and 7 days post-fertilization (dpf) (FIG. 1B); antibodies recognizing this protein in zebrafish are not available. As expected (Novak, A. E., et al., Embryonic and larval expression of zebrafish voltage-gated sodium channel alpha-subunit genes. *Dev. Dyn.* 235, 1962-1973 (2006)), scn1Lab is prominently expressed during early stages of larval development (FIG. 1B) and specifically in the central nervous system at 3 dpf (FIGS. 1D, E). Whole-mount in situ hybridization revealed diffuse but prominent expression in brain regions corresponding to forebrain (telencephalon), optic tectum and cerebellum. A similar expression pattern was observed for scn1Laa at 3 dpf. At 5 and 7 dpf, CNS expression remained prominent and faint scn1Lab signal was also noted in the heart (FIG. 1D). Relative expression of scn8aa or scn8ab (Na$_v$1.6) e.g., a subunit thought to act as a genetic modifier of DS (Martin, M. S., et al., The voltage-gated sodium channel Scn8a is a genetic modifier of severe myoclonic epilepsy of infancy. *Hum. Mol. Gen.* 16, 2892-2899 (2007)), failed to reveal a significant difference in expression between mutants and sibling controls at 5 dpf (FIG. 1C). Similarly, microarray analysis at 5 dpf also failed to detect a compensatory change in the mRNA expression of thirteen different zebrafish scn subunits (Table I) including the other homolog (scn1Laa). These results demonstrate a selective defect in a zebrafish Na$_v$1.1 gene expressed in the CNS during early development.

Figure 2A:
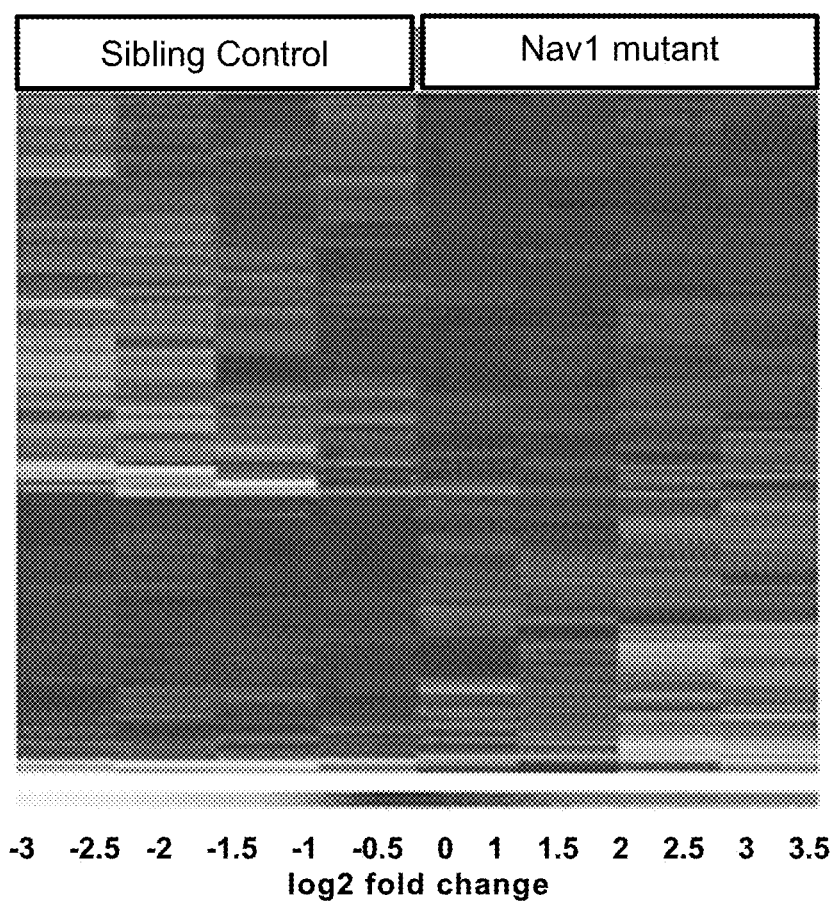
FIGS. 2A-2C. Microarray analysis of scn1Lab zebrafish mutants.
Figure 2B:
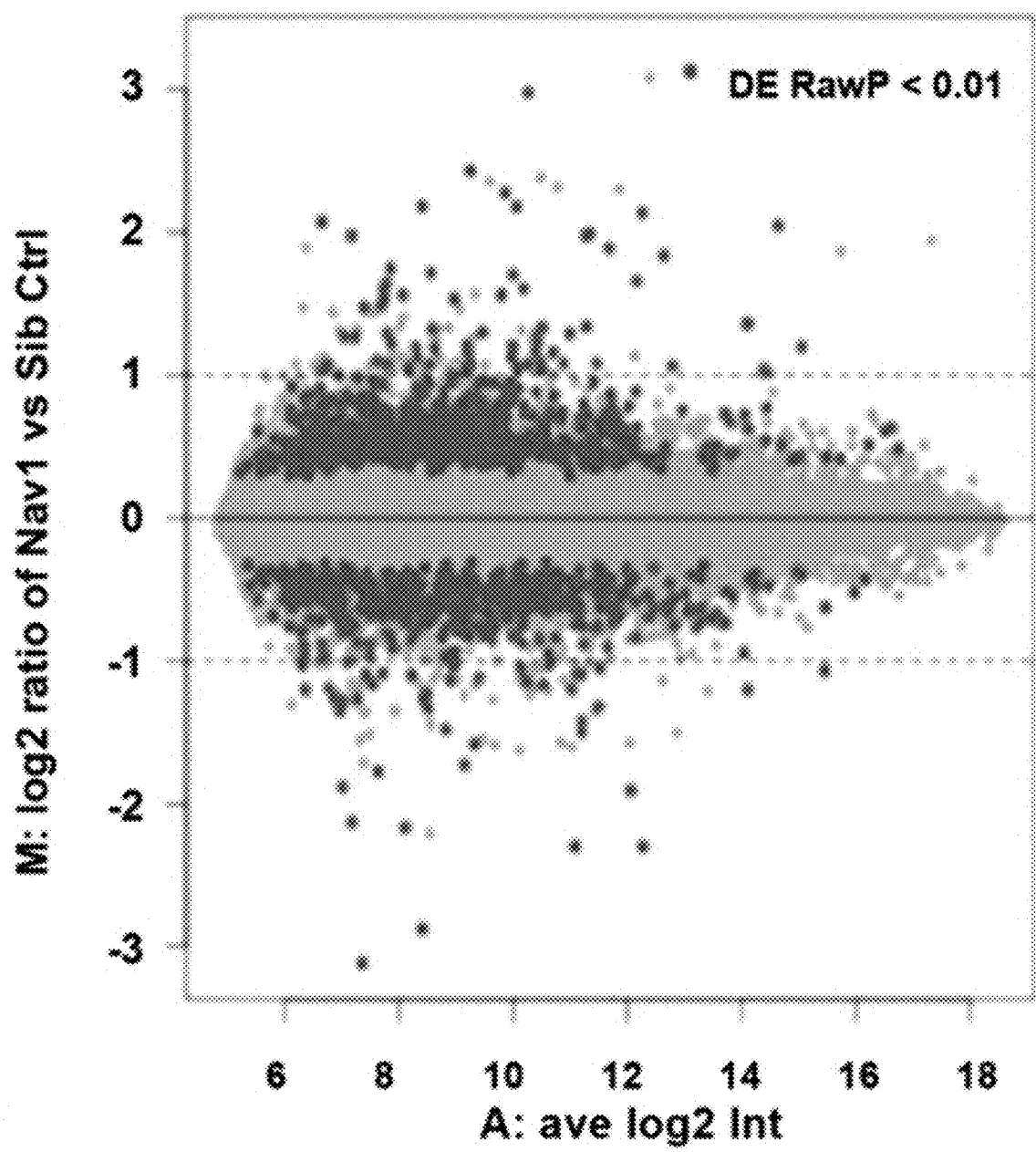
Figure 2C:
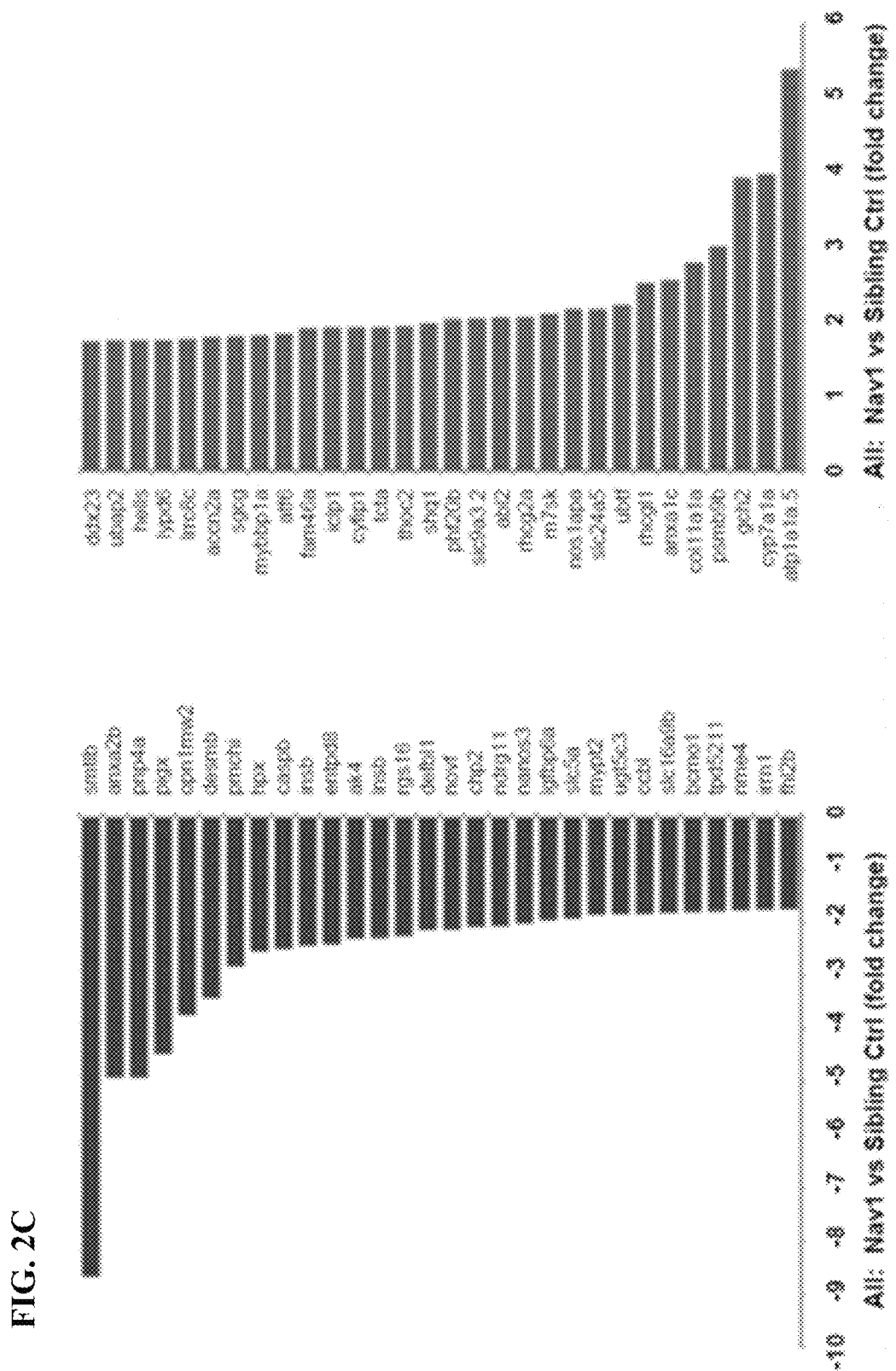

Large-scale transcriptomic analysis of scn1Lab mutants. Although inherited disorders of voltage-gated ion channels are recognized as an etiology of epilepsy, investigation of transcriptional changes has not been reported for any epilepsy-related channelopathy. To detect differences in gene expression in an unbiased manner an Agilent Danio rerio chip covering 44,000 probes (FIGS. 2A, B) was used. Hierarchical clustering analyses showed that ~2.5% (1099) of these probes were differentially expressed between mutants and sibling controls at 5 dpf (p<0.01, t test; 674 up-regulated and 425 down-regulated); 405 were assigned to an "unknown function" category. A list of 30 down- and up-regulated known genes showing the greatest differences in expression is shown in FIG. 2C. These differences were modest as 90% (990/1099) of the identified genes exhibited fold-changes between 0.8 and 2.0. Similar to microarray analysis of Mecp2 single- gene mutant mice (Jordan, C., et al., Cerebellar gene expression profiles of mouse models for Rett syndrome reveal novel MeCP2 targets. *BMC Med. Genet.* 8, 36 (2007)), many of the genes identified had no obvious CNS-related function and/or expression.

Figure 3A:
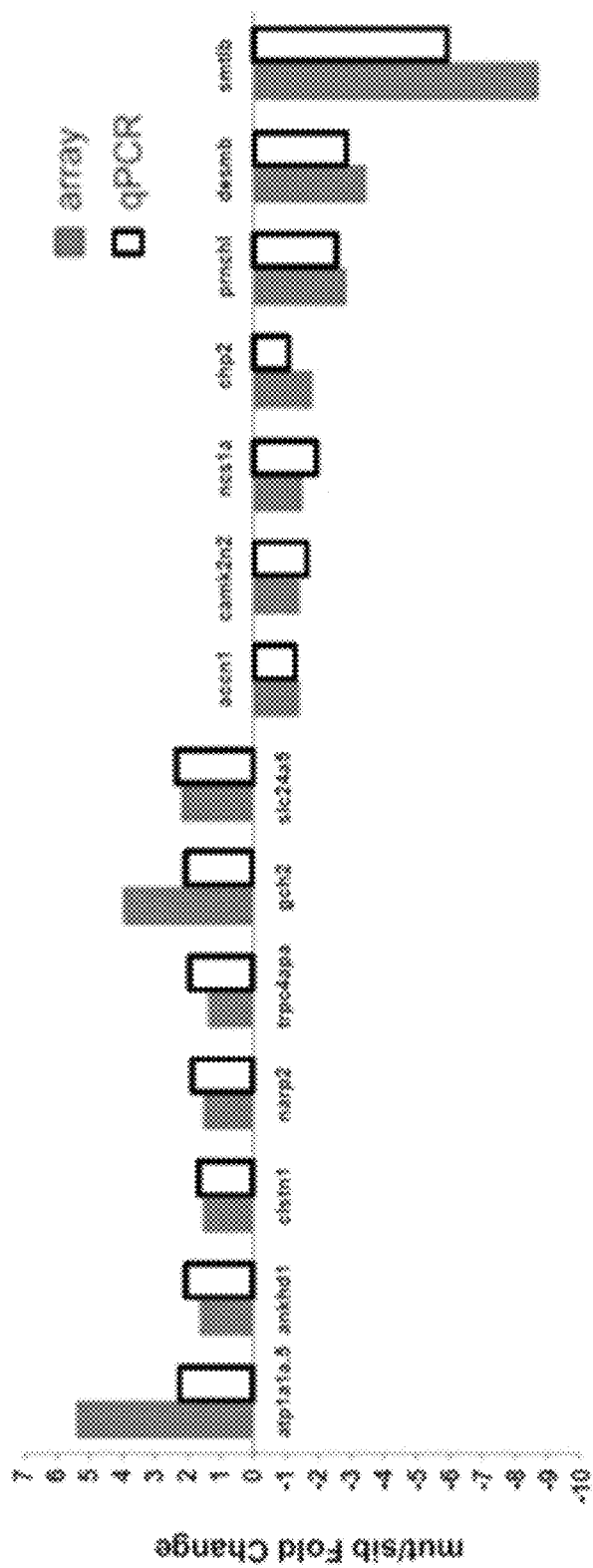
FIGS. 3A-3C. Quantitative RT-PCR analysis of scn1Lab zebrafish mutants.

The two largest fold-changed genes, somatolactin β and a Na, K-ATPase, have expression primarily restricted to the pituitary (smt1b) (Lopez, M., et al., Expression of the somatolactin β gene during zebrafish embryonic development. *Gene Expr. Patterns* 6, 156-161 (2006)) or ear, intestinal bulb and pronephric duct (atp1a1a.5) (Blasiole, B., et al., Cloning, mapping, and developmental expression of a sixth zebrafish Na, K-ATPase alpha1 subunit gene (atp1a1a.5). *Mech. Dev.* 119, Suppl 1:S211-S214 (2002)). Probes for several genes related to apoptosis (casp8, casp8b and casp3b) did not reveal any statistically significant changes in the microarray studies. Of the genes with altered expression in scn1Lab mutants, six were previously implicated in neurological disorders e.g., pcdh19 (infantile epileptic encephalopathy), cyfip1 and fxr2 (Fragile X syndrome), ocr1 (Lowe syndrome), ubap21 (Parkinson's disease) and oca2 (Angelman syndrome). Microarray-based gene expression measurements were verified for 14 randomly selected genes using qPCR (FIG. 3A).

Figure 3B:
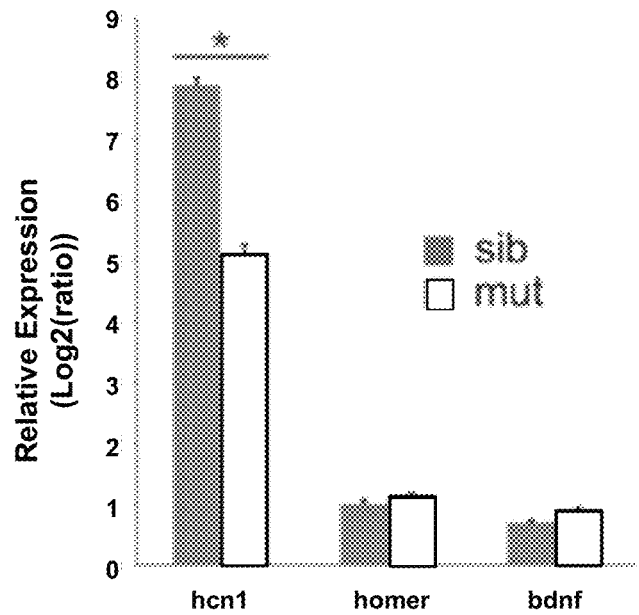
Figure 3C:
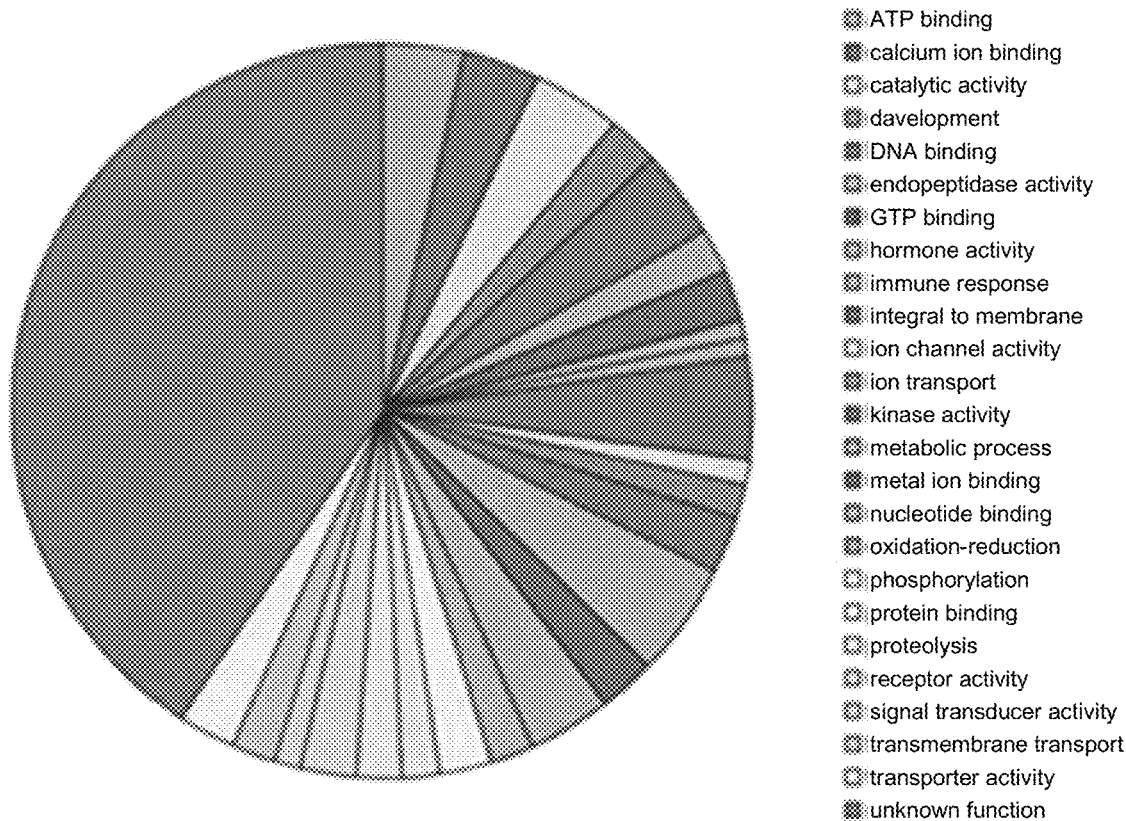

Biological functions were assigned to all genes using gene ontology (GO) annotations and the 482 genes showing at least a 1.5-fold change in expression and ap value<0.01 were categorized further (FIG. 3C). Calcium ion binding genes include annexinA1c, A1b and 2a, spectrin a2, neurexin 2a, calsyntenin 1 and parvalbumin 3. Significant changes in a gap junction channel (cx43), a gene involved in clustering of voltage-gated sodium channels at the axon initial segment (spna2) and the ubiquitin domain of a GABA receptor (map1lc3b) were also noted. Three additional genes not found on the microarray were chosen for qPCR analysis (FIG. 3B): hcn1, a gene shown to be correlated with SCN1A using data mining and down-regulated in several seizure models (Noam, Y., et al., Towards an integrated view of HCN channel role in epilepsy. Curr. Opin. Neurobiol. 21, 873-879 (2011)) was significantly reduced in scn1Lab mutants compared to sibling control (p<0.05 2-tail Student's t-test). However, homer and bdnf e.g., genes involved in synaptogenesis related to the formation of recurrent excitatory synapses and epilepsy (Avedissian, M., et al., Hippocampal gene expression analysis using the ORESTES methodology shows that homer 1a mRNA is upregulated in the acute period of the pilocarpine epilepsy model. Hippocampus 17, 130-136 (2007); Tongiorgi, E., et al., Brain-derived neurotrophic factor mRNA and protein are targeted to discrete dendritic laminas by events that trigger epileptogenesis. J. Neurosci. 24, 6842-6852 (2004)) were unchanged.

Figure 4A:
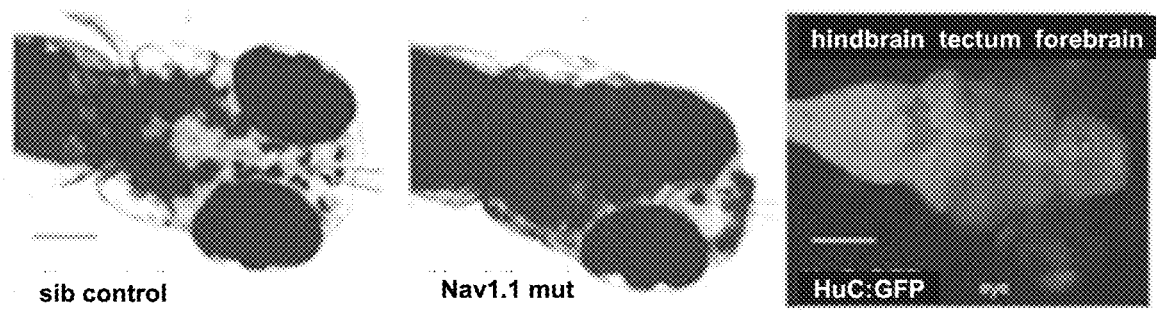
FIGS. 4A-4C. Spontaneous seizures in scn1Lab zebrafish mutants.

Spontaneous seizures in scn1Lab mutant zebrafish. scn1Lab mutants were monitored for evidence of spontaneous electrographic seizures starting at 3 dpf e.g., the first larval stage at which epileptiform discharge can be detected (Baraban, S. C., et al., A large-scale mutagenesis screen to identify seizure-resistant zebrafish.Epilepsia 48, 1151-157 (2007); Hortopan, G. A., et al., Spontaneous seizures and altered gene expression in GABA signaling pathways in a mind bomb mutant zebrafish. J. Neurosci. 30, 13718-13728 (2010); Hunt, R. F., Hortopan, G. A., Gillespie, A., & Baraban, S. C., A novel zebrafish model of hyperthermia-induced seizures reveals a role for TRPV4 channels and NMDA-type glutamate receptors. Exp. Neurol. 237, 199-206 (2012); Baraban, S. C., Taylor, M. R., Castro, P. A., & Baier H., Pentylenetetrazole induced changes in zebrafish behavior, neural activity and c-fos expression. Neuroscience 131, 759-768 (2005); Chege, S. W., Hortopan, G. A., Dinday, M. T., & Baraban, S. C., Expression and function of KCNQ channels in larval zebrafish. Dev. Neurobiol. 72, 186-198 (2012)). Mutant larvae were identified by their "black" appearance (FIG. 4A), which is indicative of a defect in pigment aggregation and die prematurely between 10 and 12 dpf, as reported previously (Novak, A. E., et al., Embryonic and larval expression of zebrafish voltage-gated sodium channel alpha-subunit genes. Dev. Dyn. 235, 1962-1973 (2006)). Forebrain extracellular field recordings from paralyzed and agar-immobilized scn1Lab mutants were marked by frequent brief interictal-like bursts and large-amplitude long duration ictal-like events starting at 3 dpf (n=4) and progressively becoming more prominent between 4 and 7 dpf (n=132) (FIG. 2C). These events were confirmed in 100% of mutants at 3 dpf, 100% at 4 dpf, 97% at 5 dpf, 98% at 6 dpf and 100% at 7 dpf.

Figure 4B:
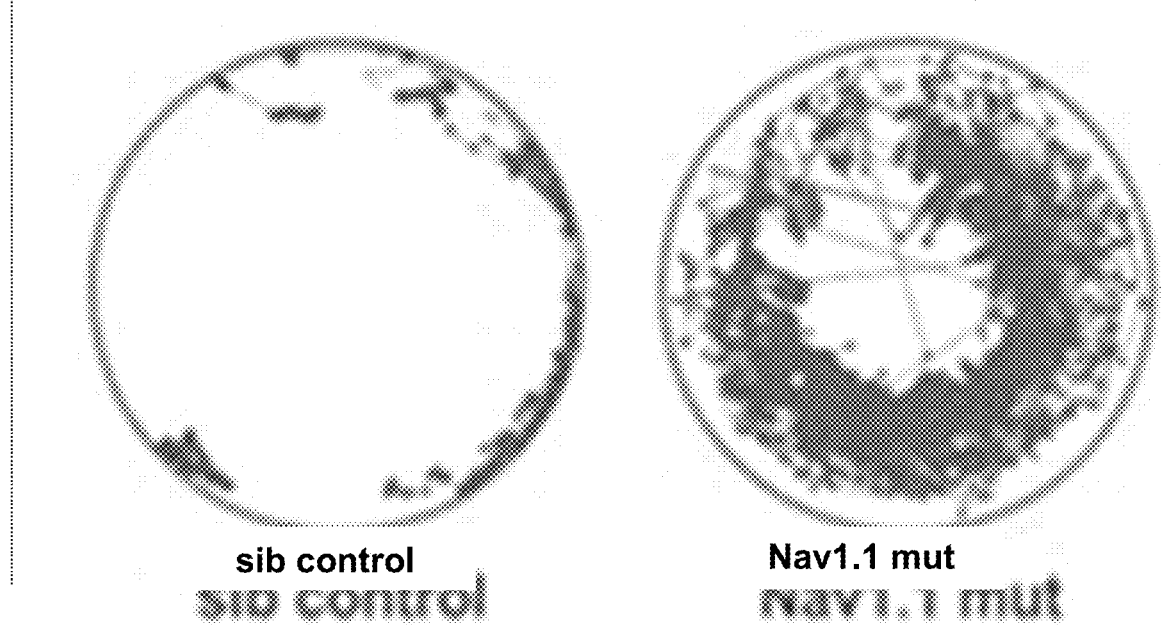
Figure 4C:
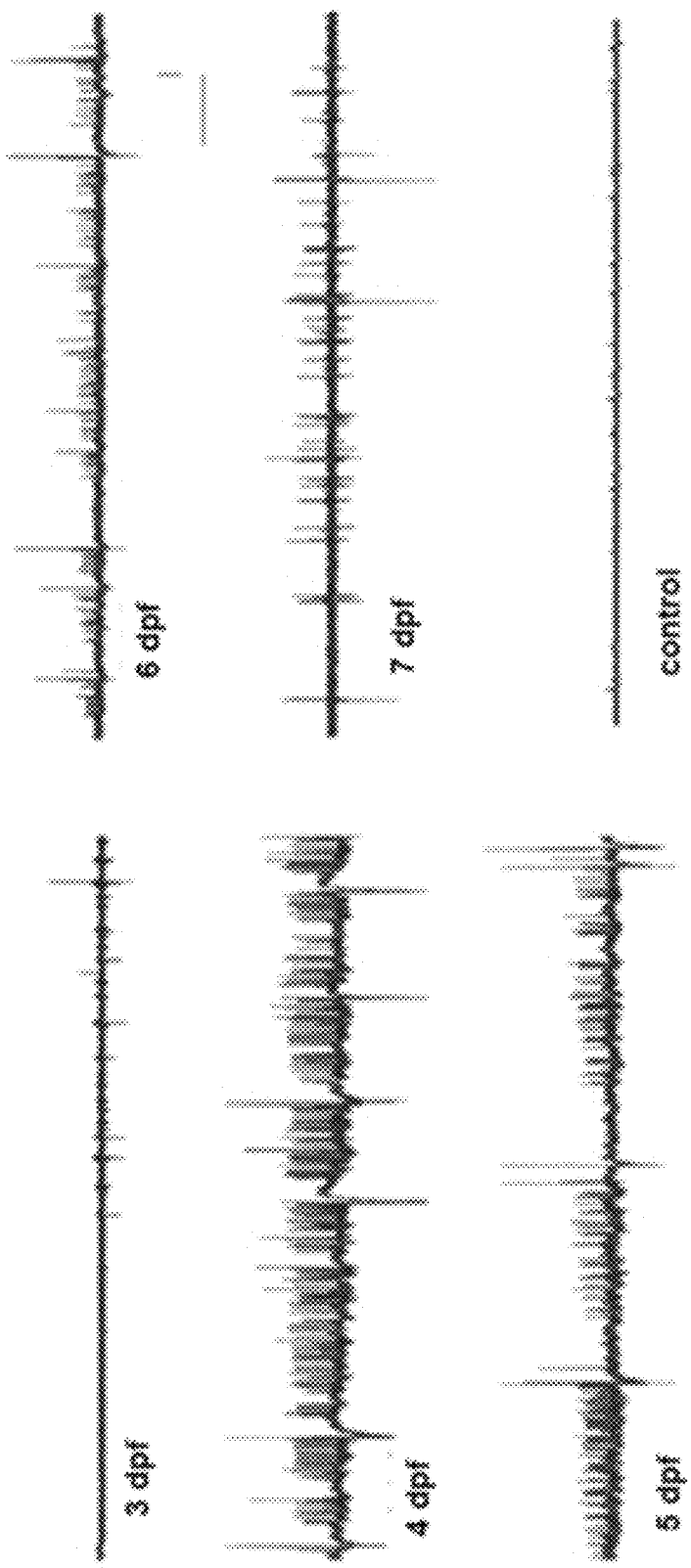

Abnormal electrical events were not observed in age-matched sibling controls at any developmental stage (n=36). Hyperthermia-induced seizures (Hunt, R. F., Hortopan, G. A., Gillespie, A., & Baraban, S. C., A novel zebrafish model of hyperthermia-induced seizures reveals a role for TRPV4 channels and NMDA-type glutamate receptors. Exp. Neurol. 237, 199-206 (2012)) could be evoked in 5 dpf scn1Lab mutants and controls at apparently similar temperature thresholds (mutant: 26.9±0.5 C.°; n=14; control: 25.9±0.5 C.°; n=14;p=0.164 t-test). However, these measurements were complicated, in mutants, by simultaneous occurrence of high frequency spontaneous epileptiform discharges. Mutants had elevated levels of swim activity and exhibited unprovoked seizure-like behavior consisting of whole-body convulsions and rapid undirected movement starting at 4 dpf (n=36). A representative locomotion tracking plot of a scn1Lab mutant showing hyperactivity and convulsive behavior is shown in FIG. 4B. This behavior is similar to that classified as a Stage III seizure in larvae exposed to pentylenetetrazole (Baraban, S. C., Taylor, M. R., Castro, P. A., & Baier H., Pentylenetetrazole induced changes in zebrafish behavior, neural activity and c-fos expression. Neuroscience 131, 759-768 (2005)). Seizure behaviors were never observed in controls at any stage of development (n=36). In pools of mutant and sibling control larvae, scn1Lab mutants stay close to the sides of the petri dish, which is considered a form of thigmotaxis in fish (Ellis, L. D., Seibert, J., & Soanes, K. H., Distinct modes of induced hyperactivity in zebrafish larvae. Brain Res. 1449, 46-59 (2012)). These results reveal a striking epilepsy phenotype in scn1Lab mutant zebrafish.

Figure 5A:
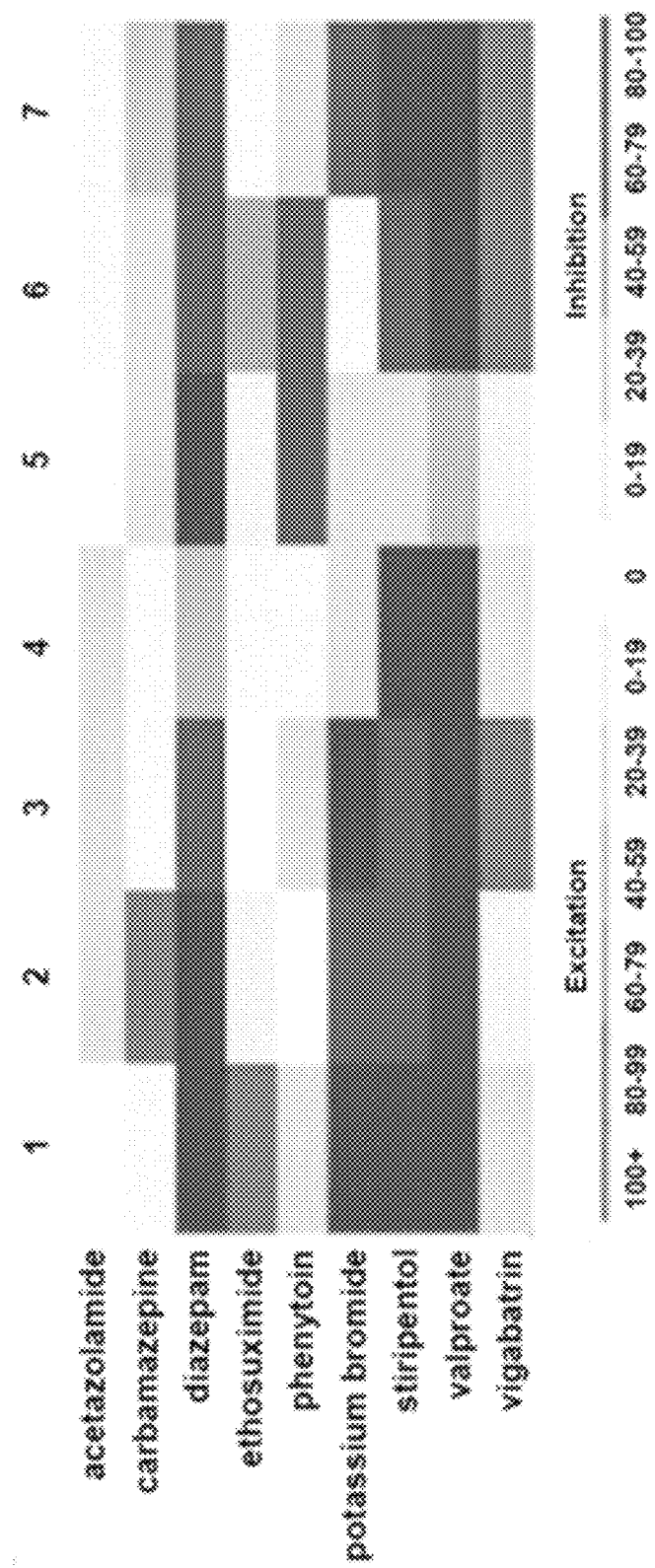
FIGS. 5A-5F. Pharmacological validation of scn1Lab zebrafish mutants.
Figure 5B:
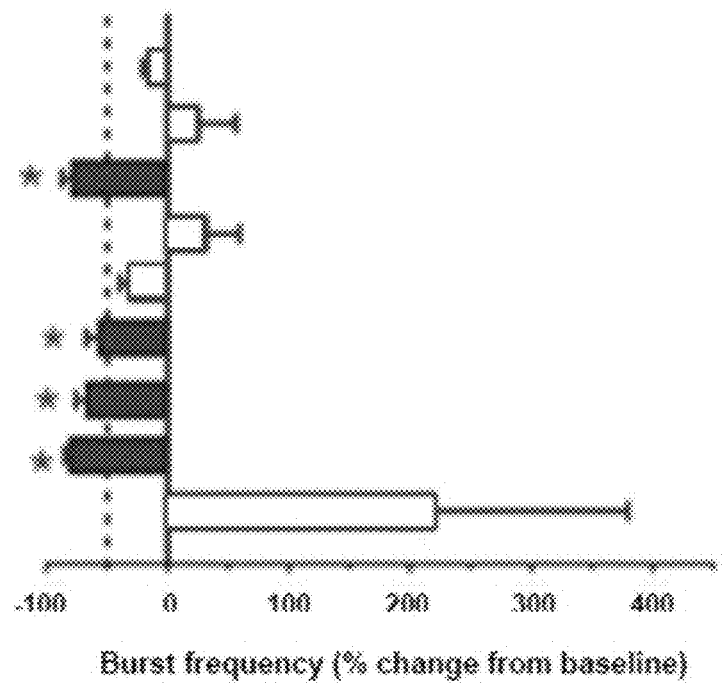
Figure 5C:
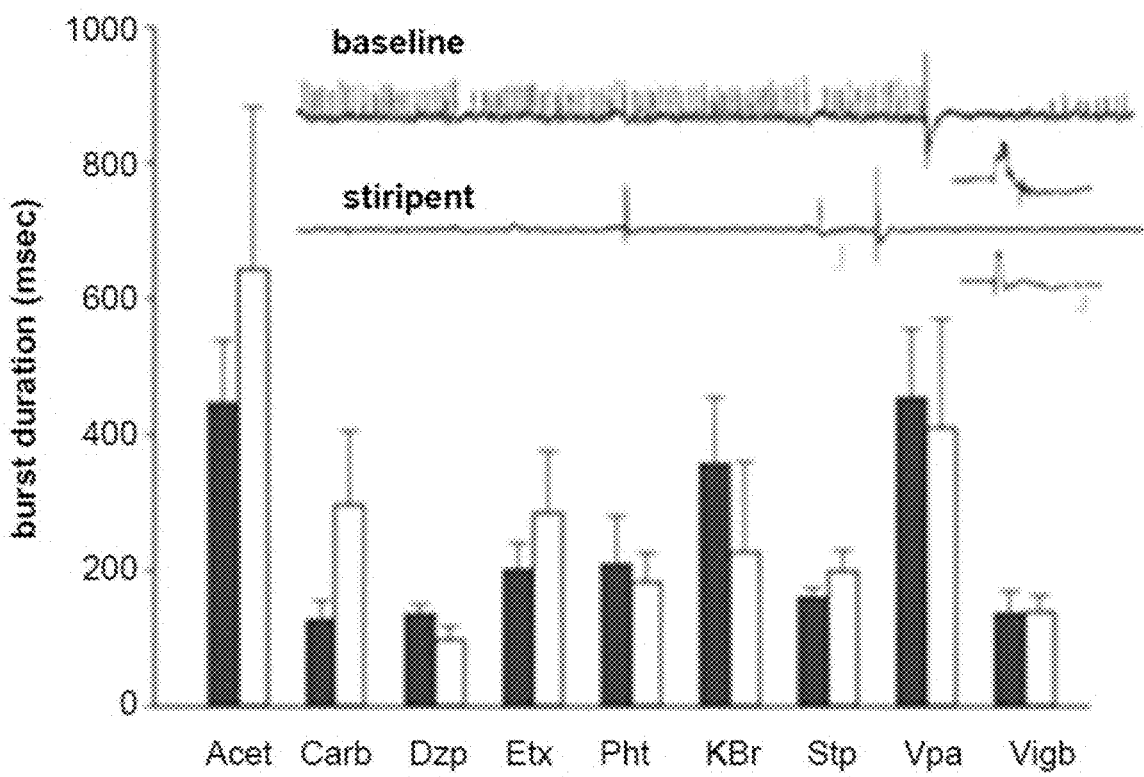
Figure 5D:
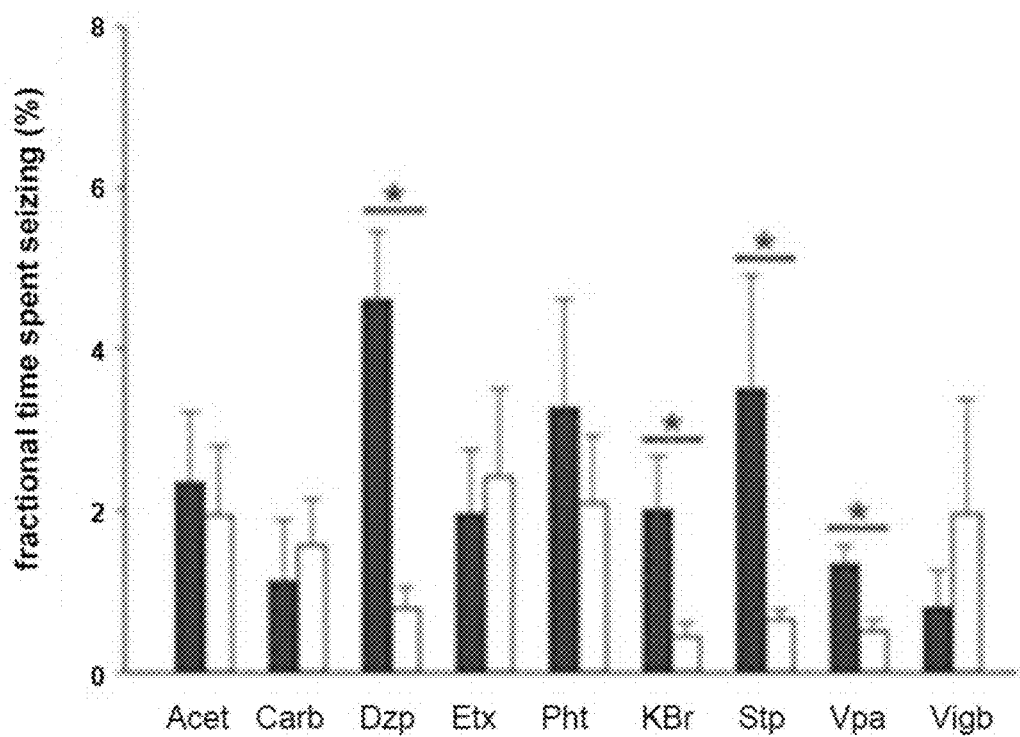
Figure 5E:
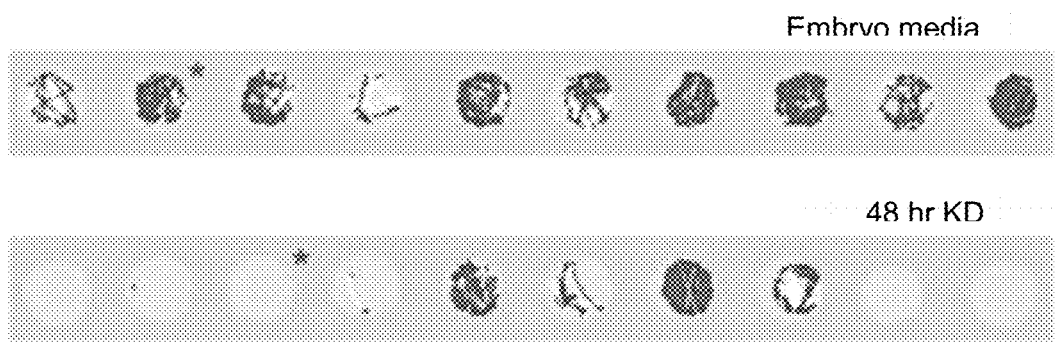

Pharmacological evaluation of scn1Lab mutant zebrafish. Seizures associated with SCN1A mutations are poorly responsive to most AEDs. To evaluate pharmaco-sensitivity spontaneous electrographic seizures were recorded in agar-embedded scn1Lab mutants (5-6 dpf) under baseline conditions, and again after application of a commercially available AED. All drugs were bath applied at a concentration of 1 mM; seven fish were tested for each drug. Epileptiform event frequency (including interictal- and ictal-like discharges) and the fractional time spent seizing in scn1Lab mutants were reduced by valproate, diazepam, potassium bromide and stiripentol (FIGS. 5A, B, D). Burst durations were not significantly changed for any of these drug exposures (FIG. 5C).

Figure 5F:
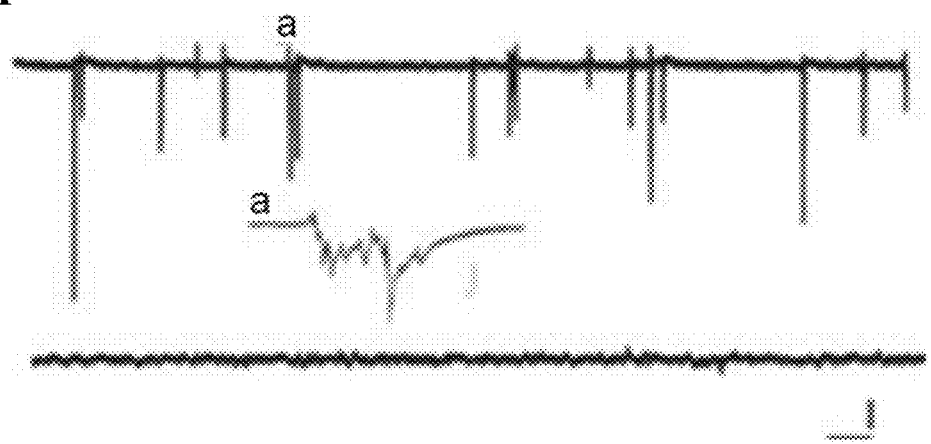

As expected, most AEDs had no effect and epileptiform activity became more frequent following exposure to carbamazepine (in 2 of 7 fish), ethosuximide (4 of 7 fish) or vigabatrin (6 of 7 fish). Because DS children often respond to the ketogenic diet (KD) (Dravet, C., et al., Severe myoclonic epilepsy in infancy: Dravet syndrome. Adv. Neurol. 95, 71-102 (2005)) a separate clutch of scn1Lab mutants was exposed, siblings and WT controls to a form of the diet for 48 hr starting at 4 dpf. Locomotion tracking data on KD-exposed larvae at 6 dpf confirm a reduction in seizure-like behavior to control levels in 7 of 10 mutants (Fig. E; mean velocity, treated mutants=0.43±0.09 mm/sec, n=16; un-treated mutants=0.81±0.05 mm/sec, n=28; p<0.05 Kruskal-Wallis ANOVA on Ranks with a Dunn's pairwise multiple comparison). No significant differences in swim behavior were noted in sibling controls treated with the KD (mean velocity=0.63±0.05 mm/sec, n=20) compared to un-treated WT larvae at 6 dpf (mean velocity=0.62±0.07 mm/sec; n=20). Acute exposure (20 min) to the diet had no effect on mutant seizure behavior in the locomotion assay (n=14; change in mean velocity<34%). Subsequent forebrain field recordings obtained from the same zebrafish used in the locomotion assay (FIG. 5F, top trace) confirmed the occurrence of spontaneous epileptiform discharge for embryo media exposed scn1Lab mutants and a suppression of burst activity in mutants exposed to the KD for 48 hr (FIG. 5F, bottom trace). These results demonstrate that the pharmacological profile for scn1Lab mutants resembles that seen in children with DS.

High-throughput drug screening in scn1Lab mutants. Because behavioral seizure activity is easily and rapidly monitored using a locomotion tracking format (Baraban, S. C., et al., A large-scale mutagenesis screen to identify seizure-resistant zebrafish. Epilepsia 48, 1151-157 (2007); Hortopan, G. A., et al., Spontaneous seizures and altered gene expression in GABA signaling pathways in a mind bomb mutant zebrafish. J. Neurosci. 30, 13718-13728 (2010); Baraban, S. C., Taylor, M. R., Castro, P. A., & Baier H., Pentylenetetrazole induced changes in zebrafish behavior, neural activity and c-fos expression. *Neuroscience* 131, 759-768 (2005); Chege, S. W., Hortopan, G. A., Dinday, M. T., & Baraban, S. C., Expression and function of KCNQ channels in larval zebrafish. *Dev. Neurobiol.* 72, 186-198 (2012); Berghmans, S., Hunt, J., Roach, A., & Goldsmith, P., Zebrafish offer the potential for a primary screen to identify a wide variety of potential anticonvulsants. *Epilepsy Res.* 75, 18-28 (2007); Baxendale, S., et al., Identification of compounds with anti-convulsant properties in a zebrafish model of epileptic seizures. *Dis. Model. Mech.* 5, 773-774 (2012); Cario, C. L., Farrell, T. C., Milanese, C., & Burton, E. A., Automated measurement of zebrafish larval movement. *J. Physiol.* 589, 3703-3708 (2011); Winter, M. J., et al., Validation of a larval zebrafish locomotor assay for assessing the seizure liability of early-stage development drugs. *J. Pharm. Tox. Methods* 5, 176-187 (2008); Orellana-Paucar, A. M., et al., Anticonvulsant activity of bisabolene sesquiterpenoids of Curcuma longa in zebrafish and mouse seizure models. *Epilepsy Beh.* 24, 14-22 (2012) (FIGS. 4B and 5B1).

A high-throughput phenotype-based strategy was designed to screen chemical libraries for compounds that reduce mutant behavior to Stage 0 (very little swim activity) or Stage I (increased, but non-convulsive, swim activity) e.g., behavior equivalent to that seen in normal WT mutants. Automated measurement of larval activity was achieved using EthoVision tracking software (Noldus Information Technology) and a high-speed camera. Previous studies confirmed that high velocity movement≥20 mm/sec correspond to paroxysmal seizure-like convulsions (Stage III) (Winter, M. J., et al., Validation of a larval zebrafish locomotor assay for assessing the seizure liability of early-stage development drugs. *J. Pharm. Tox. Methods* 5, 176-187 (2008); Orellana-Paucar, A. M., et al., Anticonvulsant activity of bisabolene sesquiterpenoids of Curcuma longa in zebrafish and mouse seizure models. *Epilepsy Beh.* 24, 14-22 (2012)).

Figure 6A:
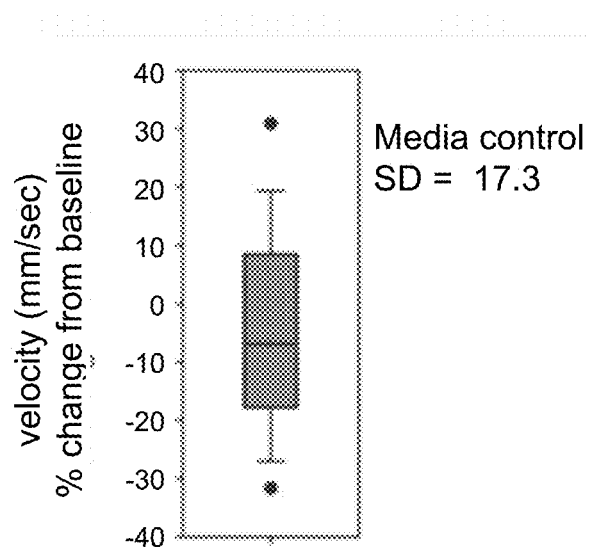
FIGS. 6A-6E. A screen to identify drugs that rescue the scn1Lab mutant epilepsy phenotype.
Figure 6B:
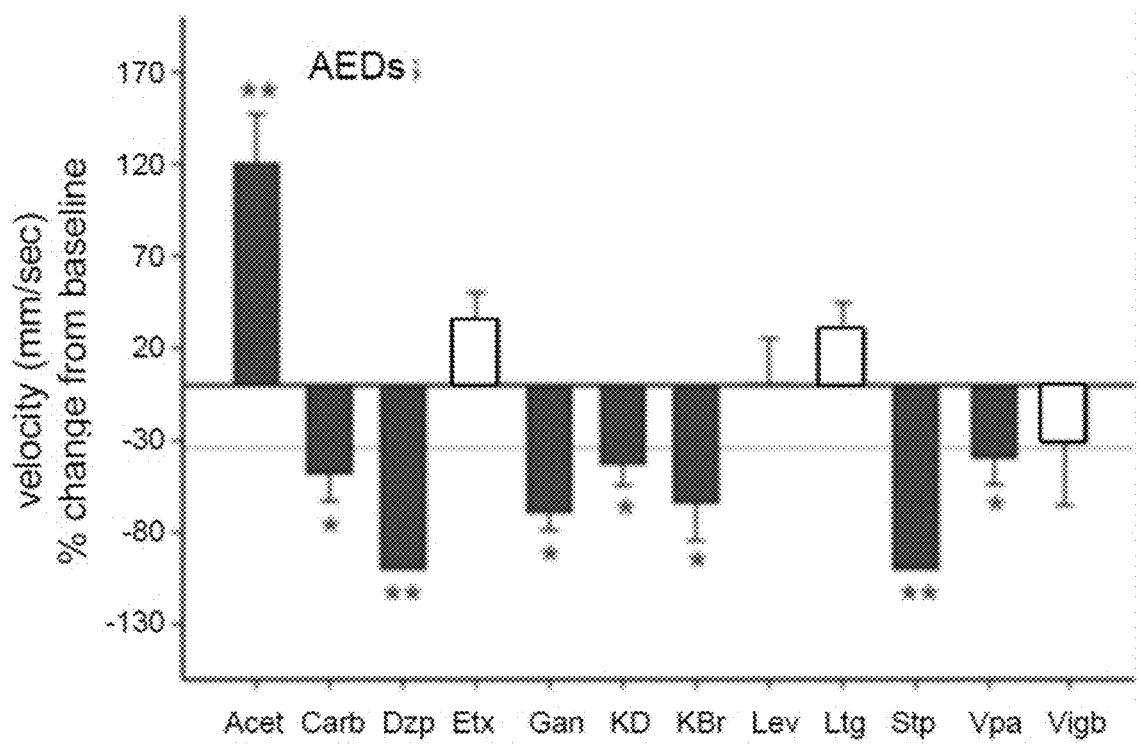

Using a 96-well format, mutant swim activity at baseline was automatically tracked, and then again after addition of a test compound (100 µl); each compound was tested on 6 to 12 individual larvae at 5 dpf. The change in mutant swim activity between two consecutive recording epochs in embryo media was taken as baseline and is shown in FIG. 6A (n=28). Based on a standard deviation of 17.3 for baseline recordings associated simply with a solution exchange, compounds that inhibited movement (measured as a change in mean velocity) by ≥34% were screened for. To validate this approach, eleven AEDs and the KD were first screened using this assay. As expected from electrophysiological assays (FIG. 5), diazepam, potassium bromide, stiripentol, valproate and a 48 hr exposure to KD effectively inhibited seizure behavior in the locomotion-based assay (FIG. 6B); ganaxolone, a neuroactive steroid related to allopregnalone, was also effective. Next, test compounds were screened at an initial concentration of 667 µM from a library that included US Food and Drug Administration (FDA) approved and toxicology tested drugs.

Figure 6C:
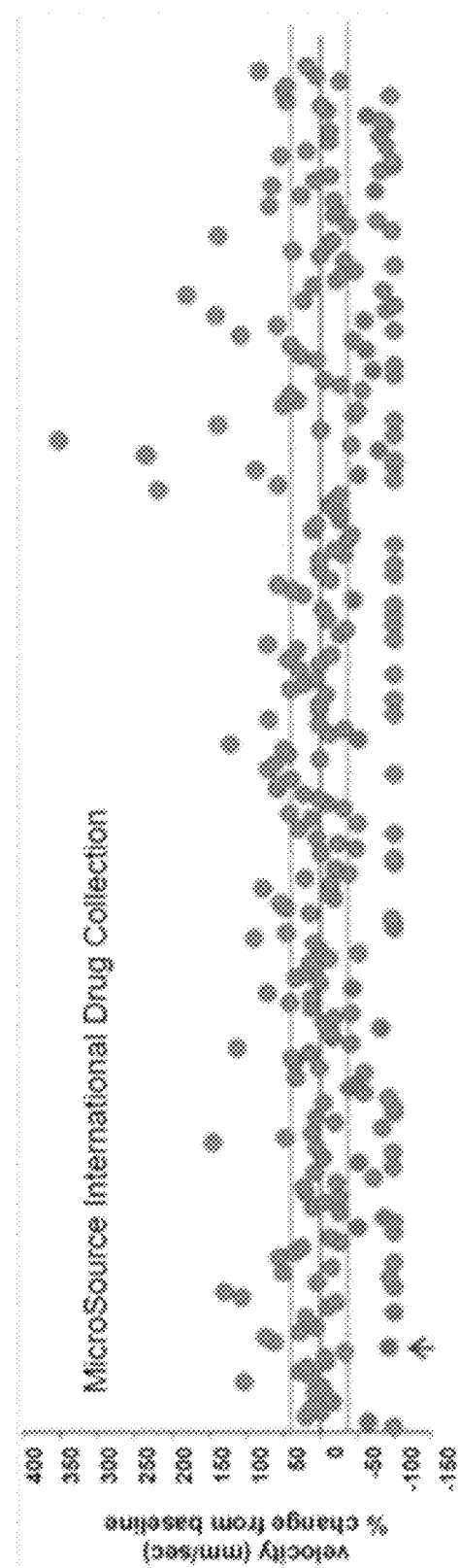
Figure 6D:
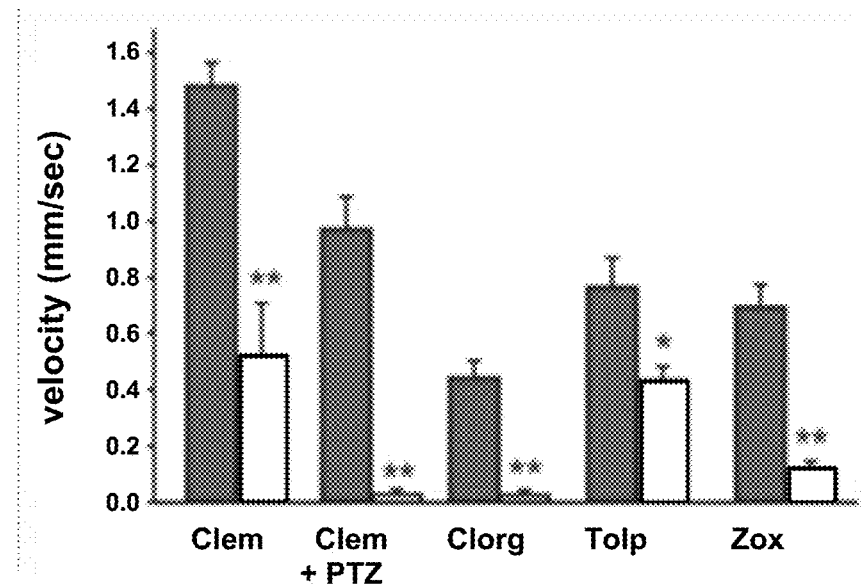

Among the 320 compounds screened in vivo, 18 were found to significantly inhibit spontaneous seizures in scn1Lab mutants to levels comparable to Stage 0 or Stage I behavior and/or reduce mean swim velocity (red circles in FIG. 6C). These 18 compounds were then re-tested on a separate clutch of scn1Lab mutants at concentrations of 667, 67 and 6.7 µM. In the initial screen, 81 compounds were identified as lethal i.e., no visible heartbeat or movement in response to touch after a 30 min exposure and were re-evaluated at a dilution of 1:100; none of these advanced further. The drug library included a number of additional compounds with putative anticonvulsant properties (beclamide, aminohydroxybutyric acid, and tiletamine) that were also ineffective in the 96-well locomotion assay at 667 µM. 14 of the re-tested compounds either failed to successfully inhibit seizure behavior in a second clutch of scn1Lab mutants or only suppressed behavior at the highest drug concentration. Next 4 (out of 18) compounds that were effective in reducing seizure-induced swim activity and mean velocity at all three drug concentrations for further testing were selected: zoxazolamine, clemizole HCl, clorgiline HCl and tolperisone HCl (FIG. 6D). Each of these compounds was evaluated a third time in the locomotion assay at a concentration of 100 µM, and subsequently monitored for forebrain electrographic activity. Clorgiline (a monoamine oxidase A inhibitor) and the muscle relaxants zoxazolamine (Hadra, R. & Millichap J. G., Quantitative assessment of motor function in cerebral palsy: evaluation of zoxazolamine (flexin), a new muscular relaxant agent. *Neurology* 6, 843-852 (1956)) and tolperisone (Sakitama, K., The effects of centrally acting muscle relaxants on the intrathecal noradrenaline-induced facilitation of the flexor reflex mediated by group II afferent fibers in rats. *Jpn. J Pharmacol.* 63, 369-736 (1993)) were identified as "false positives" because they reduced swim activity at this concentration but when the same mutant was embedded in agar electrographic seizure events were still observed (see FIG. 6E).

Figure 6E:
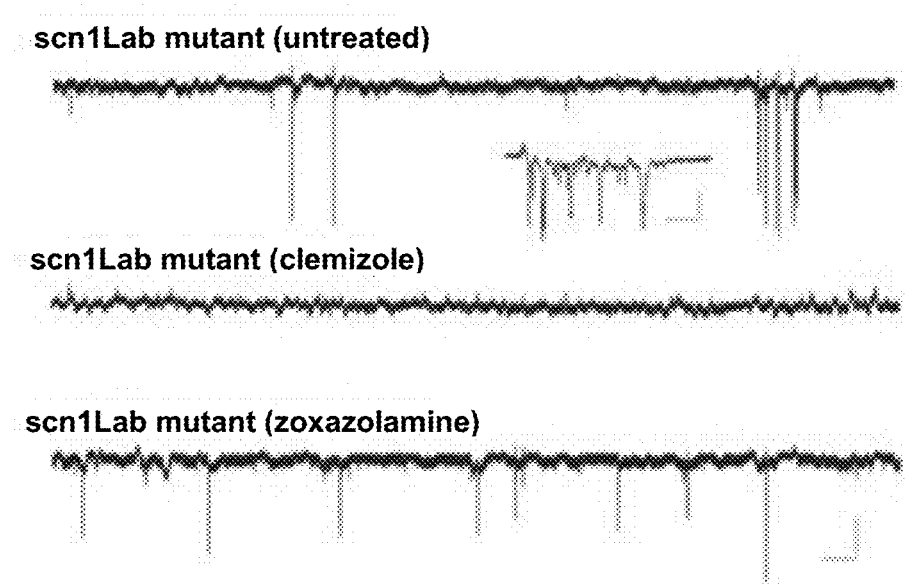
Figure 7A:
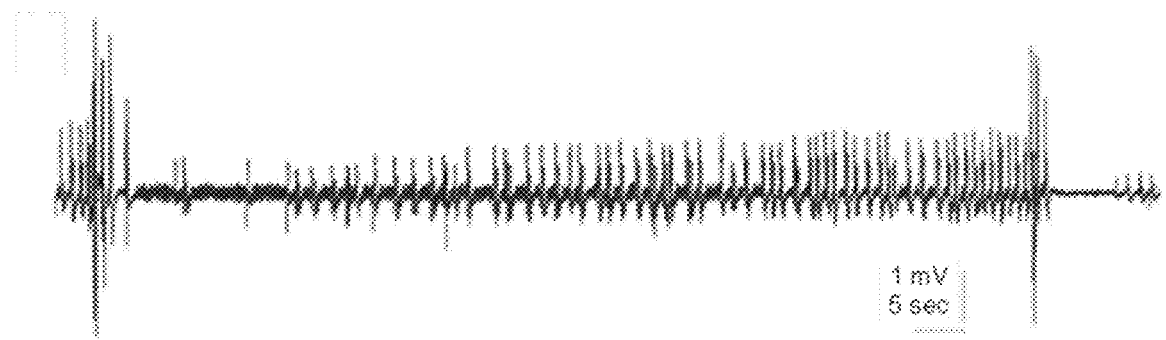
FIGS. 7A-7D: Confirmation of clemizole activity in scn1Laa mutants.
Figure 7B:
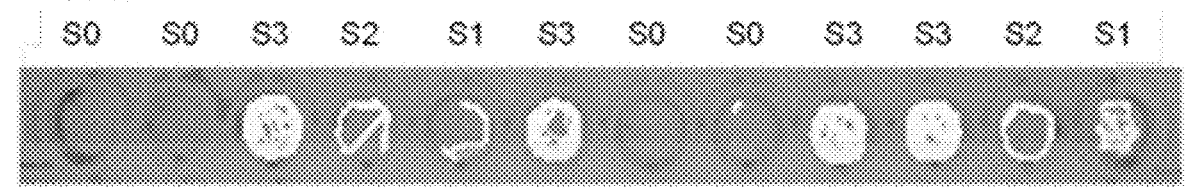
Figure 7C:
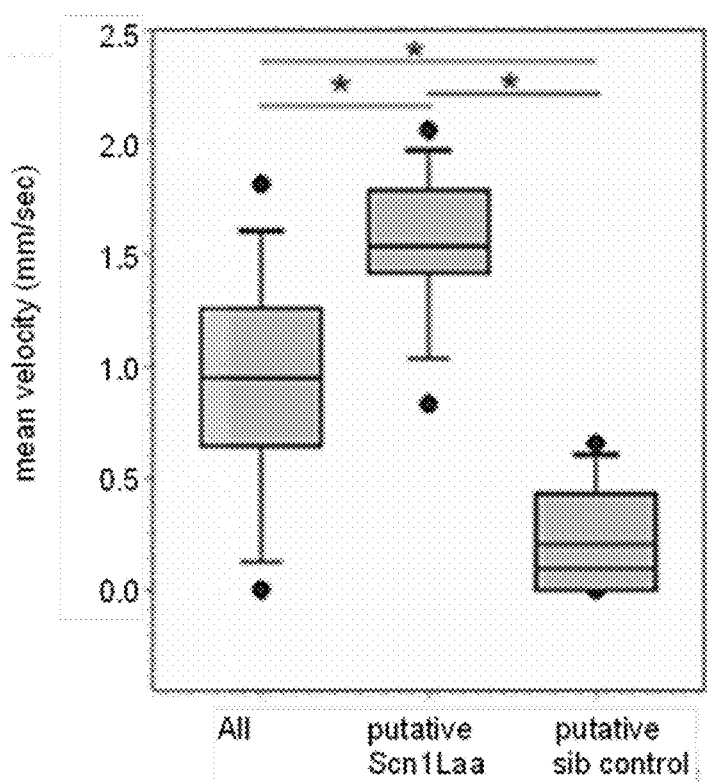
Figure 7D:
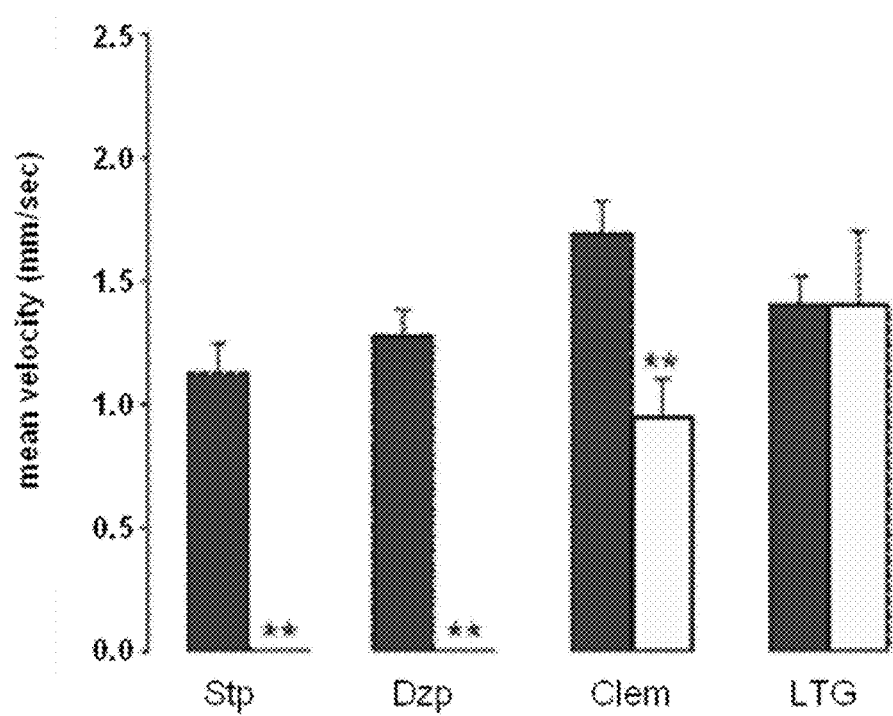
Figure 8:
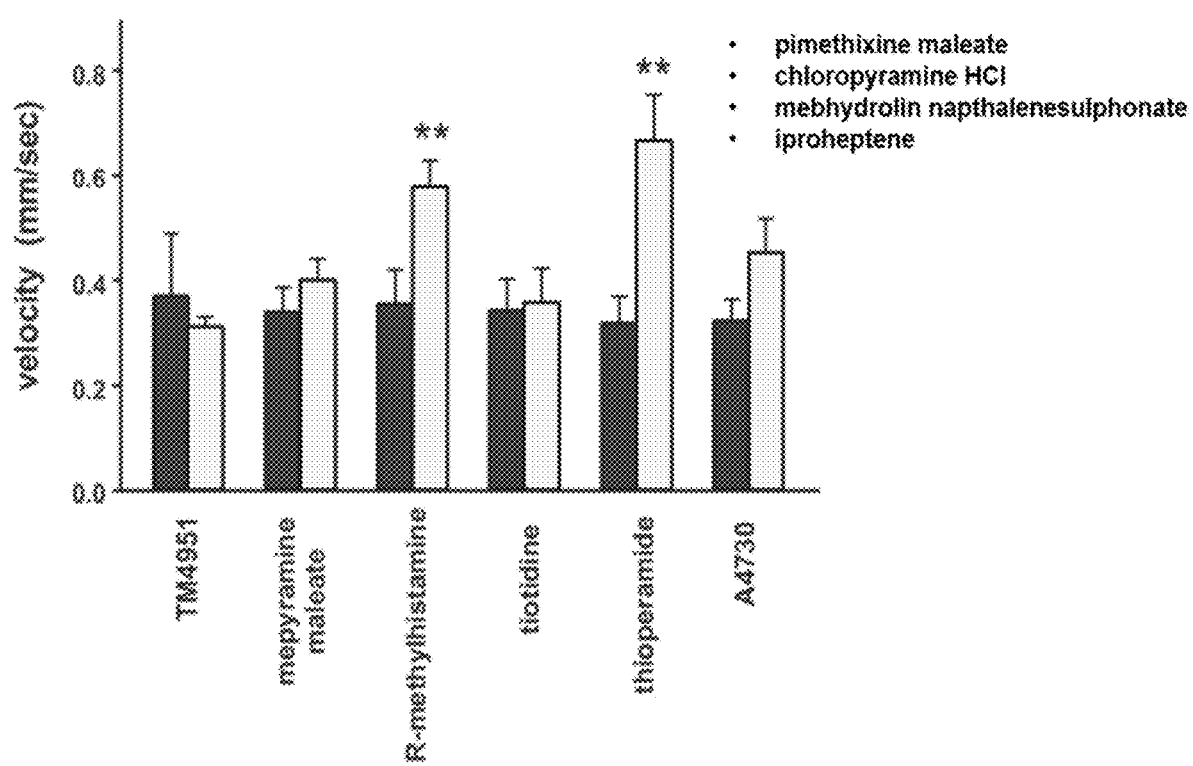
FIG. 8: Antihistamines do not have antiepileptic properties in scn1Lab mutants. Plot of the effect of a variety of antihistamines in the locomotor seizure assay using scn1Lab mutants at 5 dpf. Mean velocity is shown before and after application of a drug. N=7 fish per drug. Additional compounds are listed at right. Bars represent mean±S.E.M. Student's paired t-test or Mann-Whitney Rank Sum test with significance set at p=0.01 (*) or p<0.001 (**). Note: some antihistamines increased seizure activity in this assay.
Figure 9A:
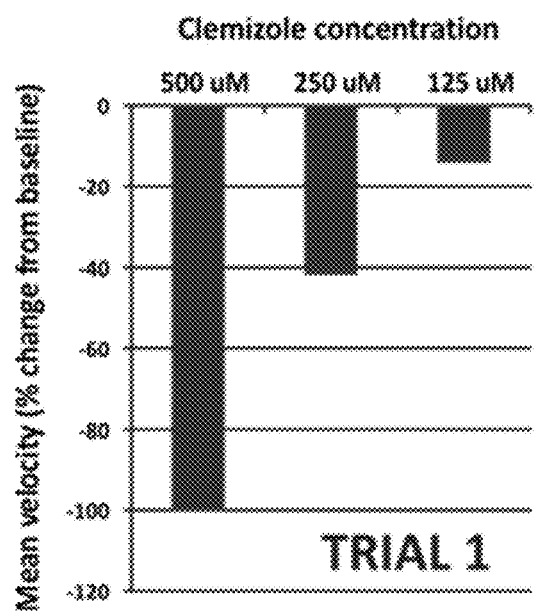
FIGS. 9A-9B: Clemizole concentration-response studies in scn1Lab. Plots from two different concentration-response studies showing the percent inhibition of mean velocity from a baseline value. N=7 fish per concentration and trials were performed on separate clutches of mutant larvae.
Figure 9B:
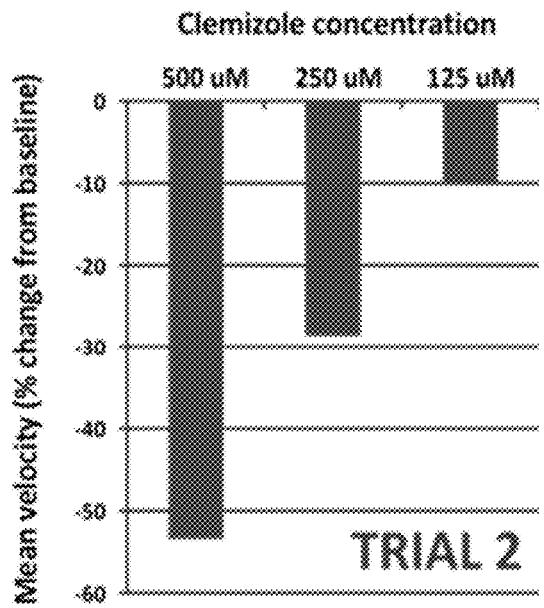

Only one compound, clemizole (antihistamine and NS4B RNA binding inhibitor) (Finkelstein, M., Kromer, C. M., Sweeney, S. A., & Delahunt C. S., Some aspects of the pharmacology of clemizole hydrochloride. *J. Am. Pharm. Assoc. Am. Pharm. Assoc.* 49, 18-22 (1960); Einav, S., Sobol, H. D., Gehrig, E., & Glenn J. S., Discovery of a hepatitis C target and its pharmacological inhibitors by microfluidic affinity analysis. *Nat. Biotechnol.* 26, 1019-1027 (2008)), was effective in suppressing spontaneous seizure activity in both assays (FIG. 6D-E). Clemizole had no significant effect on seizure behavior in the locomotion assay at concentrations between 6.25 and 50 µM (n=33). As an additional evaluation of the therapeutic potential for acute clemizole treatment, it was demonstrated that 100 µM clemizole was effective in reducing seizure behavior in WT zebrafish exposed to 15 mM pentylenetetrazole (FIG. 6D; n=10) i.e., a model of acute seizures based on GABA receptor antagonism. These results suggest that scn1Lab mutants can be used in a high-throughput screen to identify potential lead compounds for Dravet syndrome.

The scn1Lab zebrafish mutant described here is the first simple vertebrate model of a sodium channel mutation that recapitulates features of Dravet syndrome, a catastrophic form of drug-resistant epilepsy in children. These mutants exhibit hyperactivity, including convulsive behavior, spontaneous electrographic seizures, shortened lifespan and a pharmacological profile similar to the human condition. Additional molecular analysis of scn1Lab mutants suggests the absence of gross changes in global gene expression and a lack of compensation, at the RNA level, by other voltage-gated $Na^+$ channel subunits. A two-stage phenotype-based drug screening strategy to identify lead compounds with the potential to ameliorate epilepsy phenotypes associated with SCN1A mutation identified one FDA-approved drug (clemizole).

Electroencephalographic (EEG) activity is typically normal in the first year of life for DS patients with an evolution to abnormal paroxysmal and polyspike activity between 1 and 9 years of age. This age-dependent pattern was mimicked in developing zebrafish larvae at ages where scn1a expression was significant. Forebrain extracellular recordings in very young larvae (3 dpf) appeared largely normal with the occasional small burst of polyspike activity. Frequent brief interictal-like activity with large amplitude polyspike burst discharges became more prominent as larvae aged. The architecture of these electrical events resembled those previously described in wild-type larvae exposed to pentylenetetrazole (Baraban, S. C., Taylor, M. R., Castro, P. A., & Baier H., Pentylenetetrazole induced changes in zebrafish behavior, neural activity and c-fos expression. *Neuroscience* 131, 759-768 (2005)), 4-aminopyridine (Baraban, S. C., et al., A large-scale mutagenesis screen to identify seizure-resistant zebrafish. *Epilepsia* 48, 1151-157 (2007)), linopirdine (Chege, S. W., Hortopan, G. A., Dinday, M. T., & Baraban, S.C., Expression and function of KCNQ channels in larval zebrafish. *Dev. Neurobiol.* 72, 186-198 (2012)) or hyperthermia (Hunt, R. F., Hortopan, G. A., Gillespie, A., & Baraban, S. C., A novel zebrafish model of hyperthermia-induced seizures reveals a role for TRPV4 channels and NMDA-type glutamate receptors. *Exp. Neurol.* 237, 199-206 (2012)).

The appearance of electrographic seizure activity corresponds with hyperactivity, full-body convulsions with associated high-velocity swim activity and brief loss-of-posture in freely behaving mutants. These types of spontaneous behaviors are never observed in wild-type larvae and, again, resemble those previously observed only during exposure to convulsant drugs. These behaviors are an indirect indicator of seizure activity and could be used for rapid in vivo evaluation of drug treatments and lethality in a multi-well format using automated locomotion tracking software (Berghmans, S., Hunt, J., Roach, A., & Goldsmith, P., Zebrafish offer the potential for a primary screen to identify a wide variety of potential anticonvulsants. *Epilepsy Res.* 75, 18-28 (2007); Baxendale, S., et al., Identification of compounds with anti-convulsant properties in a zebrafish model of epileptic seizures. *Dis. Model. Mech.* 5, 773-774 (2012); Winter, M. J., et al., Validation of a larval zebrafish locomotor assay for assessing the seizure liability of early-stage development drugs. *J. Pharm. Tox. Methods* 5, 176-187 (2008)). Seizures in scn1Lab zebrafish mutants were responsive to the ketogenic diet and four AEDs (e.g., valproate, benzodiazepine, potassium bromide and stiripentol) prescribed clinically for patients with DS.

Interestingly, electrographic seizure events in scn1Lab mutants remained unchanged (or perhaps worsened) in response to several commercially available AEDs. While it is possible that drug concentrations higher than 1 mM could be required to abolish electrical events, these would be considered high and potentially non-selective concentrations. In drug trials using an acute PTZ-induced seizure model in larval zebrafish (Baraban, S. C., et al., A large-scale mutagenesis screen to identify seizure-resistant zebrafish. *Epilepsia* 48, 1151-157 (2007); Berghmans, S., Hunt, J., Roach, A., & Goldsmith, P., Zebrafish offer the potential for a primary screen to identify a wide variety of potential anticonvulsants. *Epilepsy Res.* 75, 18-28 (2007); Baxendale, S., et al., Identification of compounds with anti-convulsant properties in a zebrafish model of epileptic seizures. *Dis. Model. Mech.* 5, 773-774 (2012); Afrikanova, T., et al., Validation of the zebrafish pentylenetetrazol seizure model: locomotor versus electrographic responses to antiepileptic drugs. PLoS One 8, e54166 (2013)), AED concentrations of 1 mM and below were often sufficient for assessing antiepileptic activity. With a failure to respond to seven different AEDs this model fits the clinical definition of drug-resistant epilepsy (de Toffol, B., et al., ESPERA study: Applicability of the new ILAE criteria for antiepileptic drug resistance of focal epilepsies in current clinical practice. *Epilepsy Beh* 25, 166-169 (2012)).

For nearly 40 years, the discovery and identification of new AEDs has almost entirely been based upon preclinical animal models of acquired or acute seizures in rodents (Loscher, W. & Schmidt, D., Modern antiepileptic drug development has failed to deliver: Ways out of the current dilemma. *Epilepsia* 52, 657-658 (2011)). This approach successfully identified drugs that block generalized tonic-clonic seizures in humans (Bialer, M. & White H. S., Key factors in the discovery and development of new antiepileptic drugs. *Nat. Rev. Drug Discov.* 9, 10-19 (2012)) but remains time-consuming, resource intensive, expensive and laborious. While testing against PTZ or other types of acquired seizures in zebrafish larvae may be more efficient than similar assays in rodents (Berghmans, S., Hunt, J., Roach, A., & Goldsmith, P., Zebrafish offer the potential for a primary screen to identify a wide variety of potential anticonvulsants. *Epilepsy Res.* 75, 18-28 (2007); Baxendale, S., et al., Identification of compounds with anti-convulsant properties in a zebrafish model of epileptic seizures. *Dis. Model. Mech.* 5, 773-774 (2012) Afrikanova, T., et al., Validation of the zebrafish pentylenetetrazol seizure model: locomotor versus electrographic responses to antiepileptic drugs. PLoS One 8, e54166 (2013)), they ultimately should identify the same classes of compounds.

In contrast, here is described an alternative screening strategy using a 96-well format for rapid automated behavioral monitoring followed by a sensitive electrophysiological assay of spontaneous electrographic seizure activity in a mutant fish mimicking a known human genetic disorder. This in vivo strategy simultaneously monitors lethality and is not limited to SCN1A, but could be applied to any epilepsy disorder. Indeed, this phenotype-based approach could form the basis of a genetically informed or "personalized" approach to drug discovery. While genetically modified mice mimicking known SCN1A mutations and exhibiting epilepsy have been developed, breeding can be complicated, background strain can modify seizure phenotypes and AEDs are rarely tested in these animals. For example, in Scn1a$^{RX/+}$ mutant mice stiripentol and clobazam were only evaluated for effects on hyperthermia-induced seizure thresholds (Cao, D., et al., Efficacy of stiripentol in hyperthermia-induced seizures in a mouse model of Dravet syndrome. *Epilepsia* 53, 1140-1145 (2012)). Treatment of Scn1a$^{+/-}$ mutant mice with clonazepam, an allosteric modulator of GABA-A receptors, rescued some of the autistic-like behaviors but was not evaluated as an antiepileptic (de Toffol, B., et al., ESPERA study: Applicability of the new ILAE criteria for antiepileptic drug resistance of focal epilepsies in current clinical practice. *Epilepsy Beh* 25, 166-169 (2012)).

Where drug-resistant rodent epilepsy models have been described, such as the subgroup of wild-type rats selected from kindling or post-status epilepticus models (Han, S., et al., Autistic-like behaviour in Scn1a+/− mice and rescue by enhanced GABA-mediated neurotransmission. *Nature* 489, 385-390 (2012)), they remain only poorly characterized and are not suitable to initial high-throughput stages of drug screening. In contrast, using a zebrafish scn1Lab mutant with greater than 75% sequence identity for a human sodium channel mutation, a large-scale transcriptomic profiling of over 44,000 probes was completed, demonstrated a developmental progression of scn1Lab channel expression and epileptic phenotypes, analyzed the effects of available antiepileptic therapies, and screened a 320 compound chemical library against spontaneous unprovoked seizures. Although this first proof-of-principle screen was accomplished at one fish per well, 6 to 12 fish per trial and one trial per week, the ease with which zebrafish could be scaled upward (especially in a commercial setting) to study hundreds to thousands of larvae per week make this an attractive system for a rapid large-scale first-stage in vivo drug discovery program. Simultaneous in vivo evaluation of toxicity—one of the greatest sources of failure in moving lead compounds from the bench to the clinic—is a critical advantage of this approach over available organotypic hippocampal culture- or in silica-based screening strategies.

Although any animal model drug discovery data should be treated cautiously, clemizole, a compound with H1 antagonist and NS4B RNA inhibiting properties, is an FDA-approved drug with a safe toxicology profile emerged from this screen and offers an exciting starting point for further research. For example, although it was recently recognized that antihistamines inhibit induced seizures in neonatal rats (Yamada, K., Takizawa, F., Tamura, T., & Kanda T., The effect of antihistamines on seizures induced by increasing-current electroshocks: ketotifen, but not olopatadine, promotes the seizures in infant rats. *Biol. Pharm. Bull.* 35, 693-697 (2012)), without being bound by any particular theory, this is likely not the mechanism of action here. We demonstrated four other H1 antihistamines (pimethixene maleate, chloropyramine HCl, mebhydrolin napthalene-sulfonate and iproheptine) failed to suppress convulsive behavior in scn1Lab mutants. Furthermore, evidence suggests the potential for H1 antihistamines to adversely modify seizures in children (Miyata, I., Saegusa, H., & Sakurai, M., Seizure-modifying potential of histamine H1 antagonists: a clinical observation. *Pediatr. Int.* 53, 706-708 (2011)) indicating that more detailed analysis will be required to identify a mechanism of action. Given that clemizole was also effective in a zebrafish version of the Metrazol test it may be worthwhile to pursue additional pre-clinical testing in the NIH-sponsored Anticonvulsant Drug Development Program at the University of Utah. Most importantly, these studies suggest that in vivo drug screening and experimental analysis of scn1Lab mutant zebrafish could prove extremely valuable to understanding (and treatment) of Dravet syndrome.

Animals. Scn1Lab (didy$^{s552}$) zebrafish embryos were a kind gift from Herwig Baier. Adult HuC:GFP zebrafish were a kind gift from Stephen Ekker. Zebrafish were generated and maintained in accordance with the guidelines of the University of California, San Francisco Committee on the Use and Care of Animals. Zebrafish larvae were maintained in "embryo medium" consisting of 0.03% Instant Ocean (Aquarium Systems, Inc., Mentor, Ohio, U.S.A.) in deionized water containing 0.002% Methylene Blue as a fungicide. Larval zebrafish clutches were bred from scn1Lab heterozygous animals that had been backcrossed to TL wild-type or HuC:GFP zebrafish for at least 7 generations. Homozygous mutants (sorted based on pigmentation) and age-matched sibling larvae were used. Although the precise genetic defect responsible for the skin pigmentation issue is unknown, it is interesting that a 1.5-fold up-regulation of a gene encoding the melanocortin 5a receptor was noted in the microarray data.

Seizure monitoring. Procedures for locomotion tracking and electrophysiology were described (Baraban, S. C., et al., A large-scale mutagenesis screen to identify seizure-resistant zebrafish. *Epilepsia* 48, 1151-157 (2007); Baraban, S. C., Taylor, M. R., Castro, P. A., & Baier H., Pentylenetetrazole induced changes in zebrafish behavior, neural activity and c-fos expression. *Neuroscience* 131, 759-768 (2005)). In pilot experiments, HuC:GFP zebrafish were used in electrophysiology experiments to obtain an estimation of the location of recording electrodes. Locomotion plots were obtained for one fish per well at a recording epoch of 10 min using a DanioVision system running EthoVision XT software (Noldus Information Technology; Leesburg, Va.). Seizure scoring was performed as described (Baraban, S. C., Taylor, M. R., Castro, P. A., & Baier H., Pentylenetetrazole induced changes in zebrafish behavior, neural activity and c-fos expression. *Neuroscience* 131, 759-768 (2005)). Locomotion plots were analyzed for distance traveled (in mm) and mean velocity (in mm/sec). Epileptiform events were analyzed in pClamp (Molecular Devices; Sunnyvale, Calif.) and defined as upward or downward membrane deflections greater than 2× baseline noise level and classified as either interictal-like (100 to 300 msec duration) or ictal-like (1000 to 5000 msec duration). Burst frequency was determined by counting the number of epileptiform events per minute during a 10-min recording epoch. Burst duration was determined by measuring the onset-to-offset interval for all events during the same epoch.

Drugs were obtained from Sigma-Aldrich and dissolved in embryo media. Stock solutions were prepared in embryo media at 1 mM and pH adjusted to ~7.5. Ganaxolone was a kind gift from BioCrea GmbH (Radebeul, Germany). Compounds for drug screening were purchased from MicroSource Discovery Systems, Inc. (International Drug Collection; Gaylordsville, Conn.) and were provided as 10 mM DMSO solutions. Test compounds were dissolved in embryo media and tested at concentrations between 6.7 and 667 µM; final DMSO concentration ~7%. An initial screen concentration of 667 µM was chosen for behavioral studies in freely swimming fish as this falls on the lower range of AED concentrations previously reported in to be effective against PTZ (10-20 mM) induced seizures in larval zebrafish (0.1 to 25 mM) Baraban, S. C., Taylor, M. R., Castro, P. A., & Baier H., Pentylenetetrazole induced changes in zebrafish behavior, neural activity and c-fos expression. *Neuroscience* 131, 759-768 (2005); Berghmans, S., Hunt, J., Roach, A., & Goldsmith, P., Zebrafish offer the potential for a primary screen to identify a wide variety of potential anticonvulsants. *Epilepsy Res.* 75, 18-28 (2007); Afrikanova, T., et al., Validation of the zebrafish pentylenetetrazol seizure model: locomotor versus electrographic responses to antiepileptic drugs. PLoS One 8, e54166 (2013)) and was the most efficient use of the small volume of stock solution (250 µL) provided by MicroSource Discovery Systems, Inc. A slightly higher concentration (1 mM) was chosen for the initial AED validation assays in FIGS. 5 and 6 to account for any potential complications associated with diffusion through the agar. DMSO was evaluated for toxicity at dilutions between 0.01 and 100% using wild-type larvae (n=12 fish per concentration); DMSO at>25% was lethal.

In all drug screening studies compounds were coded and experiments were performed by investigators blind to the nature of the compound. Baseline recordings of seizure activity were obtained from mutants bathed in embryo media; a second plot was then obtained following a solution change to a test compound. Each test compound classified as a "positive hit" in the locomotion assay was visually confirmed as alive based on movement in response to touch and visible heartbeat. WT fish exhibit little to no spontaneous swim activity during these 10 min recording epochs (see FIG. 3B) and were not used in the drug discovery assay.

Procedures for microarray, quantitative PCR and whole-mount in situ hybridization were described (Hortopan, G. A., et al., Spontaneous seizures and altered gene expression in GABA signaling pathways in a mind bomb mutant zebrafish. *J. Neurosci.* 30, 13718-13728 (2010)).

Data are presented as mean and SEM, unless stated otherwise. Pairwise statistical significance was determined with Student's two-tailed unpaired t-test, ANOVA or Mann-Whitney rank sum test, as appropriate, unless stated otherwise. Results were considered significant at P<0.05, unless otherwise indicated.

Example 2

Based on our previous discussion and some activity observed at the 100 and 300 mg/kg doses in the qualitative MES screen in mice, we proceeded with quantitative testing in the MES/scMET/Tox mouse model to determine the ED50/TD50. During the determination of the TPE in the MES model, no activity was observed at the 300 mg/kg starting dose. However, activity was observed at the 500 mg/kg dose with 2/4 animals protected at 0.25 min and 4/4 animals protected at 30 minutes. No activity or toxicity (unable to grasp rotorod) was observed at any other dose or time point tested. No activity was observed in the scMET model. The data in the MES model shows that there is significant activity/protection with ASP469016 in this mouse model with an ED50<400 mg/kg.

Anticonvulsant Screening Results—Mice IP Quantification

| ASP ID: 469016 | * Screen ID: 1 | Sponsor ID: 642 | Sponsor Class: ASP/CM Sponsor |
|---|---|---|---|
| Solvent Code: | MC | Solvent Prep: | M&P; TW |
| Animal Weight: | *g | | |
| Date Started: | 6 May 2014 | Date Completed: | 9 May 2014 |
| Reference: | 503: 294,297.509: 3,4. | | |

ED50 Value

| Test | Time (Hrs) | ED50 | 95% Confidence Interval | Slope | STD Err | PI Value |
|---|---|---|---|---|---|---|
| MES | 0.5 | <400.0 | — | | | |
| SCMET | 0.5 | >250.0 | — | | | |
| TOX | 0.5 | >500 | — | | | |

ED50 Biological Response

| Test | Time (Hrs) | Dose (mg/kg) | Dths | N/F C |
|---|---|---|---|---|
| MES | 0.5 | 350 | | 0/8 |
| MES | 0.5 | 400 | | 7/8 |

-continued

| Test | Time (Hrs) | Dose (mg/kg) | Dths | N/F C |
|---|---|---|---|---|
| MES | 0.5 | 500 | | 4/4 |
| SCMET | 0.5 | 200 | | 0/8 |
| SCMET | 0.5 | 250 | | 0/4 |
| TOX | 0.5 | 500 | | 0/4 |

Note:
Presence of an asterisk (*) indicates that there are multiple comment codes.

Time to Peak Effect

| | | | Time (Hours) | | | | | | | | |
|---|---|---|---|---|---|---|---|---|---|---|---|
| Test | Dose (mg/kg) | Dths | 0.25 N/F C | 0.5 N/F C | 1.0 N/F C | 2.0 N/F C | 4.0 N/F C | 6.0 N/F C | 8.0 N/F C | 24 N/F C | 3.0 N/F C |
| MES | 300 | | 0/4 | 0/4 | 0/4 | 0/4 | 0/4 | / | / | / | / |
| MES | 500 | | 2/4 | 4/4 | 0/4 | 0/4 | 0/4 | / | / | / | / |
| TOX | 400 | | 0/8 | 0/8 | / | / | / | / | / | / | / |
| TOX | 500 | | 0/4 | 0/4 | 0/4 | / | / | / | / | / | / |

Note:
N/F = number of animals active or toxic over the number tested.
C = Comment code. Presence of an asterisk (*) indicates that there are multiple comment codes.
MES doses 350 m/kg and 400 m/kg and Scmet dose 200 m/kg were done with the Ori batch and all the other doses were done with the A batch.

Example 3

ASP469016 was tested in our initial T31 (MES/scMET/Tox) screen at 30, 100, and 300 mg/kg. The data for each condition is presented as N/F, where N equals the number of animals protected and F equals the number of animals tested. For tests of toxicity (TOX), N equals the number of animals displaying toxic effects and F equals the number of animals tested. Codes in the C column refer to comments from the technicians performing the experiment and are defined in the comments section if necessary. Any deaths are noted. As shown in the 6 Hz (32 mA) model only ¼ animals were protected at 100 mg/kg at 30 min. In the MES-induced seizure model only ¼ animals were protected at 100 and 300 mg/kg at 30 min. No toxicity (unable to grasp rotorod) or activity was detected at any other dose or time point tested.

Anticonvulsant Screening Results—Mice MES and 6Hz Identification

| ASP ID: 469016 | U | Screen ID: 1 | Sponsor ID: 642 | | Sponsor Class: ASP/CM Sponsor | |
|---|---|---|---|---|---|---|
| Solvent Code: | MC | | Solvent Prep: | M&P; SB | Route Code: | IP |
| Animal Weight: | *g | | | | 6 Hz Current (mA): | 32 |
| Date Started: | 11 Feb. 2014 | | Date Completed: | 11 Feb. 2014 | | |
| Reference: | 503: 153. | | | | | |

Response 15

| Time (Hours) | | | 0.5 | 2.0 | 0.3 | 1.0 | 4.0 | 6.0 | 3.0 | 8.0 | 24 |
|---|---|---|---|---|---|---|---|---|---|---|---|
| Test | Dose | Form Dths | N/F C | N/F C | N/F C | N/F C | N/F C | N/F C | N/F C | N/F C | N/F C |
| 6 Hz | 30 | | 0/4 | 0/4 | / | / | / | / | / | / | / |
| 6 Hz | 100 | | 1/4 | 0/4 | / | / | / | / | / | / | / |
| 6 Hz | 300 | | 0/4 | 0/4 | / | / | / | / | / | / | / |
| MES | 30 | | 0/4 | 0/4 | / | / | / | / | / | / | / |
| MES | 100 | | 1/4 | 0/4 | / | / | / | / | / | / | / |
| MES | 300 | | 1/4 | 0/4 | / | / | / | / | / | / | / |
| TOX | 30 | SUS | 0/8 | 0/8 | / | / | / | / | / | / | / |
| TOX | 100 | SUS | 0/8 | 0/8 | / | / | / | / | / | / | / |
| TOX | 300 | SUS | 0/8 | 0/8 | / | / | / | / | / | / | / |

Note:
N/F = number of animals active or toxic over the number tested.
C = Comment code. Presence of an asterisk (*) indicates that there are multiple comment codes.

Example 4

Clemizole (149934-L6) was tested in the CEREP BioPrint Profile, which is a panel of 139 different in vitro receptor binding and enzyme assays. For the initial BioPrint screen, a free compound concentration of 10 μM (1.0E-5 M) was used. Compound binding was calculated as a % inhibition of the binding of a radioactively labeled ligand specific for each target. Compound enzyme inhibition effect was calculated as a % inhibition of control enzyme activity. In each experiment, the respective reference compound was tested concurrently with Clemizole (149934-L6), and the data were compared with historical values determined at CEREP. The experiment was accepted in accordance with CEREP's validation Standard Operating Procedure. Results showing an inhibition (or stimulation for assays run in basal conditions) higher than 50% are considered to represent significant effects of the test compounds. A summary of these results is shown below:

| Assay | 1.0E–05M |
|---|---|
| 5-HT$_{2A}$(h) (agonist radioligand) | 86% |
| 5-HT$_{2B}$(h) (agonist radioligand) | 82.5% |
| 5-HT$_{1A}$(h) (agonist radioligand) | 19.5% |
| 5-HT$_{1B}$(h) (agonist radioligand) | 4.4% |
| 5-HT$_{1D}$(h) (agonist radioligand) | 22.7% |
| 5-HT$_3$(h) (agonist radioligand) | 9.8% |
| 5-HT$_{4e}$(h) (agonist radioligand) | −1.0% |
| GABA$_{A1}$(h) (agonist radioligand) | −9.6% |
| GABA$_{B(1b)}$(h) (agonist radioligand) | −5.9% |
| BZD (central) (agonist radioligand) | −19.6% |
| CB$_1$(h) (agonist radioligand) | 17.9% |
| CB$_2$(h) (agonist radioligand) | 28.4% |
| GABA-gated Cl channel | 24.9% |

-continued

| Assay | 1.0E–05M |
|---|---|
| SK-Ca channel | −0.2% |
| GABA transporter | −5.9% |

Example 5

Figure 10:
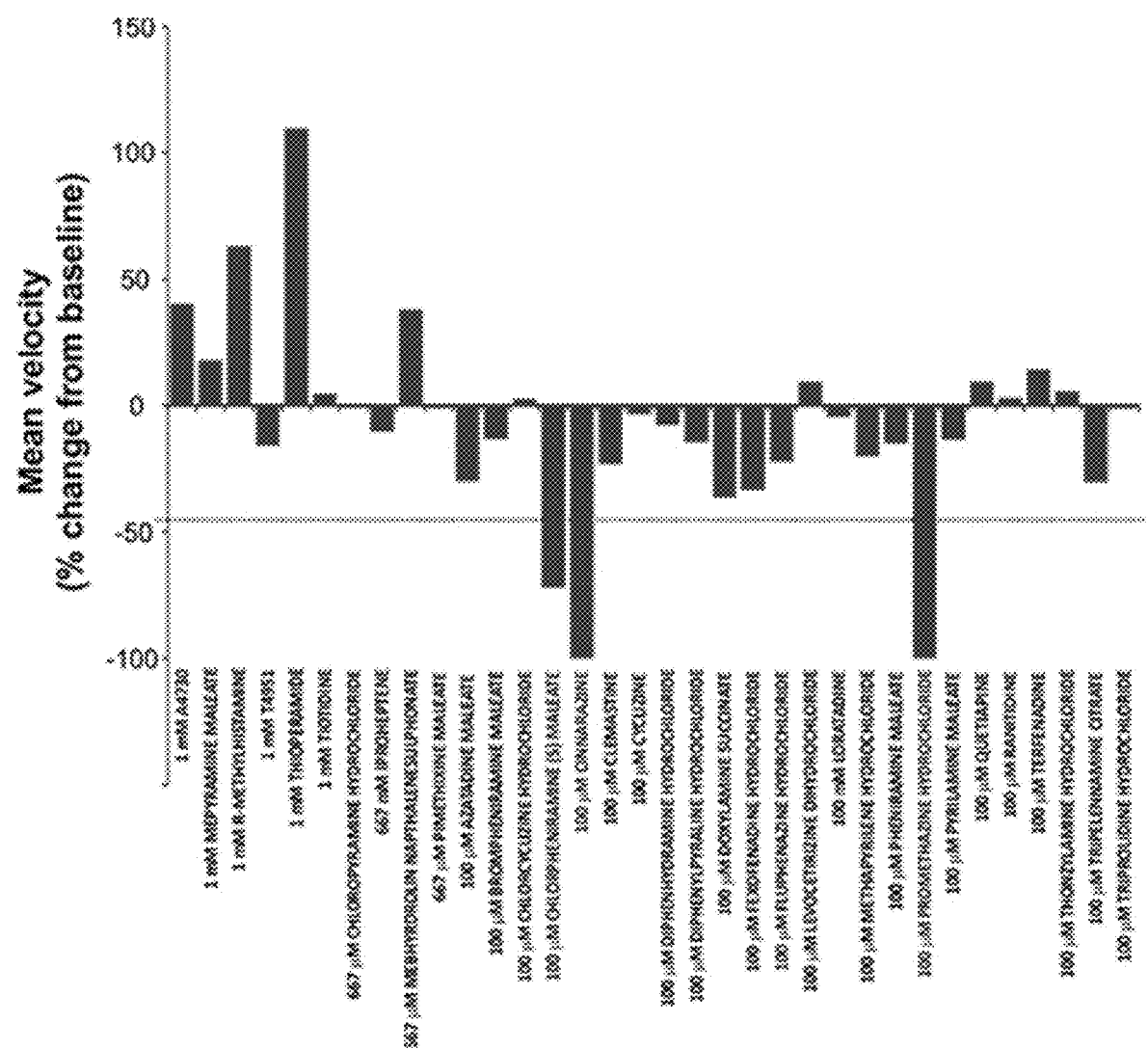
FIG. 10: A shelf screen was performed using 34 different compounds with antihistamine properties. All compounds shown were tested against spontaneous seizures in scn1Lab larvae at 5 dpf; 6-10 fish per drug. Results are shown as a change in mean velocity from locomotion tracking data plots. Compounds were tested at concentrations between 0.1 and 1 mM. The threshold for a positive hit is indicated by the dashed line. Three compounds reached this threshold, but all 3 were identified as toxic (arrows).

Clemizole does not exert antiepileptic activity via an anti-histaminergic mechanism of action. 32 different antihistamine compounds, FIG. 10, were screened in the scn1Lab zebrafish assay and none of the compounds mimicked the antiepileptic action of clemizole. Three of the compounds were toxic and, consistent with clinical reports that antihistamines can exacerbate seizures in pediatric epilepsy patients, five compounds increased seizure behavior.

Example 6

Applicants screened a Selleck Customized Library containing 62 drugs acting on serotonin signaling pathways. These compounds were initially screened in the zebrafish locomotion assay and 15 compounds were identified as positive hits in the first-pass locomotion assay (details of the assay can be found in Baraban et al. Nat. Comm. 2013 and Dinday and Baraban, eNeuro 2015) and can be seen in FIG. 11. These studies suggest that modulation of 5HT signaling, especially activation of postsynaptic 5HT receptors, has potential antiepileptic activity.

Concentration-response re-test studies on all of the 5HT compounds identified in the first-pass locomotion assay.

Figure 12A:
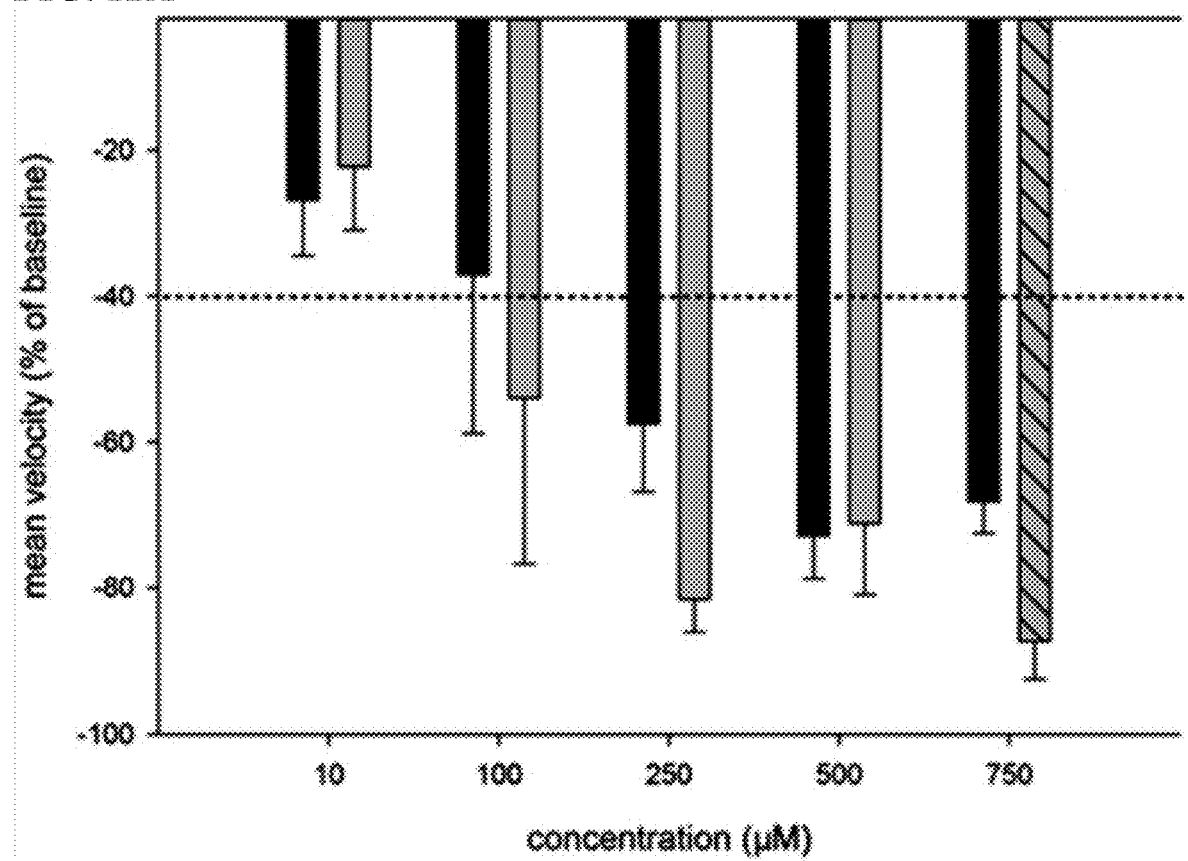
FIGS. 12A-12B.
Figure 12B:
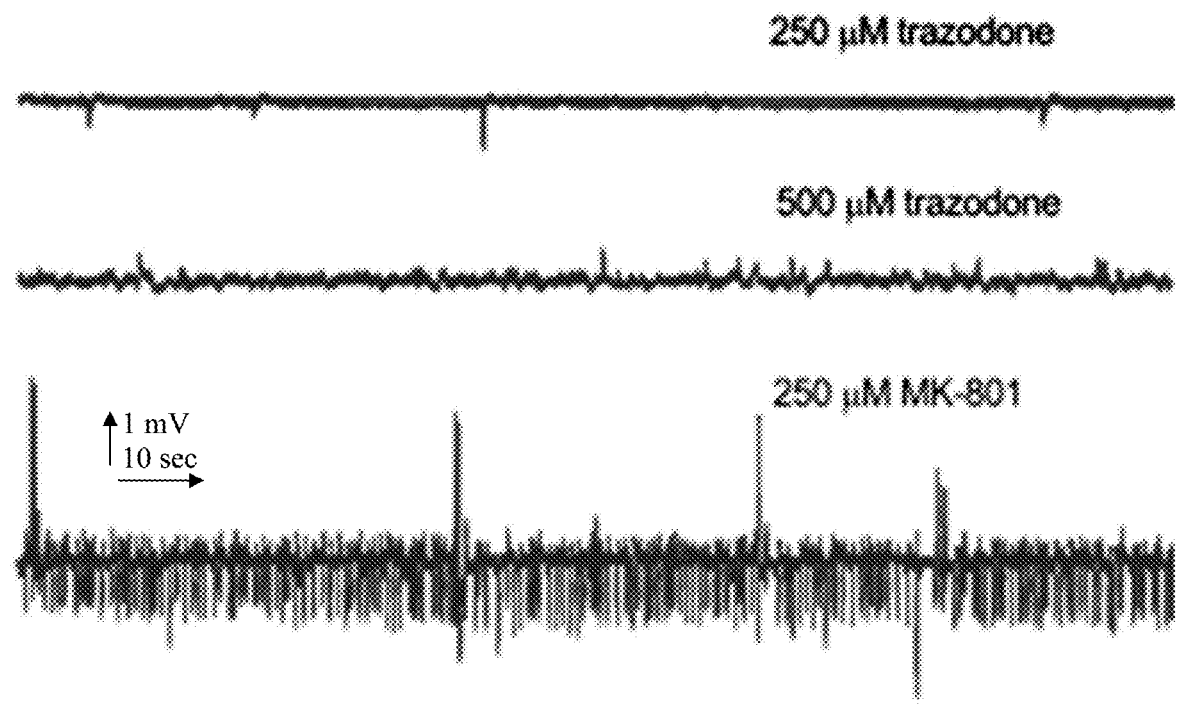

Trazodone results (Desryl, Oleptro) is shown as a representative example. In addition to showing robust inhibition of spontaneous seizure behavior in the locomotion assay at concentrations between 100 and 750 μM (FIG. 12A), trazodone also effectively suppressed EEG activity in the scn1Lab mutants (n=15) at concentrations between 250 and 500 μM (FIG. 12B) and in separate trials with drug washout (n=12). Compounds with positive hits include sumatriptan, naratriptap, rizatriptan, zolmitriptan, urapidil, BRL-54443 (3-(1-methylpiperidin-4-yl)-1H-indol-5-ol), lorcaserin, buspirone, ziprasidone, TCB-2 ((4-Bromo-3,6-dimethoxybenzocyclobuten-1-yl)methylamine hydrobromide), BRL-15572 (3-(4-(4-chlorophenyl)piperazin-1-yl)-1,1-diphenyl-2-propanol), trazodone, BMY 7378 (8-(2-[4-(2-methoxyphenyl)-1-piperazinyl]ethyl)-8-azaspiro[4.5]decane-7,9-dione), atomoxetine, and venlafaxine.

Additional Embodiments

Embodiment 1. A method of treating an epilepsy disorder, the method including administering to a subject in need thereof a therapeutically effective amount of a 5HT receptor agonist, or a pharmaceutically acceptable salt thereof.

Embodiment 2. The method of embodiment 1, wherein the 5HT receptor agonist is a 5HT2A receptor agonist or a 5HT2B receptor agonist.

Embodiment 3. The method of embodiment 2, wherein the 5HT receptor agonist is a dual 5HT2A receptor and 5HT2B receptor agonist.

Embodiment 4. The method of embodiment 1, wherein the 5HT receptor agonist is not clemizole or fenfluramine.

Embodiment 5. The method of embodiment 1, wherein the 5HT receptor agonist binds directly to a 5HT receptor.

Embodiment 6. The method of embodiment 1, wherein the 5HT receptor agonist specifically activates a 5HT receptor.

Embodiment 7. The method of embodiment 1, wherein the 5HT receptor agonist provides increased activity mediated by 5HT2A receptor or 5HT2B receptor with equivalent or reduced activity mediated through 5HT2C receptor.

Embodiment 8. The method of embodiment 1, wherein the 5HT receptor agonist is not a serotonin reuptake inhibitor.

Embodiment 9. The method of embodiment 1, wherein the 5HT receptor agonist does not significantly bind to or modulate the activity of at least one of 5HT1A, 5HT1B, 5HT1D, 5HT2C, 5HT3, 5HT4, 5HT6, 5HT7, NPY Y1 receptor, L-type Ca channel, N-type Ca channel, SK-Ca channel, GABA-gated Cl channel, GABA transporter, GABA-A1 receptor, GABA-B1b receptor, Na channel, 5HT transporter, CB1 receptor, CB2 receptor, BZD or Estrogen ER alpha.

Embodiment 10. The method of embodiment 1, wherein the 5HT receptor agonist is flibanserin, DOI HCl, norfenfluramine or BW 723C86.

Embodiment 11. The method of embodiment 1, wherein the 5HT receptor agonist is sumatriptan, naratriptap, rizatriptan, zolmitriptan, urapidil, BRL-54443 (3-(1-methylpiperidin-4-yl)-1H-indol-5-ol), lorcaserin, buspirone, ziprasidone, TCB-2 ((4-Bromo-3,6-dimethoxybenzocyclobuten-1-yl)methylamine hydrobromide), BRL-15572 (3-(4-(4-chlorophenyl)piperazin-1-yl)-1,1-diphenyl-2-propanol), trazodone, BMY 7378 (8-(2-[4-(2-methoxyphenyl)-1-piperazinyl]ethyl)-8-azaspiro[4.5]decane-7,9-dione), atomoxetine, or venlafaxine.

Embodiment 12. The method of embodiment 1, wherein the 5HT receptor agonist is trazodone or a pharmaceutically acceptable salt thereof. In embodiments, the pharmaceutically acceptable salt of trazadone is hydrochloride, hydrobromide, phosphate, sulfate, methanesulfonate, nitrate, maleate, acetate, citrate, fumarate, propionate, tartrate, succinate, benzoate, glutamate, or a quaternary ammonium salt.

Embodiment 13. The method of embodiment 1, wherein the epilepsy disorder is Dravet Syndrome, Lennox-Gastaut Syndrome, infantile spasm, or Ohtahara Syndrome.

Embodiment 14. The method of embodiment 13, wherein the epilepsy disorder is Dravet Syndrome.

Embodiment 15. The method of embodiment 1, wherein the epilepsy disorder is a pediatric epilepsy disorder.

Embodiment 16. The method of embodiment 1, wherein the subject has a cardiovascular disease.

Embodiment 17. The method of embodiment 1, wherein the subject is resistant to treatment with a serotonin reuptake inhibitor.

Embodiment 18. The method of embodiment 1, wherein the subject is susceptible to side effects when administered a serotonin reuptake inhibitor.

Embodiment 19. The method of embodiment 17 or 18 or, wherein the serotonin reuptake inhibitor is fenfluramine.

Embodiment 20. The method of embodiment 1, wherein the subject has a ketogenic diet.

Embodiment 21. The method of embodiment 1, wherein the 5HT receptor agonist inhibits compulsive behaviors or electrographic seizures in an epilepsy subject, an Alzheimer's disease subject, an autism subject, or a Parkinson's disease subject.

Embodiment 22. The method of embodiment 1, wherein the 5HT receptor agonist reduces the incidence of unprovoked seizures in the subject when compared to the absence of the 5HT receptor agonist.

Embodiment 23. The method of embodiment 1, wherein the administration of the 5HT receptor agonist reduces or prevents myoclonus seizures or status epilepticus in the subject when compared to the absence of 5HT receptor agonist.

Embodiment 24. The method of embodiment 1, wherein the 5HT receptor agonist is administered to the subject at an amount of about 0.1 mg to about 1000 mg per kg body weight.

Embodiment 25. The method of embodiment 22, wherein the 5HT receptor agonist is administered to the subject in a daily dose of about 0.1 mg to about 1000 mg per kg body weight to the subject.

Embodiment 26. The method of embodiment 1, wherein the 5HT receptor agonist is co-administered with an anti-epileptic drug (AED).

Embodiment 27. The method of embodiment 1, wherein the 5HT receptor agonist is an adjunctive therapy with an anti-epileptic drug (AED).

Embodiment 28. The method of embodiment 26 or 27, wherein the AED is acetazolamide, benzodiazepine, cannabadiols, carbamazepine, clobazam, clonazepam, eslicarbazepine acetate, ethosuximide, ethotoin, felbamate, fenfluramine, fosphenytoin, gabapentin, ganaxolone, huperzine A, lacosamide, lamotrigine, levetiracetam, nitrazepam, oxcarbazepine, perampanel, piracetam, phenobarbital, phenytoin, potassium bromide, pregabalin, primidone, retigabine, rufinamide, valproic acid, sodium valproate, stiripentol, tiagabine, topiramate, vigabatrin, or zonisamide.

Embodiment 29. The method of embodiment 28, wherein the AED is valproic acid, sodium valproate, clonazepam, ethosuximide, felbamate, gabapentin, carbamazepine, oxcarbazepine, lamotrigine, levetiracetam, benzodiazepine, phenobarbital, pregabalin, primidone, tiagabine, topiramate, potassium bromide, phenytoin, stiripentol, vigabatrin, or zonisamide.

Embodiment 30. The method of embodiment 29, wherein the AED is valproic acid, sodium valproate, gabapentin, topiramate, carbamazepine, oxcarbazepine, or vigabatrin.

Embodiment 31. The method of embodiment 26, wherein the AED is not fenfluramine or topiramate.

Embodiment 32. The method of embodiment 26, wherein the AED is administered simultaneously with or sequentially with the 5HT receptor agonist.

Embodiment 33. A method of treating an epilepsy disorder, the method including administering to a subject in need thereof a therapeutically effective amount of a 5HT receptor agonist, or a pharmaceutically acceptable salt thereof, wherein the subject has a cardiovascular disease, is resistant to treatment with a serotonin reuptake inhibitor, or is susceptible to side effects when administered a serotonin reuptake inhibitor.

Embodiment 34. The method of embodiment 33, wherein the 5HT receptor agonist is a 5HT2A receptor agonist or a 5HT2B receptor agonist.

Embodiment 35. The method of embodiment 32, wherein the 5HT receptor agonist is a dual 5HT2A receptor and 5HT2B receptor agonist.

Embodiment 36. The method of embodiment 33, wherein the 5HT receptor agonist is clemizole, a clemizole analog, or a pharmaceutically acceptable salt thereof.

Embodiment 37. The method of embodiment 36, wherein the pharmaceutically acceptable salt is clemizole HCl.

Embodiment 38. The method of embodiment 36, wherein the clemizole, the clemizole analog, or the pharmaceutically acceptable salt thereof forms part of a pharmaceutical composition.

Embodiment 39. The method of embodiment 38, wherein the pharmaceutical composition further includes a pharmaceutically acceptable excipient.

Embodiment 40. The method of embodiment 38, wherein the pharmaceutical composition includes a therapeutically effective amount of clemizole, the clemizole analog, or the pharmaceutically acceptable salt thereof.

Embodiment 41. The method of embodiment 40, wherein the pharmaceutical composition is co-administered with an anti-epileptic drug (AED).

Embodiment 42. The method of embodiment 41, wherein the pharmaceutical composition includes clemizole, the clemizole analog, or the pharmaceutically acceptable salt thereof and an AED.

Embodiment 43. The method of embodiment 33, wherein the 5HT receptor agonist is not fenfluramine.

Embodiment 44. The method of embodiment 33, wherein the 5HT receptor agonist binds directly to a 5HT receptor.

Embodiment 45. The method of embodiment 33, wherein the 5HT receptor agonist specifically activates a 5HT receptor.

Embodiment 46. The method of embodiment 33, wherein the 5HT receptor agonist provides increased activity mediated by 5HT2A receptor or 5HT2B receptor with equivalent or reduced activity mediated through 5HT2C receptor.

Embodiment 47. The method of embodiment 33, wherein the 5HT receptor agonist is not a serotonin reuptake inhibitor.

Embodiment 48. The method of embodiment 33, wherein the 5HT receptor agonist does not significantly bind to or modulate the activity of at least one of 5HT1A, 5HT1B, 5HT1D, 5HT2C, 5HT3, 5HT4, 5HT6, 5HT7, NPY Y1 receptor, L-type Ca channel, N-type Ca channel, SK-Ca channel, GABA-gated Cl channel, GABA transporter, GABA-A1 receptor, GABA-B1b receptor, Na channel, 5HT transporter, CB1 receptor, CB2 receptor, BZD or Estrogen ER alpha.

Embodiment 49. The method of embodiment 33, wherein the 5HT receptor agonist is sumatriptan, naratriptap, rizatriptan, zolmitriptan, urapidil, BRL-54443 (3-(1-methylpiperidin-4-yl)-1H-indol-5-ol), lorcaserin, buspirone, ziprasidone, TCB-2 ((4-Bromo-3,6-dimethoxybenzocyclobuten-1-yl)methylamine hydrobromide), BRL-15572 (3-(4-(4-chlorophenyl)piperazin-1-yl)-1,1-diphenyl-2-propanol), trazodone, BMY 7378 (8-(2-[4-(2-methoxyphenyl)-1-piperazinyl]ethyl)-8-azaspiro[4.5]decane-7,9-dione), atomoxetine, or venlafaxine.

Embodiment 50. The method of embodiment 33, wherein the 5HT receptor agonist is trazodone or a pharmaceutically acceptable salt thereof.

Embodiment 51. A method of modulating activity of a 5HT receptor including contacting a 5HT receptor with clemizole, a clemizole analog, or a pharmaceutically acceptable salt thereof.

Embodiment 52. The method of embodiment 51, wherein the modulating is activating.

Embodiment 53. The method of embodiment 51, wherein the 5HT receptor is a 5HT2A receptor or a 5HT2B receptor.

Embodiment 54. A method of treating a disease or disorder caused by a deficiency of serotonin in the brain or under activity of one or more 5HT receptors including administering to a subject in need thereof a therapeutically effective amount of clemizole, a clemizole analog, or a pharmaceutically acceptable salt thereof.

Embodiment 55. The method of embodiment 54, wherein the disease or disorder is not epilepsy.

Embodiment 56. The method of embodiment 54, wherein the disease or disorder is not Dravet Syndrome.

Embodiment 57. The method of embodiment 51, wherein the disease or disorder is selected from the group consisting of migraine, Fragile X syndrome, Prader-Willi syndrome, schizophrenia, depression, Alzheimer's disease, autism, neuropathic pain, Parkinson's disease, irritable bowel, disorder, and dementia.

Embodiment 58. The method of embodiment 50, wherein the pharmaceutically acceptable salt is clemizole HCl.

What is claimed is:

1. A method of treating an infantile epileptic encephalopathy, said method comprising administering to a subject in need thereof a therapeutically effective amount of a 5HT receptor agonist, wherein said 5HT receptor agonist is clemizole, a clemizole analog, or a pharmaceutically acceptable salt thereof.

2. A method of treating an infantile epileptic encephalopathy, said method comprising administering to a subject in need thereof a therapeutically effective amount of a 5HT receptor agonist and an anti-epilepsy drug (AED), wherein said 5HT receptor agonist is clemizole, a clemizole analog, or a pharmaceutically acceptable salt thereof.

3. The method of claim 1 or 2, wherein said clemizole, a clemizole analog, or a pharmaceutically acceptable salt thereof inhibits compulsive behaviors or electrographic seizures in said subject.

4. The method of claim 1 or 2, wherein said clemizole, a clemizole analog, or a pharmaceutically acceptable salt thereof reduces the incidence of unprovoked seizures in said subject when compared to the absence of said 5HT receptor agonist.

5. The method of claim 1 or 2, wherein said clemizole, a clemizole analog, or a pharmaceutically acceptable salt thereof reduces or prevents myoclonus seizures or status epilepticus in said subject when compared to the absence of said 5HT receptor agonist.

6. The method of claim 2, wherein said AED is acetazolamide, benzodiazepine, carbamazepine, clobazam, clonazepam, eslicarbazepine acetate, ethosuximide, ethotoin, felbamate, fenfluramine, fosphenytoin, gabapentin, ganaxolone, huperzine A, lacosamide, lamotrigine, levetiracetam, nitrazepam, oxcarbazepine, perampanel, piracetam, phenobarbital, phenytoin, potassium bromide, pregabalin, primidone, retigabine, rufinamide, valproic acid, sodium valproate, stiripentol, tiagabine, topiramate, vigabatrin, or zonisamide.

7. The method of claim 2, wherein said AED is valproic acid, sodium valproate, clonazepam, ethosuximide, felbamate, gabapentin, carbamazepine, lamotrigine, levetiracetam, benzodiazepine, phenobarbital, oxcarbazepine, pregabalin, primidone, tiagabine, topiramate, potassium bromide, phenytoin, stiripentol, vigabatrin, or zonisamide.

8. The method of claim 2, wherein said AED is valproic acid, sodium valproate, gabapentin, carbamazepine, oxcarbazepine, or vigabatrin.

9. The method of claim 1 or 2, wherein said 5HT receptor agonist is not a serotonin reuptake inhibitor.

10. The method of claim 1 or 2, wherein said pharmaceutically acceptable salt is clemizole HCl.

* * * * *